(12) United States Patent
Inam et al.

(10) Patent No.: US 11,963,846 B2
(45) Date of Patent: Apr. 23, 2024

(54) SYSTEMS AND METHODS FOR INTEGRITY ANALYSIS OF CLINICAL DATA

(71) Applicant: Overjet, Inc., Allston, MA (US)

(72) Inventors: Wardah Inam, Boston, MA (US); Robert Faiella, Cotuit, MA (US); Shaju Puthussery, Chestnut Hill, MA (US); Samet Taspinar, Brooklyn, NY (US); Alexander Albert Joseph Jelicich, Citrus Heights, CA (US); Deepak Ramaswamy, Newton, MA (US)

(73) Assignee: OverJet, Inc., Boston, MA (US)

( * ) Notice: Subject to any disclaimer, the term of this patent is extended or adjusted under 35 U.S.C. 154(b) by 535 days.

(21) Appl. No.: 17/373,178

(22) Filed: Jul. 12, 2021

(65) Prior Publication Data

US 2021/0338387 A1    Nov. 4, 2021

Related U.S. Application Data

(63) Continuation-in-part of application No. 16/752,362, filed on Jan. 24, 2020, now Pat. No. 11,158,046.
(Continued)

(51) Int. Cl.
*A61C 9/00* (2006.01)
*G06T 7/00* (2017.01)
(Continued)

(52) U.S. Cl.
CPC .......... *A61C 9/0053* (2013.01); *G06T 7/0012* (2013.01); *G06T 7/62* (2017.01);
(Continued)

(58) Field of Classification Search
CPC ...... A61C 9/0053; G16H 50/20; G16H 20/00; G06T 7/62; G06T 7/0012;
(Continued)

(56) References Cited

U.S. PATENT DOCUMENTS 5,416,822 A    5/1995 Kunik
6,567,100 B1   5/2003 Otani et al.
(Continued)

FOREIGN PATENT DOCUMENTS

EP          2976746 B1        1/2019
KR    10-2018-0068703 A       6/2018
KR    10-2020-0015379 A       2/2020

OTHER PUBLICATIONS

International Search Report and Written Opinion dated Oct. 29, 2021 in PCT Application No. PCT/US2021/041279.

*Primary Examiner* — Allen H Nguyen
(74) *Attorney, Agent, or Firm* — Sunstein LLP

(57) ABSTRACT

Disclosed are implementations that include a clinical data analysis method including obtaining dental data that includes input radiographic image data for at least one dental object, and identifying, by machine learning models, a first dental feature in the input radiographic image data for the at least one dental object, and at least one other feature in the dental object comprising at least partly a healthy dental structure. The method additionally includes computing at least one dimensioned property representative of physical dimensions of the first dental feature and the at least one other feature, deriving, based on the computed at least one dimensioned property, a ratio indicative of an extent of a dental clinical condition associated with the identified first dental feature, and determining a treatment plan based on a comparison of the at least one dimensioned property ratio to a respective threshold value.

20 Claims, 27 Drawing Sheets

Related U.S. Application Data

(60) Provisional application No. 63/050,333, filed on Jul. 10, 2020.

(51) Int. Cl.
  *G06T 7/62* (2017.01)
  *G16H 20/00* (2018.01)
  *G16H 50/20* (2018.01)

(52) U.S. Cl.
  CPC ............. *G16H 20/00* (2018.01); *G16H 50/20* (2018.01); *G06T 2207/20081* (2013.01); *G06T 2207/30036* (2013.01); *G06T 2207/30168* (2013.01)

(58) Field of Classification Search
  CPC . G06T 2207/30168; G06T 2207/20081; G06T 2207/30036
  USPC .......................................................... 382/128
  See application file for complete search history.

(56) References Cited

U.S. PATENT DOCUMENTS

| | | |
|---|---|---|
| 7,292,674 B2 | 11/2007 | Lang |
| 9,033,576 B2 | 5/2015 | Yankelevitz et al. |
| 9,283,061 B2 | 3/2016 | Tank |
| 9,710,603 B2 | 7/2017 | Kaminski et al. |
| 10,074,178 B2 | 9/2018 | Cocco et al. |
| 10,248,883 B2 | 4/2019 | Borovinskih et al. |
| 10,390,913 B2 | 8/2019 | Sabina et al. |
| 10,410,308 B2 | 9/2019 | Abousy et al. |
| 10,482,204 B2 | 11/2019 | Marie et al. |
| 10,937,108 B1 | 3/2021 | Tabak et al. |
| 11,037,671 B2 | 6/2021 | Kaminski et al. |
| 11,055,789 B1 | 7/2021 | Tabak et al. |
| 2001/0052907 A1 | 12/2001 | Mukai et al. |
| 2016/0051348 A1* | 2/2016 | Boerjes .................... A61B 1/24 433/215 |
| 2016/0225151 A1 | 8/2016 | Cocco et al. |
| 2016/0371412 A1 | 12/2016 | Marie et al. |
| 2017/0049311 A1 | 2/2017 | Borovinskih et al. |
| 2019/0192258 A1 | 6/2019 | Kang et al. |
| 2019/0231490 A1 | 8/2019 | Sabina et al. |
| 2019/0295710 A1 | 9/2019 | Kusnoto et al. |
| 2019/0313963 A1 | 10/2019 | Hillen |
| 2019/0326011 A1 | 10/2019 | Crego et al. |
| 2019/0333627 A1 | 10/2019 | Johnson |
| 2020/0085546 A1 | 3/2020 | Li et al. |
| 2021/0074425 A1 | 3/2021 | Carter et al. |
| 2021/0082184 A1 | 3/2021 | Claessen et al. |
| 2021/0118129 A1* | 4/2021 | Kearney .................... G06T 3/40 |
| 2021/0153976 A1* | 5/2021 | Chen ...................... A61C 9/004 |
| 2021/0153986 A1* | 5/2021 | Wirjadi .............. A61C 13/0004 |

* cited by examiner

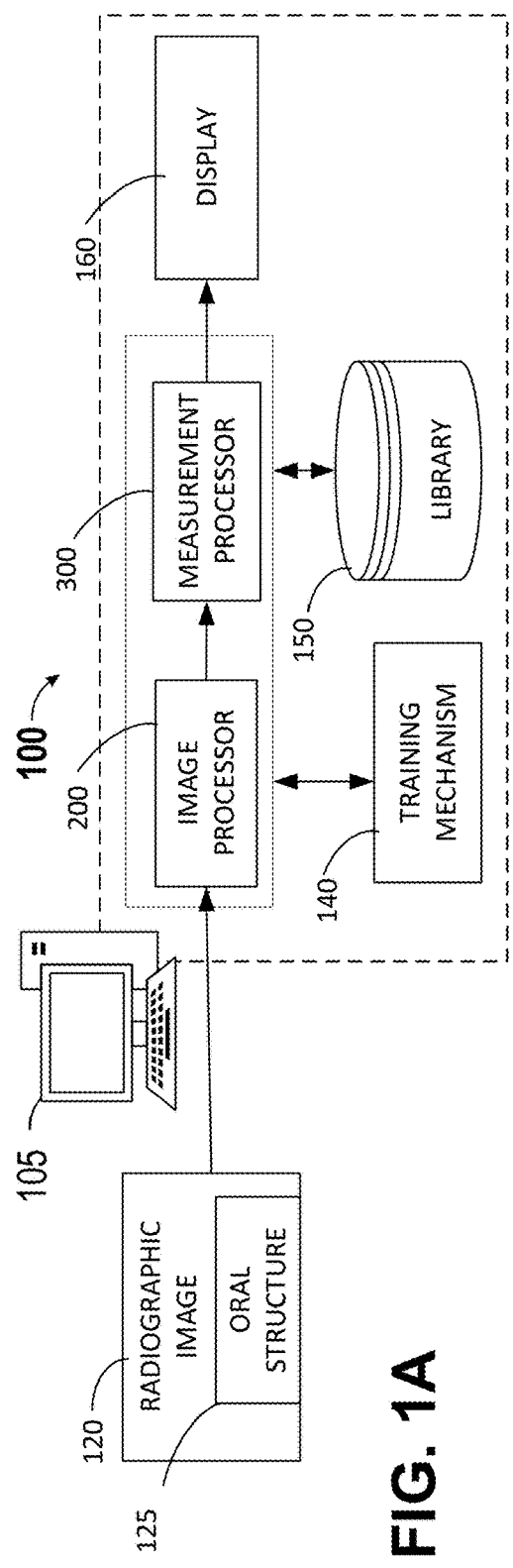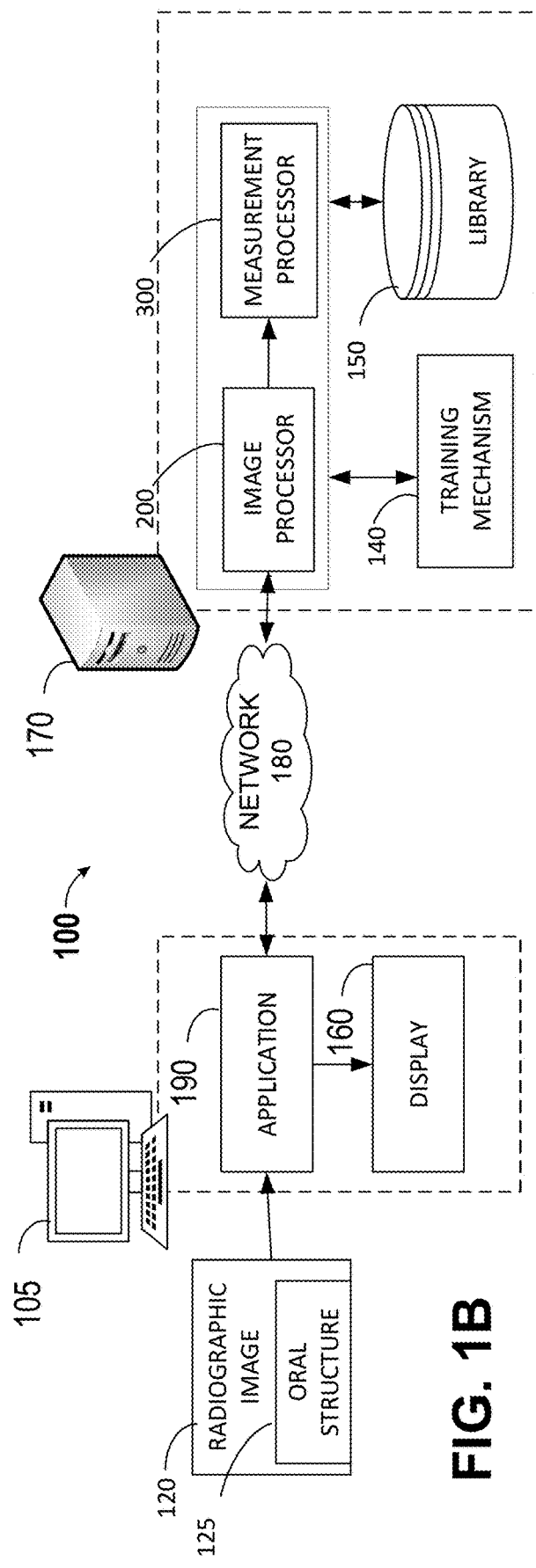
FIG. 1A
FIG. 1B

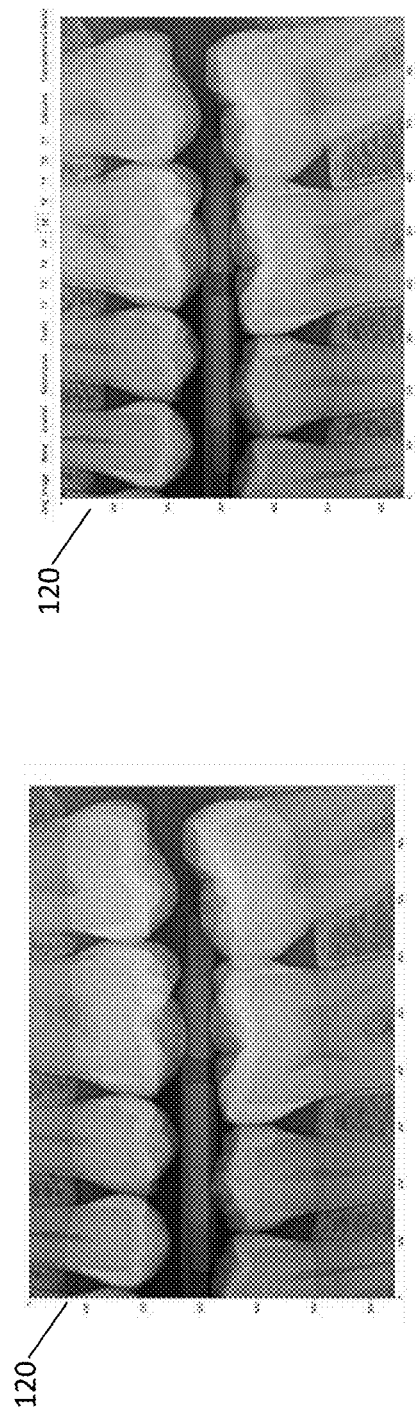
FIG. 4A Bone Mask
FIG. 4B Tooth Number Identification
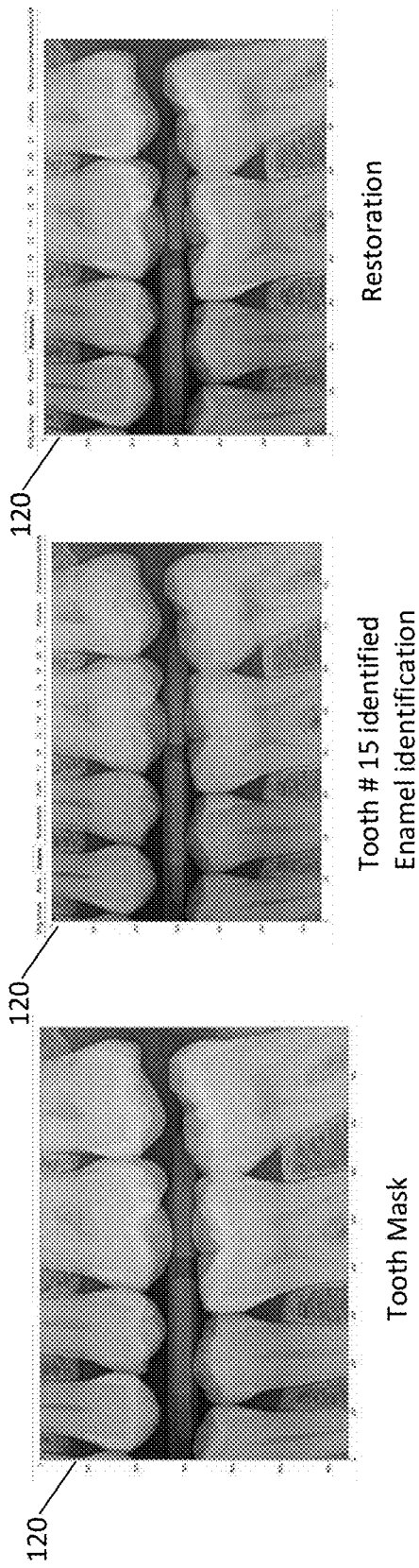
FIG. 4C Tooth Mask
FIG. 4D Tooth #15 identified Enamel identification
FIG. 4E Restoration

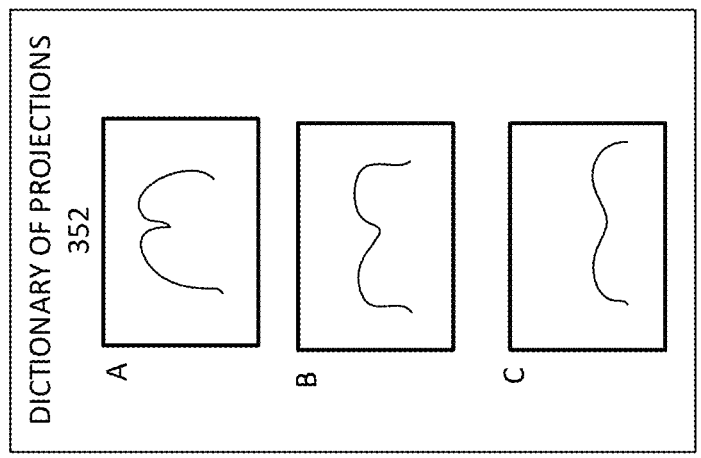
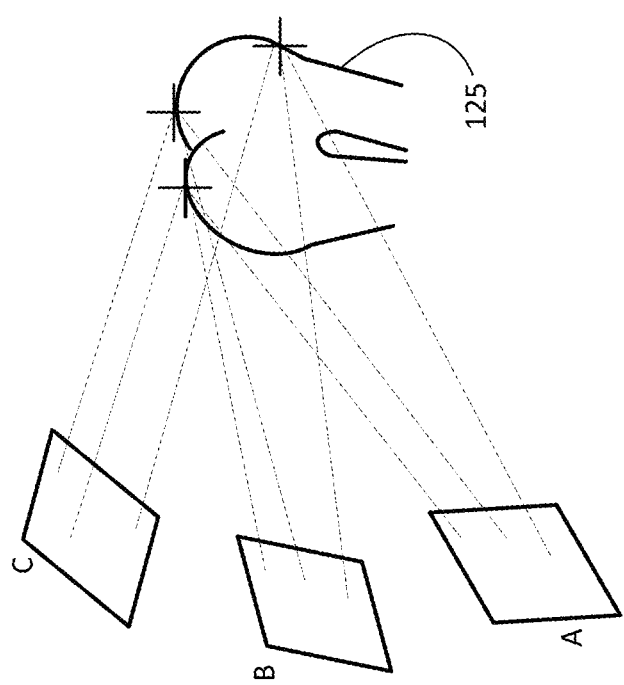
FIG. 10

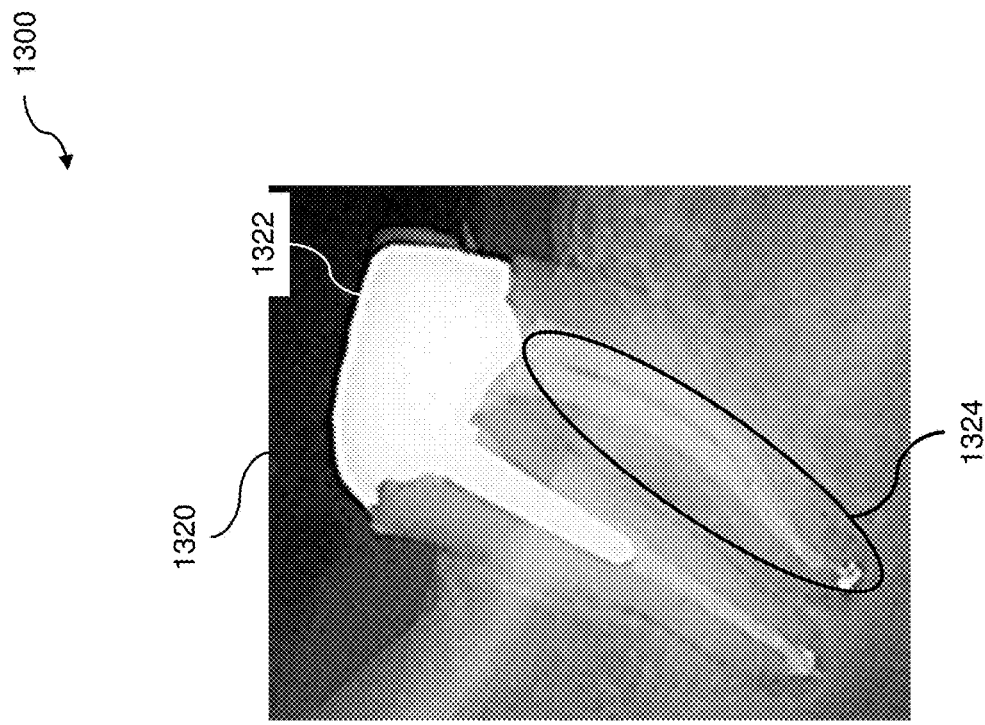
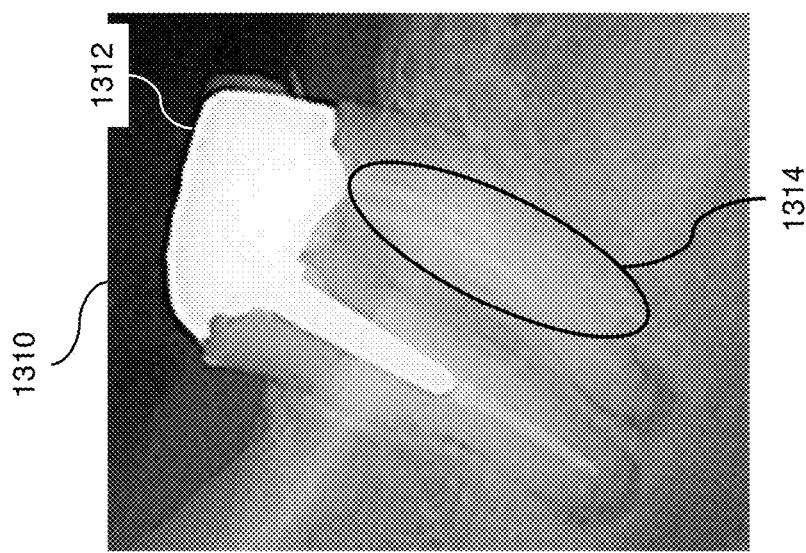
*FIG. 23A*

SYSTEMS AND METHODS FOR INTEGRITY ANALYSIS OF CLINICAL DATA

CROSS-REFERENCE TO RELATED APPLICATIONS

This application is a continuation-in-part (CIP) application of, and claims priority to, U.S. Non-Provisional application Ser. No. 16/752,362, entitled "ESTIMATING MEASUREMENTS OF CRANIOFACIAL STRUCTURES IN DENTAL RADIOGRAPHS" and filed Jan. 24, 2020, and further claims the benefit of, and priority to, U.S. Provisional Application No. 63/050,333, entitled "MULTISYSTEM MACHINE LEARNING FOR UTILIZATION INTEGRITY DETECTION" and filed Jul. 10, 2020, the contents of all of which are herein incorporated by reference in their entireties.

BACKGROUND

Accurately measuring oral structures present on a two-dimensional dental radiograph using currently available image processing methods is problematic. During the process of taking a dental radiograph, an x-ray sensor is positioned in a patient's mouth and an x-ray source is aligned with the sensor outside of the patient's mouth. The term craniofacial structure refers generally to the bones of the skull and face. The term "oral structures" (or "dental structures") refers generally to natural teeth, restorations, implants, and any other structure that relates to craniofacial structures. Measurements of oral structures will typically include the relationship of the oral structure and craniofacial structure. When the x-ray source is activated, x-rays are sent toward the sensor, and any oral structures between the source and the sensor influence the resulting image. When an object is positioned upright and directly in the x-ray source's path, the object will be seen on the final image with minimal distortion. However, if the object's spatial orientation is changed in relation to the source and the sensor, the image of the object will be distorted. In controlled systems, the degree of distortion can be calculated if all angulations of the source, sensor, and object are known. In dentistry, however, the position of a patient's oral structures in relation to the sensor and the source can only be estimated.

To address these issues, external calibration objects have been imaged along with structures of interest to allow for image calibration. This type of calibration is only possible if the calibration object is present at the time that the radiographic image is captured.

Dental radiography is also finding increased use in the area of dental insurance underwriting and fraud detection. Dental insurance payers and care providers deploy multiple, discrete programs within the administrative systems to prevent unnecessary disbursement of clinical services and payment. These discrete programs include Fraud, Waste and Abuse (FWA) programs, clinical utilization review programs, and rule-based claim adjudication engines that check for coordination of benefits and frequency of limitation on payments.

Identifying and preventing FWA is one of the key functions in the benefit payment cycle by dental insurance providers (payers) and large dentals service organizations (DSO) to ensure quality of care. FWA program is a mandatory program for administering and delivering government sponsored health and dental services in the United States. In the current provider-payer payment systems, FWA is commonly identified after paying out a benefit through the claim adjudication process. FWA is detected using advanced analytics through execution of statistical outlier reports on historic data on provider utilization and payment. Fraud is verified by a special investigation unit (SIU) team, actively collecting samples of data and images from clinical practices and comparing the occurrences of fraud based on evidence from radiographic images, chart notes and clinical utilization. This two-step process of detection and verification of FWA is a time consuming, resource intensive and reactive process involving multiple disciplines that span across compliance, legal, clinical, and business.

Clinical utilization review program is a process of reviewing medical necessity for clinical treatments and appropriate payment reimbursements in the provider-payer claim cycle. The selection of providers under clinical review is typically limited to standard clinical procedures that are costly and commonly upcoded or unbundled for submitting a higher-paying service for reimbursement. Execution of a clinical review program requires high skills of clinical expertise with ability to read and interpret radiographs against submitted clinical services.

SUMMARY

The present disclosure relates generally to dental information analysis, including analysis of dental clinical data (also referred to as clinical data) to make a quick (expedited) determination of the reasonableness of a proposed treatment plan submitted by dental-care providers (e.g., as part of a request for treatment pre-approval or as a claim following completion of a dental service). Implementations of dental information analysis described herein also include a comprehensive framework to analyze clinical data and determine the accuracy and/or veracity (integrity level) of the information submitted (for proposed treatment plans and/or claims for completed dental work). The various frameworks described herein may be used in conjunction with image data calibration and standardization approaches, including approaches for estimating measurements of craniofacial structures by analyzing radiographic image data from different imaging modalities.

The dental data analysis solutions discussed below include a multisystem machine learning for clinical data integrity detection. The proposed approaches and solutions described herein include a combined, Fraud, Waste, and Abuse (FWA) detection methodology, and a continuous, on-going clinical review framework that leverages advanced machine learning models deployed across multiple systems in the payment cycle. This proactive process can detect and prevent payments on duplicate services, same submission of images for multiple patients, and can cross-check services with objective evidence of clinical measurements from current and historic radiography and provider chart notes. The embodiments described herein implement machine learning models that include a duplicate detector, image tampering detection, a phantom detector to identify treatments and/or teeth that are not present, and/or inconsistencies in dental history (as it pertains to one or more teeth).

Another approach to facilitate an expedient and reliable analysis, and which can provide dental-care providers with a quick decision regarding a request submitted for an authorization of dental care plan for a patient, is based on determining metrics according to features identifiable from supporting data submitted by the dental-care providers, and assessing the reasonableness of the proposed treatment plans according to the computed metrics. For example, when requesting approval for a treatment plan for a patient, e.g., fitting a crown on a damaged (and potentially vulnerable) tooth, the provider will typically submit radiographic images in support of the treatment plan. The approaches described herein are configured to identify (e.g., via a trained learning machine) various features discernable from the image data, based on which one or more metrics are derived. One such metric may be a ratio of the size (e.g., area, length) of a damaged (or diseased) portion of a tooth relative to another portion that is representative of the overall size of the visible tooth structure (for example the tooth crown area). Once the metric is derived it can be processed by rule-based algorithms and processes to determine if a prosthetic crown fitting is appropriate given the metric computed.

As will also be discussed in greater detail below, this approach too may require an initial calibration procedure to generate calibrated image data that can be more reliably processed by machine learning engines that may have been trained (e.g., to identify various dental features/structures appearing in in the radiographic image data submitted by the provider) according to calibrated (standardized) images that share a common scale and/or viewing perspective. Such calibration can reduce the occurrence of error.

Embodiments described herein may include calibration operations to calibrate source image measurement data to measure the precise distances and sizes on an image. For example, the width or height of a tooth in millimeters or the depth of a decay and so on. The calibration operations seek to convert the pixels in a radiographic image to a standard unit (e.g., pixel-to-millimeter conversion that indicates the width and height of a pixel in millimeters). Thanks to this conversion, regardless of the image quality, actual distances can be accurately estimated (i.e., distances in millimeters between two point in an image remains the same even if the resolution is changed by resizing)

The calibration solutions described herein achieve the calibration of image data without requiring the use of non-dental calibration objects (acting as landmark with known dimensionality), and instead rely on data that may be available such as the sensor brand/model capturing the radiographic image. When the sensor information is not available other intrinsic characteristics of the radiographic images may be used to predict the sensor information. Such data can be used to derive, among other things, viewing angles, scales corresponding to the image data, and positioning information, with such derived data being used to calibrate and/or correct alignment of the image data to increase result accuracy and confidence levels.

Advantages of the embodiments described herein include: 1) generating precise outputs such as area ratios for crown decision, distance (based in part to the calibration procedures), or ratios (cej-bp and cej-apex) for scaling and root planing, 2) deriving decision outcomes (accept, deny, review, downcode, request for more information), 3) handling multiple image and document formats, performing image redaction, removing PHI, 4) generating predictions for intraoral images, 5) generating treatment quality scores (i.e., how well is a treatment performed), 6) performing image quality determination, performing image enhancement, 7) computing prediction trustworthiness/uncertainty (e.g., output such as "good," "okay," "bad" predictions), and 8) deriving provider scores for individual providers, based on duplicate score, manipulation score, tooth/treatment presence score, ratio of quadrants per claim for SRP, etc.

Thus, in some variations, a method for clinical data analysis is provided that includes obtaining dental data for an individual, with the dental data including input radiographic image data for at least one dental object, and identifying, by one or more machine learning models, at least one first dental feature in the input radiographic image data for the at least one dental object, and at least one other feature in the dental object comprising at least partly a healthy dental structure (e.g., a portion of a tooth that is not diseased, restored, or damaged). The method additionally includes computing at least one dimensioned property representative of physical dimensions of the at least one first dental feature and the at least one other feature comprising at least partly the healthy dental structure, deriving based on the at least one dimensioned property at least one dimensioned property ratio indicative of an extent of a dental clinical condition associated with the identified at least one first dental feature of the at least one dental object, and determining a treatment plan based on a comparison of the derived at least one dimensioned property ratio to a respective at least one pre-determined threshold value.

Embodiments of the method may include at least some of the features described in the present disclosure, including one or more of the following features.

Computing at least one dimensioned property may include computing one or more of, for example, areas of the identified at least one first dental feature and the at least one other feature, and/or lengths of the identified at least one first dental feature and the at least one other feature. Deriving the at least one dimensioned property ratio may include one or more of, for example, deriving an area ratio of an area for the at least one first dental feature and area for the at least one other feature, or deriving a length ratio of a length of the at least one first dental feature and a length of the at least one other feature.

The at least one first dental feature may include one or more of, for example, a decaying tooth portion for a tooth, a filling region for the tooth, a restoration, and/or bone loss. The at least one other feature may include a clinical crown structure for the tooth.

Identifying, by the learning machine, the at least one first dental feature and the at least one other feature may include generating masks, by the learning machine, representative of the at least one first dental feature and the at least one other feature comprising at least partly the healthy dental structure.

Determining the treatment plan may include one or more of, for example, automatically determining by machine learning model a proposed treatment plan to treat an abnormal dental feature and/or determining based on the derived dimensioned property ratio whether to approve a dental-care-provider treatment plan submitted by a dental-care provider.

Obtaining the dental data may include receiving source radiographic image data represented according to pixel-based dimensions, and calibrating the source radiographic image data to produce the input radiographic image data represented in terms of estimated standard-unit dimensions, with the source radiographic image data being free of any non-dental calibration objects.

The estimated standard-unit dimensions may include millimeter (mm) units.

Calibrating the source radiographic image data may include selecting a segmenter and/or an object detector, predicting source masks and source points (and/or keypoints) of the at least one dental object appearing in the source radiographic image data using the segmenter and the object detector, providing the source radiographic image data and the image metadata, comprising the source masks and source points, to a calibration process selector, selecting by the calibration process selector at least one measurement process from a set of measurement processes according to the source radiographic image data and the image metadata, deriving a sensor pixel-to-standard-unit ratio using the selected at least one measurement process, and generating the input radiographic image data and resultant calibrated metadata, comprising calibrated masks and points on the dental object, using calibrated measurements of the at least one dental object based on the sensor pixel-to-standard-unit ratio and the image metadata.

Deriving the sensor pixel-to-standard-unit ratio using the selected at least one measurement process may include determining a sensor type for the source radiographic image data, determining sensor characteristics based on the determined sensor type, determining pixel dimensions for the source radiographic image data, and deriving the sensor pixel-to-standard-unit ratio based on the determined sensor characteristics and the determined pixel dimensions for the source radiographic image data.

Deriving the sensor pixel-to-standard-unit ratio using the selected at least one measurement process may include identifying from the source radiographic image data teeth without restorations, determining distances in pixels between mesial and distal Cemento Enamel Junction (CEJ) points for the identified teeth, deriving a plurality of pixel-to-standard-unit ratios using the determined distances in pixels and based on pre-determined standard average distances between the mesial and distal CEJ points for each of the identified teeth, and computing an average pixel-to-standard-unit ratio from the derived plurality of pixel-to-standard-unit ratios.

Deriving a sensor pixel-to-standard-unit ratio using the selected at least one measurement process may include determining one or more outer borders for respective one or more dental objects appearing in the source radiographic image data, comparing the one or more outer borders to 2D projections in a projection dictionary, the 2D projections being at incremental distance and angles generated from 3D dental image data, to identify a match between the one or more outer borders and the 2D projections in the projection dictionary, estimating a viewing angle at which the source radiographic image data was obtained based on the identified match between the one or more outer borders and the 2D projections in the projection dictionary, and deriving the sensor pixel-to-standard-unit ratio based on the estimated angle at which the source radiographic image data was obtained.

Deriving a sensor pixel-to-standard-unit ratio using the selected at least one measurement process may include detecting an implant structure appearing in the source radiographic image data, determining implant attributes based on the source radiographic image data for the detected implant structure, comparing the determined implant attributes for the detected implant structure to stored implant attributes included in implant data records, maintained in an implant structure database, for known manufactured implants to identify a match between the determined implant attributes and the stored implant attributes included in the stored implant data records, and deriving the sensor pixel-to-standard-unit ratio based on stored geometrical information associated with a selected one of the implant data records that most closely matches the implant attributes determined from the source radiographic image data.

Deriving a sensor pixel-to-standard-unit ratio using the selected at least one measurement process may include detecting an implant structure appearing in the source radiographic image data, determining implant attributes, based on the source radiographic image data for the detected implant structure, comparing the determined implant attributes for the detected implant structure to stored implant attributes included in implant data records, maintained in an implant structure database, for known manufactured implants to identify a match between the determined implant attributes and the stored implant attributes included in the stored implant data records, determining an outer border for the detected implant structure appearing in the source radiographic image data, comparing the outer border to 2D projections maintained in a projection dictionary, the 2D projections being at incremental distance and angles generated from 3D dental image data, to identify a match between the outer border and the 2D projections in the projection dictionary, estimating a viewing angle at which the source radiographic image data was obtained based on the identified match between the outer border and the 2D projections in the projection dictionary, and deriving the sensor pixel-to-standard-unit ratio based on the estimated angle at which the source radiographic image data was obtained, and based on stored geometrical information associated with a selected one of the implant data records that most closely matches the implant attributes determined from the source radiographic image data.

Deriving the sensor pixel-to-standard-unit ratio may include estimating viewing angles for other dental objects detected in the source radiographic image data based on a position of the implant structure relative to the other dental structure and based on the viewing angle at which the source radiographic image data was obtained, and deriving the sensor pixel-to-standard-unit ratio based on the estimated viewing angles for the other dental structures detected in the source radiographic image data, and based on the stored geometrical information associated with the selected one of the implant data records that most closely matches the implant attributes determined from the source radiographic image data.

In some variations, a system for clinical data analysis is provided that includes a communication interface to obtain dental data for an individual, wherein the dental data comprises input radiographic image data for at least one dental object, one or more memory devices, and one or more processor-based devices, coupled to the communication interface and to the one or more memory devices. The one or more processor-based devices are configured to identify, by one or more machine learning models, at least one first dental feature in the input radiographic image data for the at least one dental object, and at least one other feature in the dental object comprising at least partly a healthy dental structure, compute at least one dimensioned property representative of physical dimensions of the at least one first dental feature and the at least one other feature comprising at least partly the healthy dental structure, derive based on the at least one dimensioned property at least one dimensioned property ratio indicative of an extent of a dental clinical condition associated with the identified at least one first dental feature of the at least one dental object, and determine a treatment plan based on a comparison of the derived at least one dimensioned property ratio to a respective at least one pre-determined threshold value.

In some variations, a non-transitory computer readable media is provided, storing a set of instructions, executable on at least one programmable device, to obtain dental data for an individual, wherein the dental data comprises input radiographic image data for at least one dental object, and identify, by one or more machine learning models, at least one first dental feature in the input radiographic image data for the at least one dental object, and at least one other feature in the dental object comprising at least partly a healthy dental structure. The computer readable media include further instructions to compute at least one dimensioned property representative of physical dimensions of the at least one first dental feature and the at least one other feature comprising at least partly the healthy dental structure, derive based on the at least one dimensioned property at least one dimensioned property ratio indicative of an extent of a dental clinical condition associated with the identified at least one first dental feature of the at least one dental object, and determine a treatment plan based on a comparison of the derived at least one dimensioned property ratio to a respective at least one pre-determined threshold value.

Embodiments of the system and the computer-readable media may include at least some of the features described in the present disclosure, including at least some of the features described above in relation to the method.

In some variations, another method for dental data analysis is provided that includes obtaining by a computing system dental data for an individual, the dental data comprising input radiographic image data of at least one dental object, and treatment data representative of one or more treatment procedures associated with the at least one dental object, analyzing, by one or more machine learning models implemented by the computing system, the input radiographic image data to identify one or more dental features associated with the at least one dental object, and deriving, by the computing system, based on the treatment data and the identified one or more dental features associated with the at least one dental object, one or more integrity scores for the input radiographic image data and the treatment data, with the one or more integrity scores being representative of potential integrity problems associated with the input radiographic image data and the treatment data. Deriving the one or more integrity scores includes deriving a provider score representative of a potential integrity problem associated with a dental-care provider submitting the treatment data.

Deriving the provider score may include computing an outlier score representative of a level of deviation between a treatment plan, specified in the treatment data for the at least one dental object to remedy a dental condition identified in the treatment data for the individual, and treatment plans to treat similar dental conditions associated with archived treatment data and archived radiographic image data for a plurality of other individuals.

Deriving the provider score may include determining, by the computing system, one or more possible treatment plans to remedy a dental condition identified in the treatment data for the individual, and computing an aggressiveness score representative of a complexity level difference between a specified treatment plan submitted by the dental-care provider to remedy the dental condition and the determined one or more possible treatment plans.

Deriving the provider score may include computing a phantom disease score representative of a level of consistency between a treatment plan specified in the treatment data for the at least one dental object to remedy a dental condition identified in the treatment data for the individual, and identified features of the input radiographic image data detected by the computing system.

Computing the phantom disease score may include one or more of, for example, performing image manipulation detection on the input radiographic image data to determine whether a portion of the input radiographic image data was modified, and/or determining, based on future image data, that the treatment was never performed.

Computing the phantom disease score performing a duplicate or near-duplicate image detection on the input radiographic image data to determine whether a portion of the input radiographic image data, relating to identified dental condition for the at least one dental object, fully or substantially matches a portion of a previously stored radiographic image.

Deriving the provider score may include computing, based on the treatment data associated with the input radiographic image data for the individual, and based on archived treatment data for one or more individuals treated by the dental-care provider, a phantom treatment score representative of extent to which the dental-care provider submits treatment plans inconsistent with associated dental conditions identified form the treatment data for the individual and from the archived treatment data.

Deriving the one or more integrity scores may include identifying, by at least one of the one or more machine learning models, at least one first dental feature in the input radiographic image data for the at least one dental object, and at least one other feature in the dental object comprising at least partly a healthy dental structure, computing at least one dimensioned property representative of physical dimensions of the at least one first dental feature and the at least one other feature comprising at least partly the healthy dental structure, and deriving based on the at least one dimensioned property at least one dimensioned property ratio indicative of an extent of a dental clinical condition associated with the identified at least one dental feature of the at least one dental object. The dimension property ratio(s) can be used (e.g., using rules that are based on comparisons to respective pre-determined threshold/reference values) a treatment plan (e.g., either an actual recommended treatment plan, or a decision about whether to accept or reject, or take some other action, with respect to a proposed treatment plan).

Analyzing the input radiographic image data may include detecting anomalous features in the input radiographic image data, including determining one or more of, for example, whether a portion of the input radiographic image data substantially matches a portion of a previously stored radiographic image, and/or whether a portion of the input radiographic image data was modified.

In some variations, another system for dental data analysis is provided that includes a communication interface to obtain dental data for an individual, the dental data comprising input radiographic image data of at least one dental object, and treatment data representative of one or more treatment procedures associated with the at least one dental object, one or more memory devices, and one or more processor-based devices, coupled to the communication interface and to the one or more memory devices. The one or more processor-based devices are configured to analyze, by one or more machine learning models implemented by the computing system, the input radiographic image data to identify one or more dental features associated with the at least one dental object, and derive, by the computing system, based on the treatment data and the identified one or more dental features associated with the at least one dental object, one or more integrity scores for the input radiographic image data and the treatment data, with the one or more integrity scores being representative of potential integrity problems associated with the input radiographic image data and the treatment data. The one or more processor-based devices configured to derive the one or more integrity scores are configured to derive a provider score representative of a potential integrity problem associated with a dental-care provider submitting the treatment data.

In some variations, another non-transitory computer readable media is provided that stores a set of instructions, executable on at least one programmable device, to obtain by a computing system dental data for an individual, the dental data comprising input radiographic image data of at least one dental object, and treatment data representative of one or more treatment procedures associated with the at least one dental object, analyze, by one or more machine learning models implemented by the computing system, the input radiographic image data to identify one or more dental features associated with the at least one dental object, and derive, by the computing system, based on the treatment data and the identified one or more dental features associated with the at least one dental object, one or more integrity scores for the input radiographic image data and the treatment data, with the one or more integrity scores being representative of potential integrity problems associated with the input radiographic image data and the treatment data. The instructions to derive the one or more integrity scores include one or more instructions to derive a provider score representative of a potential integrity problem associated with a dental-care provider submitting the treatment data.

Embodiments of the other system and the other computer-readable media may include at least some of the features described in the present disclosure, including at least some of the features described above in relation to the methods, the first system, and the first computer-readable media.

Any of the above variations of the methods, systems, and/or computer-readable media, may be combined with any of the features of any other of the variations of the methods, systems, and computer-readable media described herein.

Other features and advantages of the invention are apparent from the following description, and from the claims.

BRIEF DESCRIPTION OF THE DRAWINGS

These and other aspects will now be described in detail with reference to the following drawings.

FIGS. 1A-1B depict example systems for performing calibration and data analysis processes.

FIGS. 4A-4E are examples of predicted masks and points that may be provided by the image processor.

FIG. 10 illustrates the projection of a 3D (three-dimensional) surface onto a plane at incremental angles to generate a dictionary of projections.

FIG. 23A shows a manipulated x-ray image.

Like reference symbols in the various drawings indicate like elements.

DESCRIPTION

Figure 2:
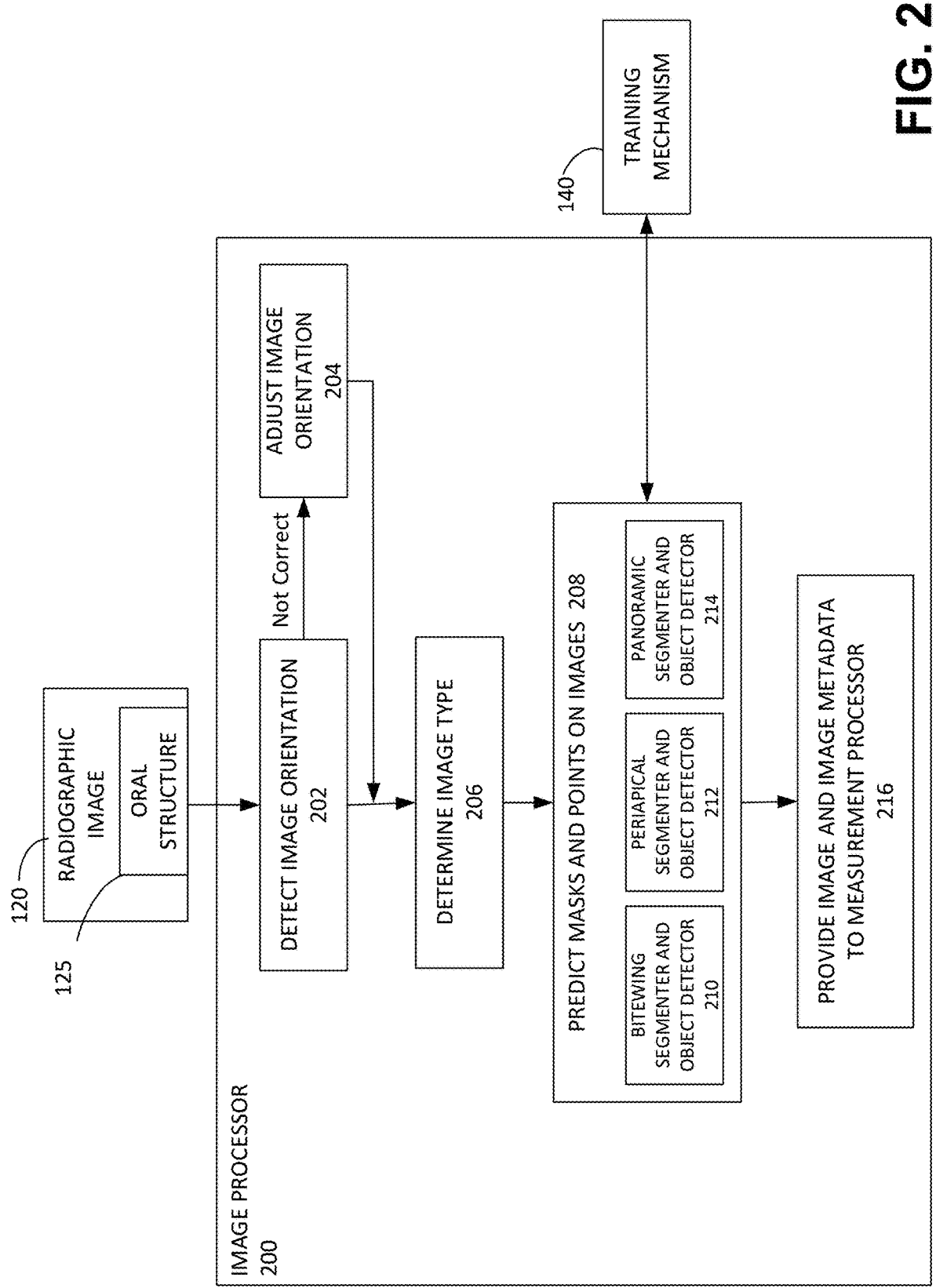
FIG. 2 is a flow diagram depicting an example method for an image processor for determining optionally image orientation and image type, predicting masks and points on images, and providing image and image metadata.

The present disclosure discusses various techniques and approaches for analyzing data submitted, for example, by dental care providers, in order to assess the veracity of such submitted data in order to identify erroneous or suspicious data, and to assess in an expedient and reliable manner, the reasonableness/appropriateness of treatments plans submitted by the dental care providers (i.e., assess their medical necessity). Data submitted by providers may include errors (which may have resulted from innocent oversights, due to the indication of improper codes, or the inclusion of incorrect supporting data), or may be indicative of attempts to either recover money for fraudulent treatment plans, or attempts to bill (or receive pre-authorization) for improper or unnecessary treatment plans. The analysis performed by the implementations described herein is generally performed by processing, using machine learning engines, clinical/treatment data (also referred to as clinical data) from providers (which includes descriptive data, possibly provided using natural language descriptions, or charts or by standardized codes and pre-determined text-based descriptions that are available in lists/libraries of descriptive data) and supporting dental image data (in the form of dental photographs and radiographic image data).

As will be discussed in greater detail below, the implementations described herein are configured to handle input data from numerous different sources (e.g., different dental-care providers, submitting claims and pre-authorization requests to different insurance companies using different claim processing and review procedures). In most situations, the standard-unit distances may not be provided by the provider, and consequently the payers (such as insurance companies) can only crudely estimate the standard-unit distances within the x-rays (eyeballing them). To quantify the measurements on a radiographic image, the standard-unit dimensions of it need to be determined. In order to ensure that the learning machine models implemented for the various engines can provide consistent and accurate output data no matter the submitting source (where each source, namely each individual dental provider, may provide image data captured using different equipment, and under different image-viewing conditions), a calibration procedure may be used, at least in some embodiments, to measure image data that has a substantially uniform scale, and/or may have a substantially uniform viewing perspective. For this to measurement, calibration is based on other sources of information, which may include previously captured dental image data for a particular patient for whom a claim or a pre-authorization request is being submitted, archives of image data for multiple patients (which may be grouped according to the dental-care providers treating them), data repositories of technical and performance specifications of the imaging equipment (sensors) being used to capture image data, etc.

As will further be discussed in greater detail below, the present disclosure describes approaches for performing a quick (expedited) clinical data analysis (and, in some embodiments, provides responses/answers within a few seconds or a few minutes from receipt of request data) that assesses whether treatment plans submitted by dental-care providers are reasonable and/or proper in view of the supporting materials accompanying the requests (e.g., the so-called clinical data). In some examples, the analysis may be performed by deriving metrics based on computation of size (e.g., area) of dental features identified (e.g., by a machine learning engine) in dental images. An example of a dental metric that can be used is an area ratio value computed as a ratio of the area of a diseased (damaged) portion of a tooth (that is to be treated) relative to the overall size (e.g., area) of the tooth (as may be represented by the clinical crown portion constituting the tooth structure). It is to be noted that because such a metric is a ratio (and thus is a scalar value that does not necessarily depend on absolute size of the measured features), this clinical data analysis could be completed without necessarily needing to first calibrate (or standardize) the input image data (this can reduce the computational effort and yield results more quickly than in the situation where calibration is first performed).

The present disclosure also discusses a comprehensive framework for determining data integrity of dental data submitted by providers, so as to detect oversight errors from the submitting sources, detect potential attempts to bill for medically unnecessary dental procedures, and detect outright attempts at fraud (by submitting manipulated/doctored images, or by submitting images obtained from different patients, etc.) Because this framework, as will be discussed in greater detail below, leverages archived image data for the patient for whom a claim or pre-approval request is being submitted, and multitude of other patients, the framework may, in some examples, require calibration of radiographic image data (according to, for examples, the techniques and approaches described herein, i.e., without requiring that calibration objects be used.

The present disclosure is organized as follows. First, the particulars of the proposed calibration procedures (which may be used in conjunction with the data processing and analysis frameworks) will be described. Next, a proposed approach for analyzing clinical data according to metrics derived from the areas of features identified in the radiographic images will be described. Lastly, a comprehensive framework for utilization integrity and fraud detection (leveraging archival patients' dental data, and data regarding dental providers' historical behavior vis-à-vis submission of claims) is described.

Dental Image Data Calibration and Measurement Estimation

The present disclosure describes calibrations/standardization implementations that are free of foreign (non-dental) calibration objects, and are configured to estimate measurements (resulting in calibrated/standardized image data) using, for example, a patient's unique anatomical oral structures as calibration objects without the need for an external calibration object. Additionally, the proposed approaches can calculate the angle between a patient's oral structures and the x-ray source and sensor, when 3-dimensional measurements of structures featured in the produced radiographic images are available.

Benefits and advantages provided by such implementations can include, but are not limited to, a technical solution to the technical problems of using a patient's unique anatomical oral structures as calibration objects to make calibrated measurements without the need for an external calibration object. Technical solutions and implementations provided herein optimize the process of obtaining calibrated measurements of oral structures featured in 2D dental radiographs. The benefits and advantages provided by these technology-based solutions yield more user-friendly applications, increased accuracy and increased system and user efficiency.

The methods, systems, and other implementations described herein may include, or otherwise make use of, a trained machine-learning model to identify contents related to input data. Machine learning (ML) generally involves various models, algorithms, and processes that allow a computing machine to automatically learn/adapt over time to optimize its performance. The machine learning approaches can be based on optimization processes that can be employed to predict events, classify entities, diagnose problems, and model function approximations. As an example, a system can be trained using data generated by a ML model in order to identify patterns in dental radiographs. Such determinations may be made following the accumulation, review, and/or analysis of user data from a large number of users over time as well as individual patient data, that may be configured to provide the proposed ML approaches with an initial or ongoing training set. In addition, in some implementations, supplemental training data may be intermittently provided to fine-tune or increase the effectiveness of the machine learning model implemented by the machine learning system.

In different implementations, a training system may be used that includes an initial ML model (which may be referred to as an "ML model trainer") configured to generate a subsequent trained ML model from training data obtained from a training data repository or from device-generated data. The generation of this ML model may be referred to as "training" or "learning." The training system may include and/or have access to substantial computation resources for training, such as a cloud, including computer server systems adapted for machine learning training. In some implementations, the ML model trainer is configured to automatically generate multiple different ML models from the same or similar training data for comparison. For example, different underlying ML algorithms may be trained, such as, but not limited to, decision trees, random decision forests, neural networks, deep learning (for example, convolutional neural networks), support vector machines, regression (for example, support vector regression, Bayesian linear regression, or Gaussian process regression). As another example, size or complexity of a model may be varied between different ML models, such as a maximum depth for decision trees, or a number and/or size of hidden layers in a convolutional neural network. As another example, different training approaches may be used for training different ML models, such as, but not limited to, selection of training, validation, and test sets of training data, ordering and/or weighting of training data items, or numbers of training iterations. One or more of the resulting multiple trained ML models may be selected based on factors such as, but not limited to, accuracy, computational efficiency, and/or power efficiency. In some implementations, a single trained ML model may be produced. It is to be noted that in some situations, processes such as optical character recognition (OCR) may be used in combination with ML models. For example, OCR may be used for extracting text from images and then using it in conjunction with ML models (e.g., to identify/detect tooth clinical crowns). In some embodiments, the ML training system may also be configured to generate training data using generative adversarial networks (GANs, as further discussed below in greater detail), improve display of images on the front end, and/or improve processing of images for subsequent models by eliminating noise.

The training data may be continually updated, and one or more of the models used by the system can be revised or regenerated to reflect the updates to the training data. Over time, the training system (whether stored remotely, locally, or both) can be configured to receive and accumulate more and more training data items, thereby increasing the amount and variety of training data available for ML model training, resulting in increased accuracy, effectiveness, and robustness of trained ML models.

FIG. 1A illustrates an example system 100 upon which aspects of this disclosure may be implemented. The system 100 may include a computing platform (e.g., a personal computer) 105 executing software that implements an image processor 200 (e.g., implemented as a ML model) which is coupled to receive a radiographic image 120 containing an oral structure 125 that could comprise a natural tooth, an implant, a restoration, etc., that further relates to craniofacial structures such as bones. The image processor 200 provides output, such as image metadata (e.g., detected features that appear in the image, and their corresponding labels) to a measurement processor 300 which in turn provides calibrated output (a calibrated measurement) based on the image metadata and data from a library 150 that may include an X-ray sensor database, an implant database, a population based anatomical averages database, and a patient specific database, as more particularly described below.

A training mechanism 140 provides a machine-learning based training mechanism, as mentioned above, for training aspects of the image processor 200 for generating (predicting), masks, labels, features and points of the oral structure 125 (e.g., identifying features with text-based identifiers, marking certain features with outlines, representing features as geometric shapes, etc.) A display 160 presents/renders a graphical user interface (GUI) for displaying the calibrated measurement. The specific masks that the ML model implements for the image processor may depend on the specific measurement calibration process that is applied to the image to determine the scale that is to be used (e.g., determine the pixel-to-millimeter ratio for the imager). It is to be noted that in some situations only bone levels need measurement in mm, whereas ratio-based calculations (including area calculations), could be performed in the pixel space.

As will be discussed in greater detail below, those measurement processes include, for example, the known sensor measurement process, the oral structure measurement process, the 3D surface data measurement process, the known implant measurement process, and/or the implant angle measurement process.

In some embodiments, the training mechanism 140 (also referred to a learning engine controller/adapter) is configured to determine and/or adapt the parameters (e.g., neural network weights) of the learning engine that would produce output representative of masks and representation of detected dental objects and features appearing in the image data. To train the ML-based image processor 200, training data comprising masks, labels, or other representations (collectively referred to as training output data) is provided to the training mechanism 140. The training output data thus defines samples of the ground truth that are used to train the ML-based image processor 200 (offline and/or during runtime). This training data may be used to define the parameter values (weights, represented as the vector $\theta$) assigned to links of, for example, a neural network implementation of the machine learning engine. The weight values may be determined, for example, according to a procedure minimizing a loss metric between predictions made by the neural network in response to the underlying image data provided to the ML-engine of the image processor, and the masks, labels, or other output representations of the training data (e.g., using a stochastic gradient descent procedure to minimize the loss metric). The computed parameter values can then be stored at a memory storage device (not shown) coupled to the image processor 200 and/or to the training mechanism 140. After a learning-engine based implementation of the image processor 200 has become operational (following the training stage) and can process actual runtime data, subsequent run-time training may be intermittently performed (at regular or irregular periods) to dynamically adapt the image processor to new, more recent training data samples, and to newer model architectures and data label groupings, in order to maintain or even improve the performance of the image processor 200.

FIG. 1B illustrates an alternative embodiment of the example system 100 upon which aspects of this disclosure may be implemented as a web service, including the computer 105 operating as a client device for executing client application 190 software that is coupled to receive the radiographic image 120 containing the oral structure 125 that could comprise a natural tooth, an implant, a restoration, etc. A server 170 runs a server-side application such as in a cloud service executing software that communicates with the application 190 via a network 180 to receive the radiographic image 120. Server 170 executes software for implementing the image processor 200 that provides image metadata to the measurement processor 300, which in turn provides a calibrated measurement based on the image metadata and data from the library 150 that may include an X-ray sensor database, an implant database, a population based anatomical averages database, and a patient specific database. The training mechanism 140 provides a machine-learning based training mechanism for training aspects of the image processor for better predicting masks and points of the oral structure 125. The display 160, as part of the application 190, presents or renders the display of a graphical user interface (GUI) for displaying the calibrated measurement received from the server 170.

FIG. 2 depicts the operation of the image processor 200 that receives the radiographic image 120 containing oral structure 125. An initial transformation step that converts images to a standard format such as JPEG or PNG may be required. At step 202, the image orientation is optionally detected, if the image orientation is not correct, the orientation is optionally adjusted at step 204. Steps 202-206 may optionally be performed by the image processor 200. When processed by insurance related data analysis system, the procedure depicted in FIG. 2 may also include image extraction/cropping operations performed on image data attachments.

Figure 3A:
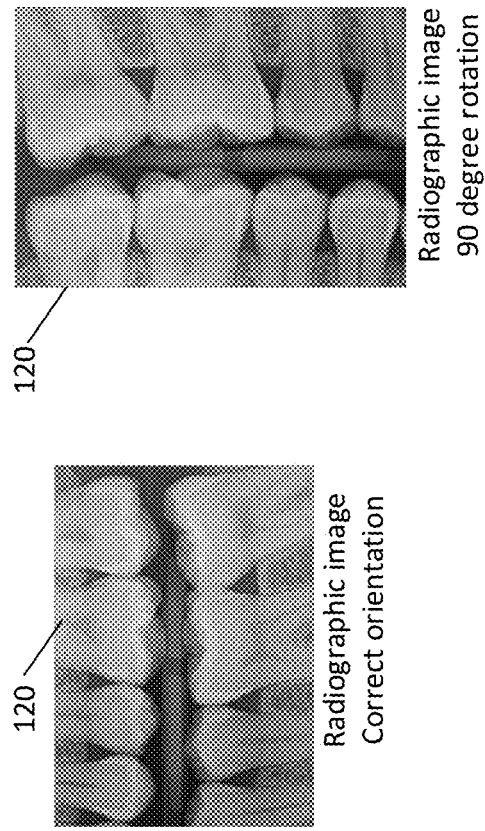
FIGS. 3A-3B are examples of radiographic image types detected by the image processor.
Figure 3B:
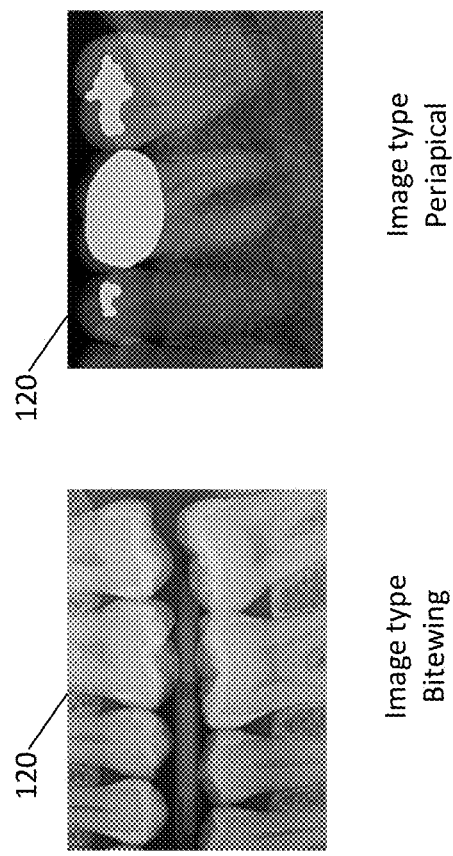

FIG. 3A depicts an example of the radiographic image 120 at a correct orientation and at a 90-degree rotation that would require adjustment. At step 206, an image type for the radiographic image 120 is optionally determined. FIG. 3B depicts the radiographic image 120 with example image types that include bitewing and periapical, among others.

Referring back to FIG. 2, in step 208, masks and points on the radiographic image 120 are predicted by a segmenter and object detector. Depending on the image type as determined in step 206, appropriate pairs of segmenters and object detectors are chosen from a set of segmenters and object detectors 210-214, including selecting among Bitewing Segmenter and Object Detector 210 (in response to the image type being determined, at 206, to be a bitewing image type), Periapical Segmenter and Object Detector 212 (in response to the image type being determined, at 206, to be a periapical image type), and Panoramic Segmenter and Object Detector 214 (in response to the image type being determined, at 206, to be a panoramic image type) in order to provide the desired masks and points prediction. The Bitewing Segmenter and Object Detector 210, Periapical Segmenter and Object Detector 212, and Panoramic Segmenter and Object Detector 214 may use different Deep Learning (DL) based ML models for prediction. For example, bitewing specialized anatomy training models may be used to achieve better prediction (e.g., better labelling) of bitewing images. The selected DL model may predict masks for many labels such as tooth number, general tooth area, bone, enamel, restorations such as crown, filling/inlay, onlay, bridge, implants etc. The DL model itself may be an amalgam of several detection architectures (implementing multiple DL models that are combined to provide meaningful results). The best model identified with the help of metrics such as Intersection over Union (IoU) and bone level (distance between Cemento Enamel Junction (CEJ) and bone point) against a test set is chosen for the particular label. Further, the model may also directly predict the CEJ, and alveolar bone crest (hereafter called bone) points per tooth number. The model provides two ways of getting CEJ and bone points, which can be used to improve the confidence of the measurements. The masks and points are both in terms of pixel measurements. It is to be noted that any number of different image types coupled with an appropriate segmenter and object detector may be employed as desirable. The training mechanism 140 provides for training the ML models for the Bitewing Segmenter and Object Detector 210, the Periapical Segmenter and Object Detector 212, and the Panoramic Segmenter and Object Detector 214 in order to provide the mask and points prediction. The ML models may alios include semantic segmentation, instance segmentation, object detection, keypoint detection, etc.

FIG. 4A-4E depict various non-limiting examples of the masks and points that may be handled by the Segmenter and Object Detectors 210-214 for the oral structures 125 in the radiographic image 120, including the Bone Mask, Tooth Number Identification, Tooth Mask, Enamel Identification, and Restorations. Turning back to FIG. 2, in step 216, the radiographic image 120 and image metadata comprising the image type and associated masks (as determined by the image processor 200) and points are provided to the measurement processor 300 for further processing that includes measurement estimation and calibration.

Figure 5:
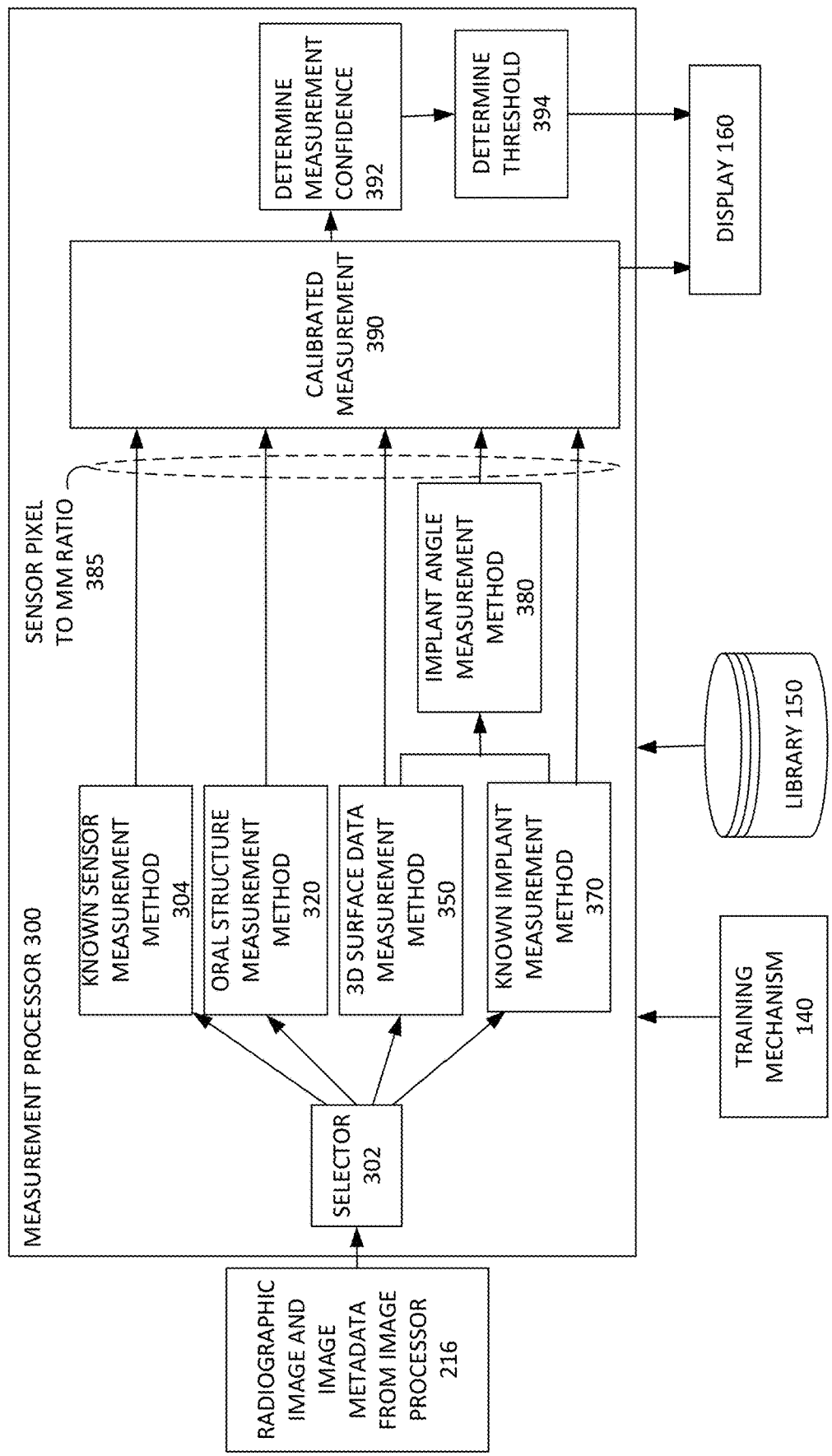
FIG. 5 is a flow diagram depicting a measurement processor that determines a sensor pixel to mm (millimeter) ratio by selecting from at least one measurement method, and provides a calibrated measurement and a threshold.

FIG. 5 depicts the flow diagram and operation of the measurement processor 300 shown in FIG. 1. As illustrated, the measurement processor 300 receives the radiographic image 120 and the image metadata from the image processor 200. The radiographic image 120 and image metadata (including masks, labels, segmented representations, etc.) provide measurements in terms of pixels that require calibration via selection of one or more of methods 304, 320, 350, 370, and 380 by a selector 302 to obtain a sensor pixel to mm (millimeter) ratio 385 (it is to be noted that other unit lengths may be used to establish other calibration ratios). Selector 302 may operate according to a set of rules that determine which of the methods 304, 320, 350, 370, and 380 are selected. If the image metadata includes a known sensor type or a sensor type that can be determined, then the Known Sensor Measurement Method 304 is selected. If the image metadata does not include a known sensor type or the sensor type cannot be determined, then the Oral Structure Measurement Method 320 is selected. If 3D surface data measurement data is available, such as from a library 150 (depicted in FIG. 1, and which is configured to store archived medical/dental data for the particular patient associated with the radiographic image 120, and store archived dental/medical data for other patients), then 3D Surface Data Measurement Method 350 is selected. If the image metadata includes a known implant as part of the image metadata, then the Known Implant Measurement Method 370 is selected. Further, if both 3D surface data measurements are available along with known implant measurement data from methods 350 and 370, then Implant Angle Measurement Method 380 can also be chosen to obtain the (generally) most accurate measurement. Based on radiographic image 120 and the image metadata from image processor 200, in combination with calibration measurement 390, the measurement confidence level 392 can be determined along with a threshold 394. The calibrated measurement 390 along with threshold 394 can subsequently be provided to the display 160 as part of a user interface, and communicated to downstream modules such as a utilization integrity detector and/or a fraud detector. The detailed operation of methods 304, 320, 350, 370 and 380 is explained in further detail below in FIGS. 6-12.

An alternative embodiment of selector 302 includes a machine learning implementation in which any of various combinations of the measurement methods 304, 320, 350, 370, and 380 can be selected according to optimization techniques that provide for calibrated measurement and may be optimized for measurement speed, accuracy, or threshold as desired using ML as provided by the training mechanism 140. The machine learning model may be based on specific patient characteristics as well as crowdsourced methods that provide for overall measurement techniques.

Figure 6:
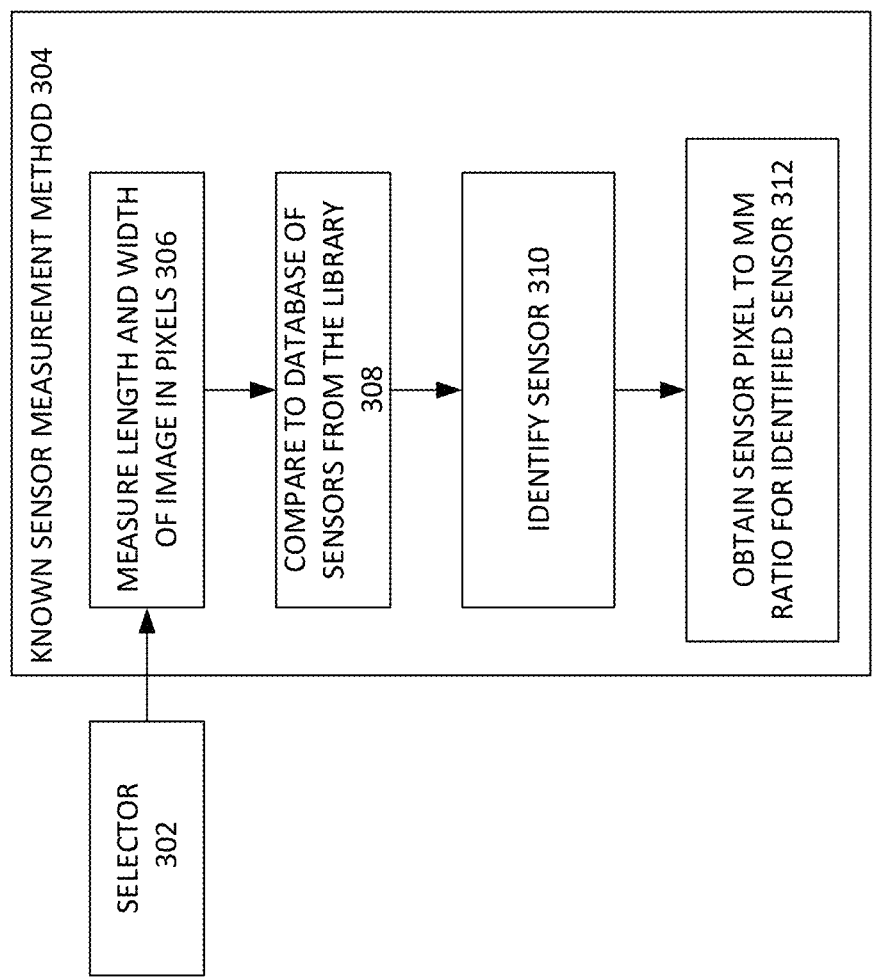
FIG. 6 is a flow diagram depicting a first measurement method implemented by the measurement processor of FIG. 5 for obtaining sensor pixel to mm ratio when the sensor can be determined.

FIG. 6 depicts a flow diagram for the Known Sensor Measurement Method 304 (performed in response to selection of that process by the selector 302). In situations where the radiographic image metadata includes a known sensor type or a sensor type can otherwise be determined from information contained in the library 150 (which may include known sensor types), the length and width measurements of the input image are measured in pixels (in step 306). In step 308, the length and width are compared to a database of sensors from the library 150 and from that comparison, the sensor is identified (at 312). Once the sensor has been identified, the sensor pixel to mm (millimeter) ratio for the sensor can be provided (at 312) according to the database of sensors from the library.

Figure 7:
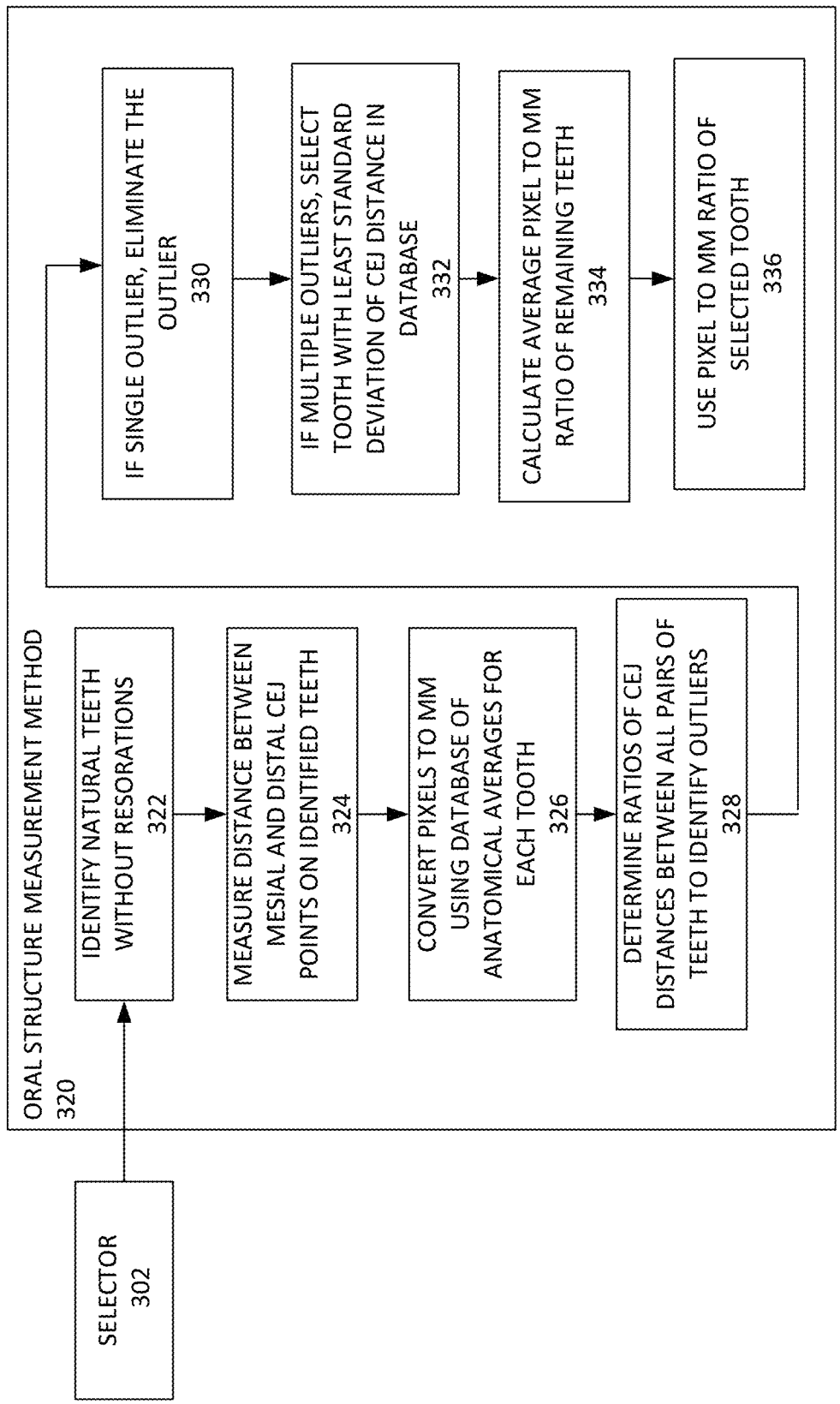
FIG. 7 is a flow diagram depicting a second example method implemented by the measurement processor of FIG. 5 that determines a sensor pixel to mm (millimeter) ratio using radiographic images of natural teeth when an image sensor cannot be determined.
Figure 8:
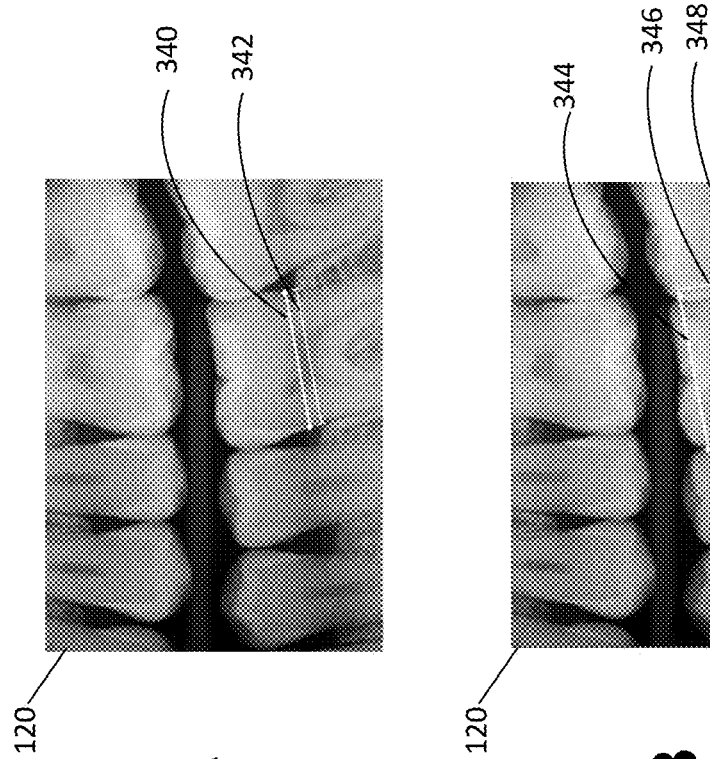
FIGS. 8A-8B are examples of measurements performed on radiographic images of natural teeth according to the method of FIG. 7.

FIG. 7 depicts Oral Structure Measurement Method 320 as selected by selector 302. In response to a determination that the radiographic image metadata does not include a known sensor type or that the sensor type cannot be otherwise determined, Oral Structure Measurement Method 320 is selected as an alternative to obtain calibrated measurements using oral structures identified in the radiographic image. Thus, in step 322, natural teeth without restorations are identified as oral structures (this identification may be made by the image processor 200 of FIG. 1A, as one of the label outputs provided by one of ML models implemented by the image processor 200). In step 324, a distance (in pixels) is measured between the mesial and the distal CEJ points on the identified teeth. In step 326, selected conversions of pixels to millimeter (or some other standard-unit of length) using a database of anatomical averages for each tooth, as obtained from library 150, are made. In step 328, ratios of CEJ distances between all pairs of teeth to identify outliers are determined. In Step 330, if there is a single outlier, then that outlier may be eliminated. In step 332, if there are multiple outliers, teeth with the least standard deviation from the CEJ distances provided in the database are selected. In step 334 an average pixel to millimeter ratio of the remaining teeth is calculated. In step 336 a pixel to millimeter ratio for the selected tooth is made.

The process of identifying outliers and eliminating them may be done in alternative ways, including, for example, using Kalman filtering, to eliminate sources of error to the extent possible. An alternative embodiment for steps 330 through 334 may include the use machine learning methods which provide a more flexible method of choosing which tooth and which measurement to obtain the pixel to millimeter ratio. For example, decisions based on trained ML models may identify a particular tooth or a particular set of measurements that will likely provide optimal results based on experience with a particular patient or a particular set of patients to obtain the most reliable measurement in the radiographic image 120.

FIGS. 8A and 8B illustrate the measurements performed in step 324 of the image processor 200 operating on the radiographic image 120 and oral structure 125 to identify the appropriate points necessary for measurements of the oral structure 125. The outer border of the dental crowns is traced using at least one of the Segmenter and Object Detectors 210-212 (selected according to the image type). A minimum distance of each pixel of the outer border of the occlusal surface from the CEJ to CEJ line is calculated and an occlusal surface line 344 parallel to the CEJ to CEJ point line 340 is generated at the average minimum distance of all pixels included within the occlusal surface. An CEJ-occlusal plane line distance 346 between the occlusal surface line 344 and the CEJ to CEJ line 340 is measured in pixels. A ratio between the CEJ-occlusal plane line distance 346 and a CEJ-boney crest distance 348 is calculated and compared with reference data from the library 150 to determine if local bone loss is present above a determined bone loss threshold.

Figure 9:
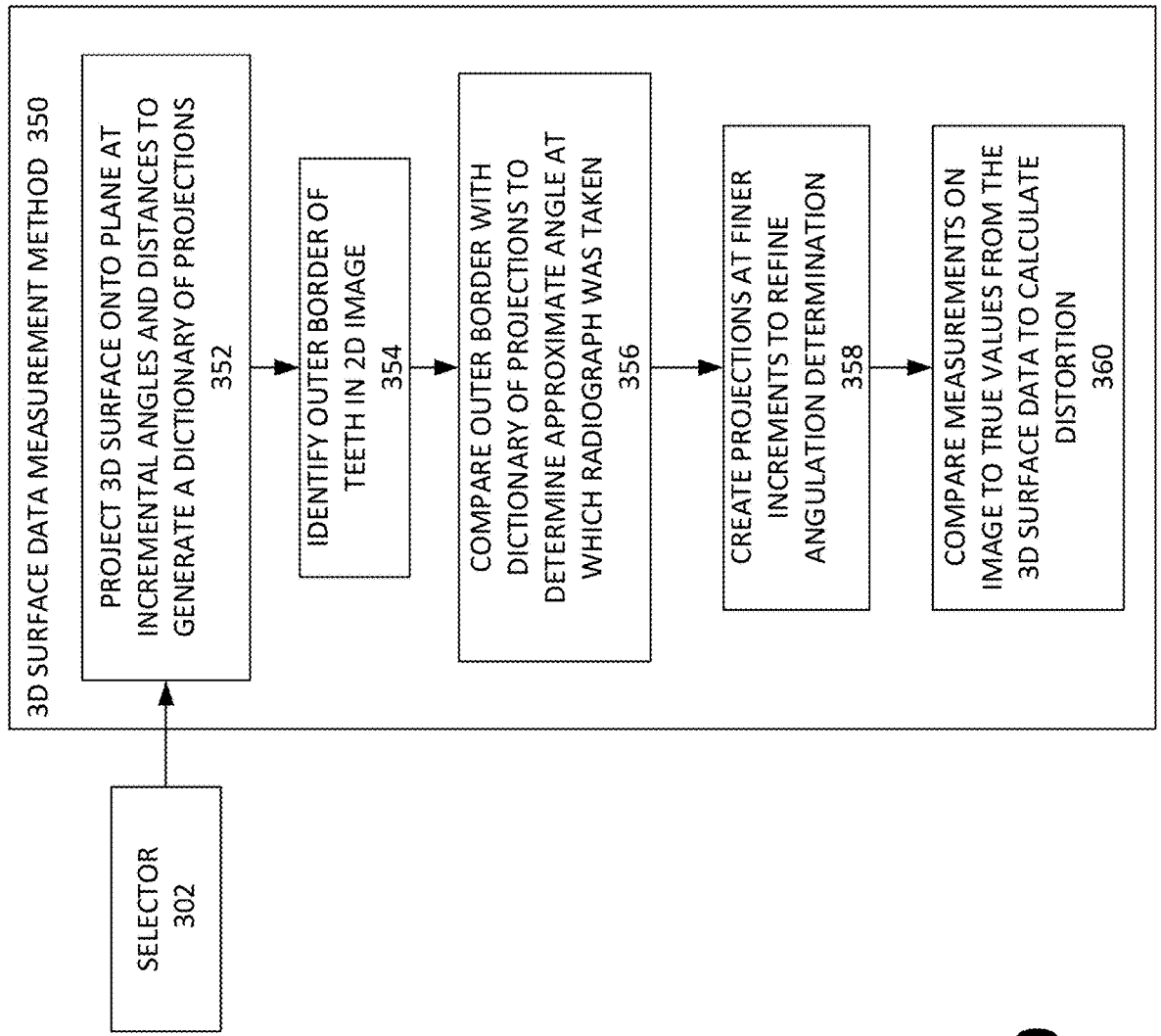
FIG. 9 is a flow diagram depicting a third example method implemented by the measurement processor of FIG. 5 that determines a sensor pixel to mm (millimeter) ratio using radiographic images of natural teeth.

FIG. 9 depicts the 3D Surface Data Measurement Method 350 performed when selected by the selector 302. Surface Data Measurement Method 350 may be used when sensor can or cannot be determined. If the sensor information is present the 3D surface data provides increased accuracy of measurement by accounting for image angulations. If the sensor information is not present, the 3D surface data may be used to provide mm to pixel ratio (or to provide some other pixel-to-standard-unit ratio).

Data from 3D dental imaging, such as an optical surface scan and/or cone beam computed tomography, is used to generate a dictionary of 2D projections of the oral structures projected onto a plane at incremental distances and from incremental angles. A computational minimization problem will be utilized to arrive at final solution. A 2D (two dimensional) radiographic image is analyzed (e.g., by the image processor 200) to determine the outer borders of craniofacial structures of interest within the image (the outer border can be generated as an output of a ML model trained to generated outer border of craniofacial structures, or through some analytical/filter-based processing), and the library of two-dimensional projections is searched to determine a match between the radiographic image and a two-dimensional projection from the library. The matched images can then be used to determine the angulation at which the original 2D radiographic image was taken. 3D structures that can be used to calculate angulation of the x-ray source compared with the imaged structures include dental implants, dental restorations, and dental hard tissue structures (e.g., teeth and bone). When the angulation of the imaged oral structure 125 is known, the total distortion of the image can be calculated, and the distances measured on dental radiographs can be calibrated.

FIG. 10 depicts a dictionary of projections 352 that can be generated by projecting a 3D surface, in this case the oral structure 125 onto a plane at incremental angles as shown across angles A, B, and C. Any number of possible angles and projections may be chosen to create the dictionary of projections (at step 352 of FIG. 9) to obtain a desired level of precision. The dictionary of projections may be stored in, and subsequently retrieved from, the library 150. Potential applications for calibrated distance measurements in dentistry may include, but are not limited to: measuring root canal length during endodontic procedures, measuring root canal length and length of canal preparation during dental post placement procedures, measuring vertical and horizontal dimension of bone in prospective implant placement sites, determining vertical level of alveolar bone in relation to adjacent structures (e.g., teeth) to monitor periodontal disease progression, and determining distance between dental restorations and the underlying alveolar bone, measuring distance between inferior alveolar nerve and adjacent structures, objects or osteotomy sites, measuring distance between maxillary sinus floor and adjacent structures, objects or osteotomy sites, and determining angulation of implants compared to adjacent teeth and structures.

Referring back to FIG. 9, in step 354, an outer border of a tooth, corresponding to the oral structure 125 in the radiographic image 120, are identified. In step 356, the outer border is compared with the dictionary of projections to determine the approximate angle at which the radiographic image 120 was taken. In step 358, projections may be created or retrieved from the library 150 at increasingly finer increments as desired to refine an angulation determination. In step 360, measurements from the radiographic image 120 and oral structure 125 are compared with true measurement values from the dictionary of projections 352 to calculate a distortion value related to the approximate angle that can be used to determine the pixel to millimeter ratio.

Figure 11:
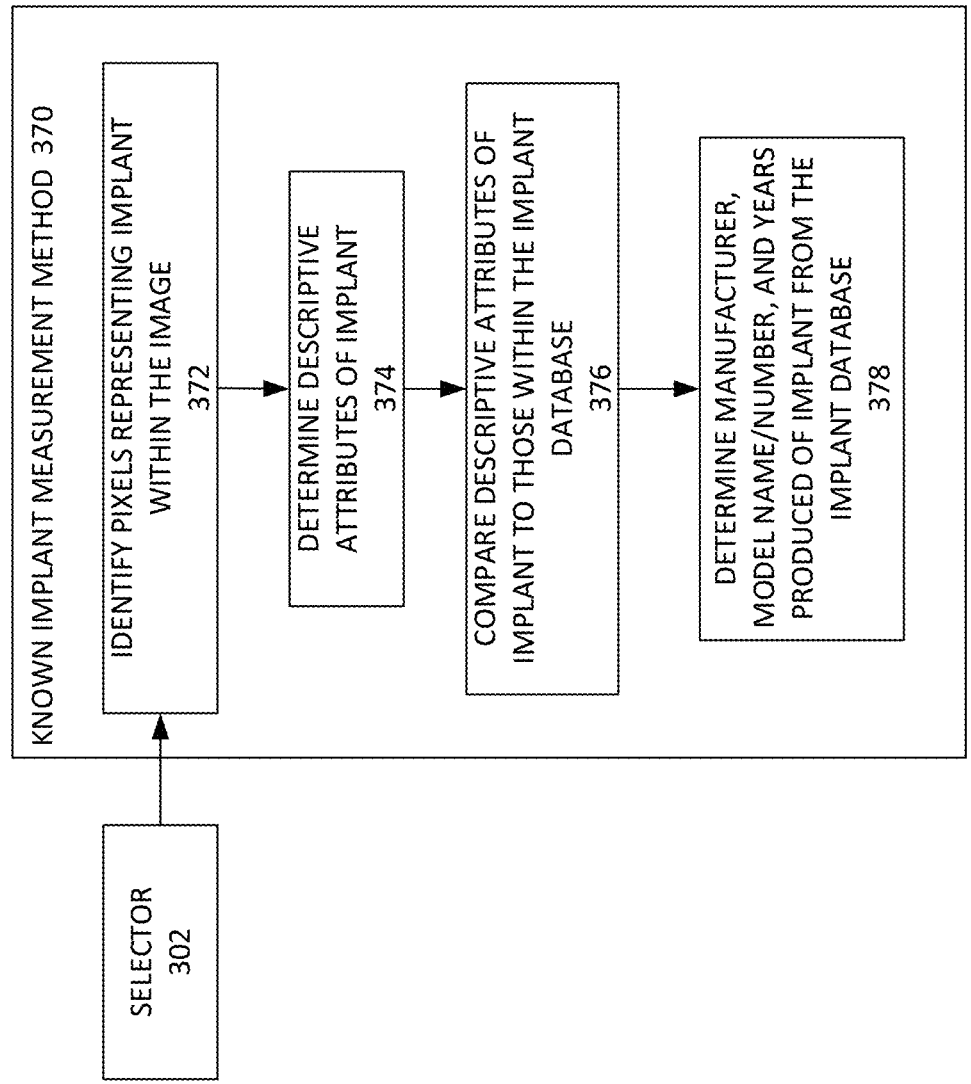
FIG. 11 is a flow diagram depicting a fourth example method implemented by the measurement processor of FIG. 5 that determines a sensor pixel to mm (millimeter) ratio by identifying an implant from an implant database.

FIG. 11 depicts the Known-Implant-Measurement Method 370 performed when selected by selector 302. In step 372, an area of the input radiographic image 120 corresponding to a dental implant within the radiographic image 120 image are identified (e.g., by the image processor, implementing an ML model for identifying and marking dental implants). In step 374, descriptive attributes of the dental implant are determined (e.g., by a same or different ML model implemented by the image processing 200, and applied to the source radiographic image 120). In step 376, the descriptive attributes of the dental implant are compared to those within a dental implant database from library 150. In step 378, the output representing the implant(s) are analyzed to determine descriptive attributes of the implant(s), including for example: type of implant interface, flange shape, presence or absence collar and shape of collar, presence or absence of micro threading, presence or absence of implant taper and location of taper, presence or absence of threads and number of threads, presence or absence of mid-body grooves, shape of implant apex, presence or absence of open implant apex, presence or absence of holes and shape of holes present, presence or absence of an apical implant chamber, and presence or absence of apical grooves. A list of identified attributes and identifies implants with identical attributes stored within a database of previously classified implant models is retrieved (e.g., from the library 150). Information retrieved about the implant may include the manufacturer, model name and/or number, years during which the reported implant model was produced by the manufacturer (as obtained from the implant database), etc. Given the detailed geometric information available about the dental implant, the pixel to millimeter ratio 385 can then be determined.

Figure 12:
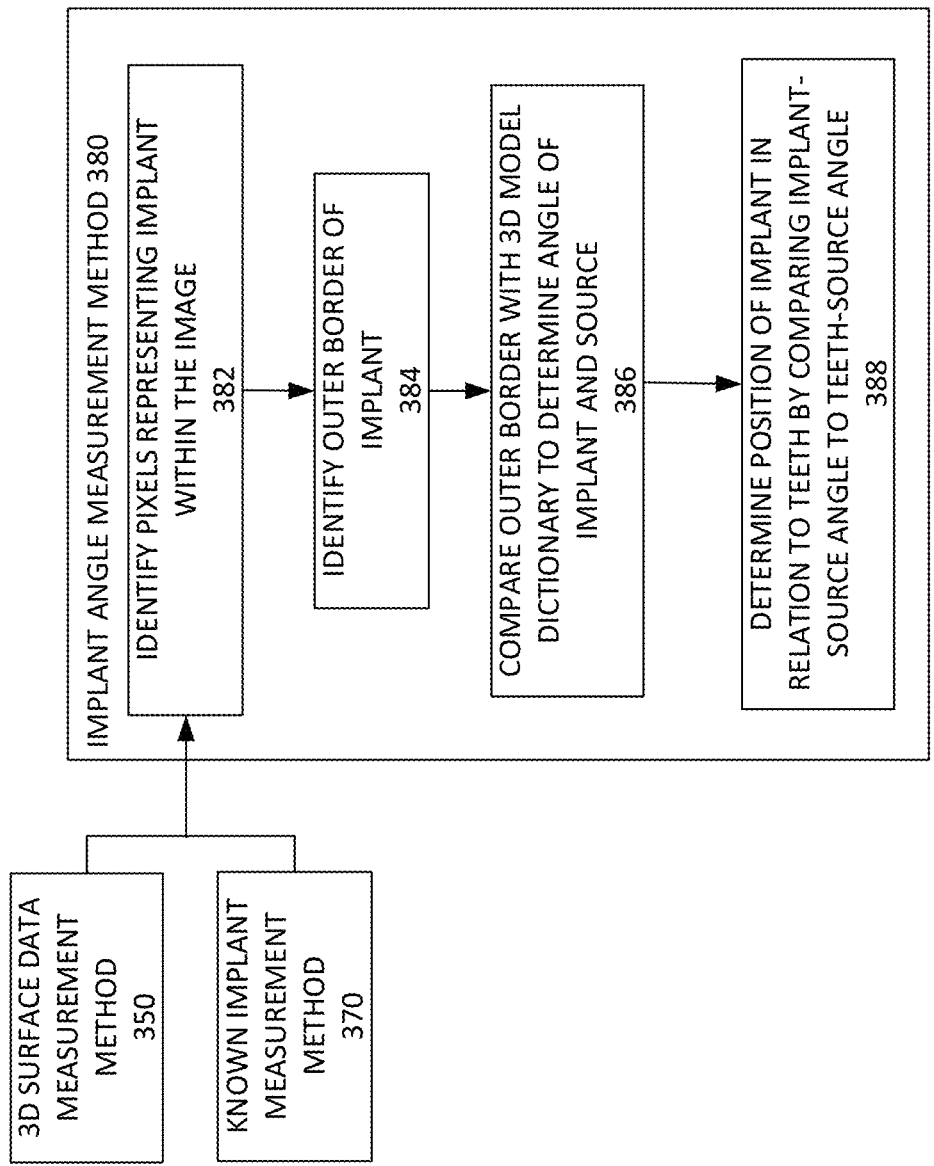
FIG. 12 is a flow diagram depicting a fifth example method in the measurement processor of FIG. 5 that determines a sensor pixel to mm (millimeter) ratio using the metadata from the third and fourth methods.

FIG. 12 depicts the Implant-Angle-Measurement-Method 380, when selected by the selector 302. This methodology is a combination of the 3D Surface Data Measurement Method 350 described above in relation to FIG. 9, and the Known Implant Measurement Method 370 described in relation to FIG. 11. Thus, under this combined methodology, the Implant Angle Measurement Method 380 may be performed when the combination of both methods 350 and 370 have been previously selected by the selector 302. In this way, the most accurate measurement data can be derived based on the outputs of methods 350 and 370 to be further processed by method 380.

For a radiographic image 120 featuring an identified dental implant, an implant database with associated implant size measurements may be used to identify the angle at which the implant was oriented in relation to an x-ray sensor 312 when the image was produced. The distortion of implant dimensions on the radiograph compared with the true proportions of the implant allow for the calculation of the angle and position of the implant in relation to the x-ray source and sensor. Comparison of the angle between the implant and x-ray source and adjacent dental crowns and the x-ray sources allows for the determination of the angulation of the dental implant in relation to teeth and adjacent structures, including for example, restorations, bone structure, and periodontal ligaments. The implant model is identified using, for example, the Known Implant Measurement Method 370. The identified pixels representing the implant(s) in the image are identified and total distortion of the implant shape is calculated from the change in implant proportions as compared with implant's true dimensional proportions. Total distortion of implant is then used to calculate the angle at which the implant was oriented in relation to the x-ray sensor 312 when the radiographic image 120 image was produced.

The calculated angle between implant(s) identified in dental radiograph 120 and the x-ray source is compared with the calculated angle between adjacent teeth present in the dental radiograph 120 and the x-ray source from method 350, in order to calculate the angle between the implant(s) identified in dental radiograph and adjacent teeth present in the dental radiograph.

In step 382, pixels representing a dental implant within the radiographic image 120 as the oral structure 125 image are identified. In step 384, the outer border of the dental implant is identified. In step 386, the outer border is compared with the Dictionary of Projections 352 to determine the angle of the implant and the plane of the sensor 312 with respect to the x-ray source. In step 388, the position of the dental implant in relation to other teeth is determined by comparing the implant source angle to the teeth source angle. Given the detailed geometric information available about the dental implant and the angle of the sensor 312, the pixel to millimeter ratio 385 can then be determined with the highest accuracy.

Referring back to FIG. 5, the collective outputs of the selected combination of methods 304, 320, 350, and 370, and 380 comprise the sensor pixel to mm ratios 385, any of which can be selectively employed based on desired measurement accuracy and their availability from each method, along with the image metadata that is in terms of pixels, to produce a calibrated measurement 390 that provides desired measurements of the oral structures 125 in terms of millimeters. Depending on the available combination of methods 304, 320, 350, 370, and 380 to provide the sensor pixel to mm ratio 385, step 392 provides a measurement confidence indication which in turn is used to determine a threshold 394.

In some embodiments, confidence metrics are used to determine which tooth is used for calibration of relative to absolute measurements using various factors (e.g., ranked standard deviation of tooth anatomy for each given tooth type, presence of previous dental restoration, and pairwise analysis of ratios between available teeth within the image that may be used to complete the calibration process and to determine outliers and discard them from the calibration process). Kalman filtering techniques may also be used to incorporate multiple sources of information and make use of all available measurements even if they may be noisy. At least some of this information can be incorporated with a known uncertainty to weight their contribution. Confidence of calibration 392 is used to adjust threshold 394 for accepting or rejecting the presence of bone loss. Further use of ML techniques provided by training mechanism 140 may further enhance the reliability and confidence level of measurements based on further use of available inputs applied in various combinations of available information, such as data related to previous radiographic images, measurements, and oral structures for particular patients that take their historical information into account, as well as information on particular sensor types (such as particular known characteristics that could create noise).

The library 150 is collectively a data library that may be used to allow the various methods featured in the system 100 to be performed. The library 150 may be comprised of data outputted by earlier executions of the above-described measurement methodologies, or may be available from third-party sources.

Types of information within the library 150 may include, but are not limited to:

1. X-Ray Sensor Database
   Sensor names
   Sensor size
   Dimensions of effective areas (length and width)

| Dental Sensor Data | Name | Manufacturer | Effective area length | Effective area width |
|---|---|---|---|---|
| Sensor 1 | "33", size 2 | Schick | _._mm<br>_._mm | _._mm<br>_._mm |
| Sensor 2 | "Dream Sensor", size 0 | DentiMax | _._mm<br>_._mm | _._mm<br>_._mm |

2. Implant Database;
   Implant names
   Implant specifications
   Manufacturer
   Model name
   Years produced
   Dimensions
   Descriptive attributes Once the implant is identified using the database, the pixel to mm ratio of the image can be determined.

3. Population-Based Anatomical Averages
   Average dental crown dimensions

| Average Crown Mesiodistal Width at CEJ Level | Tooth #1 | Tooth #2 | Etc. |
|---|---|---|---|
| Male | _._mm | _._mm | _._mm |
| Female | _._mm | _._mm | _._mm |

Average CEJ-bone level distance

| Average CEJ-Alveolar Crest Distance | Tooth #1 | Tooth #2 | Etc. |
|---|---|---|---|
| Male | _._mm | _._mm | _._mm |
| Female | _._mm | _._mm | _._mm |

Average dental root dimensions

| Average Root Length | Tooth #3 palatal root | Tooth #3 mesiobuccal root | Tooth #3 distobuccal Root | Tooth #4 buccal Root | Etc. |
|---|---|---|---|---|---|
| Male | _._mm | _._mm | _._mm | _._mm | _._mm |
| Female | _._mm | _._mm | _._mm | _._mm | _._mm |

Figure 13:
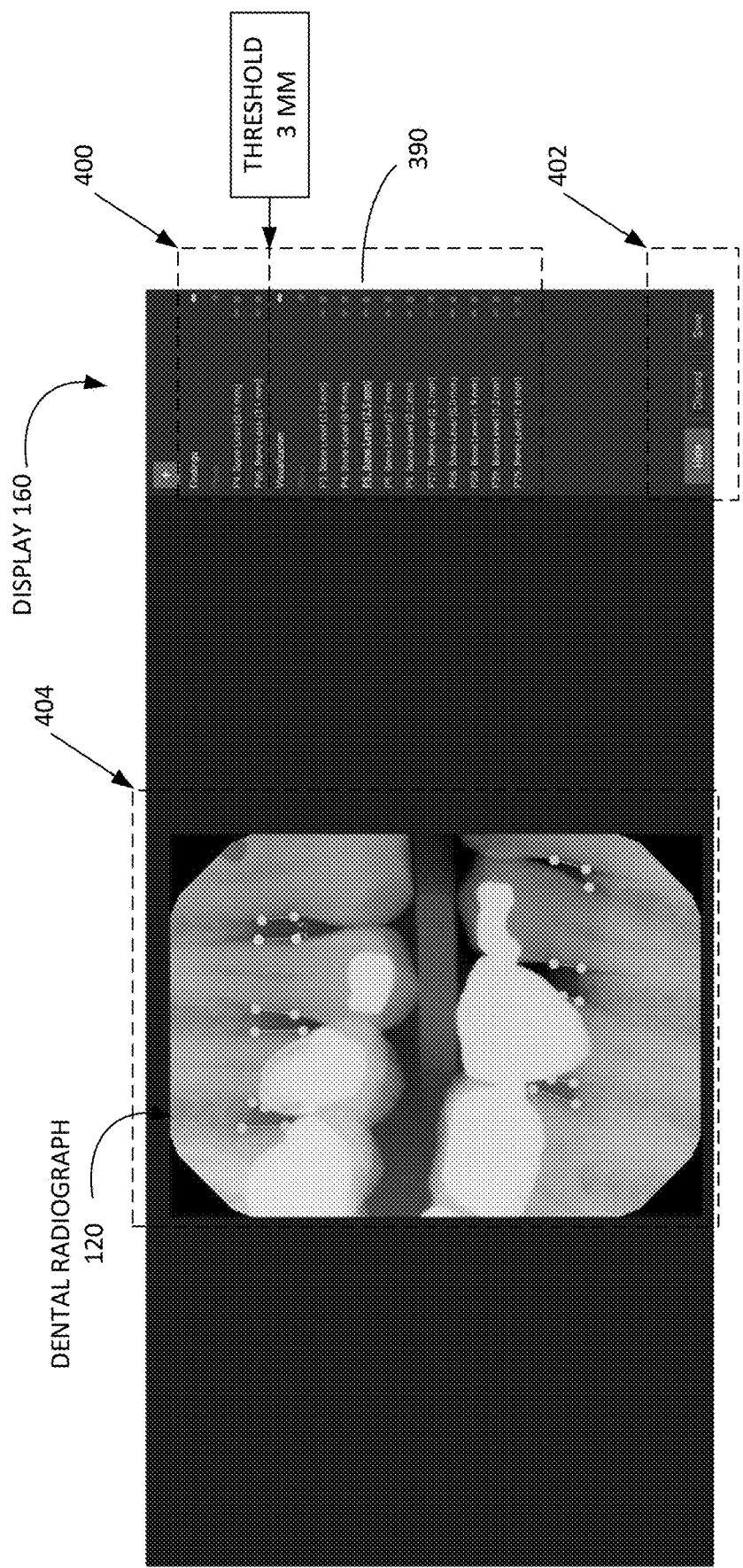
FIG. 13 is an example graphical user interface (GUI) screen for presenting desired calibrated measurements related to a radiograph image.

4. Patient-Specific Data
   Previous 2-D radiographs
      Folder of 2-D image files (.jpg, .png, etc.)
      Table of Measurements gathered from processed images
   Previous 3-D radiographs
      Folder of 3-D files (DICOM, NRRD, etc.)
      Table of Measurements gathered from processed images
   Previous 3-D surface scans
      Folder of 3-D surface files (.stl)
      Table of Measurements gathered from processed images FIG. 13 is an example GUI (graphical user interface) screen on the display 160 for allowing a user to view the dental radiographic image 120 in a display area 404 that may include various oral structures 125. A set of graphical measurements may be superimposed on the dental radiographic image 120 in the display area 404 that correspond to a set of calibrated measurements 390 that are displayed in a data area 400. The set of calibrated measurements 390 may be divided according to the threshold 394 that is determined in the measurement processor 300. Alternatively, the GUI screen may provide further user controls such as the ability for the user to set the threshold 394 manually as shown by the THRESHOLD 3 MM control. A user control area 402 includes various GUI screen functions that may include Hide, Discard, and Save functions related to the displayed measurement results.

Figure 14:
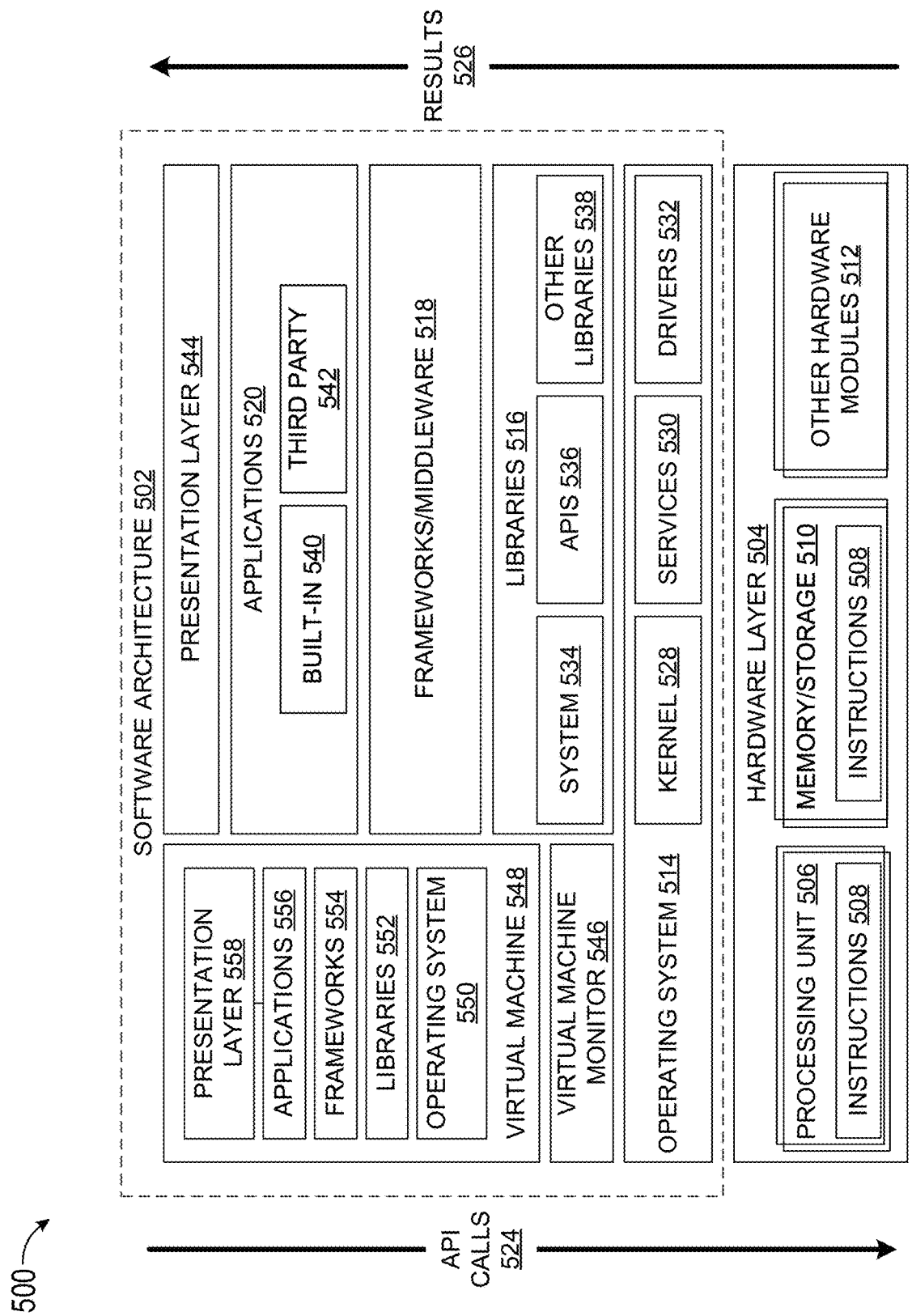
FIG. 14 is a block diagram illustrating an example software architecture, various portions of which may be used in conjunction with various hardware architectures herein described.

FIG. 14 is a block diagram 500 illustrating an example software architecture 502 that the system 100 may execute on, various portions of which may be used in conjunction with various hardware architectures herein described (including for the utilization integrity detection and/or fraud detection implementations described below). FIG. 14 is a non-limiting example of a software architecture and many other architectures may be implemented to facilitate the functionality described herein. The software architecture 502 may execute on hardware such as client devices, native application provider, web servers, server clusters, external services, and other servers. A representative hardware layer 504 includes a processing unit 506 and associated executable instructions 508. The executable instructions 508 represent executable instructions of the software architecture 502, including implementation of the methods, modules and so forth described herein.

The hardware layer 504 also includes a memory/storage 510, which also includes the executable instructions 508 and accompanying data. The hardware layer 504 may also include other hardware modules 512 that may include one or more graphics processing units (GPU), such NVIDIA™ GPU's), and may also include special purpose logic circuitry, e.g., an FPGA (field programmable gate array), an ASIC (application-specific integrated circuit), a DSP processor, an accelerated processing unit (APU), an application processor, customized dedicated circuitry, etc., to implement, at least in part, the processes and functionality for the implementations, processes, and methods described herein. Instructions 508 held by processing unit 506 may be portions of instructions 508 held by the memory/storage 510.

The example software architecture 502 may be conceptualized as layers, each providing various functionality. For example, the software architecture 502 may include layers and components such as an operating system (OS) 514, libraries 516, frameworks 518, applications 520, and a presentation layer 544. Operationally, the applications 520 and/or other components within the layers may invoke API calls 524 to other layers and receive corresponding results 526. The layers illustrated are representative in nature and other software architectures may include additional or different layers. For example, some mobile or special purpose operating systems may not provide the frameworks/middleware 518.

The OS 514 may manage hardware resources and provide common services. The OS 514 may include, for example, a kernel 528, services 530, and drivers 532. The kernel 528 may act as an abstraction layer between the hardware layer 504 and other software layers. For example, the kernel 528 may be responsible for memory management, processor management (for example, scheduling), component management, networking, security settings, and so on. The services 530 may provide other common services for the other software layers. The drivers 532 may be responsible for controlling or interfacing with the underlying hardware layer 504. For instance, the drivers 532 may include display drivers, camera drivers, memory/storage drivers, peripheral device drivers (for example, via Universal Serial Bus (USB)), network and/or wireless communication drivers, audio drivers, and so forth depending on the hardware and/or software configuration.

The libraries 516 may provide a common infrastructure that may be used by the applications 520 and/or other components and/or layers. The libraries 516 typically provide functionality for use by other software modules to perform tasks rather than interacting directly with the OS 514. The libraries 516 may include system libraries 534 (for example, C standard library) that may provide functions such as memory allocation, string manipulation, file operations. In addition, the libraries 516 may include API libraries 536 such as media libraries (for example, supporting presentation and manipulation of image, sound, and/or video data formats), graphics libraries (for example, an OpenGL library for rendering 20 and 30 graphics on a display), database libraries (for example, SQLite or other relational database functions), and web libraries (for example. Web Kit that may provide web browsing functionality). The libraries 516 may also include a wide variety of other libraries 538 to provide many functions for applications 520 and other software modules.

The frameworks 518 (also sometimes referred to as middleware) provide a higher-level common infrastructure that may be used by the applications 520 and/or other software modules. For example, the frameworks 518 may provide various graphic user interface (GUI) functions, high-level resource management, or high-level location services. The frameworks 518 may provide a broad spectrum of other APIs for applications 520 and/or other software modules.

The applications 520 include built-in applications 520 and/or third-party applications 522. Examples of built-in applications 520 may include, but are not limited to, a contacts application, a browser application, a location application, a media application, a messaging application, and/or a game application. Third-party applications 542 may include any applications developed by an entity other than the vendor of the particular system. The applications 520 may use functions available via OS 514, libraries 516, frameworks 518, and presentation layer 544 to create user interfaces to interact with users.

Some software architectures use virtual machines, as illustrated by a virtual machine 548. The virtual machine 548 provides an execution environment where applications/modules can execute as if they were executing on a hardware machine. The virtual machine 548 may be hosted by a host OS (for example, OS 514) or hypervisor, and may have a virtual machine monitor 546 which manages operation of the virtual machine 548 and interoperation with the host operating system. A software architecture, which may be different from software architecture 502 outside of the virtual machine, executes within the virtual machine 548 such as an OS 550, libraries 552, frameworks 554, applications 556, and/or a presentation layer 558.

Figure 15:
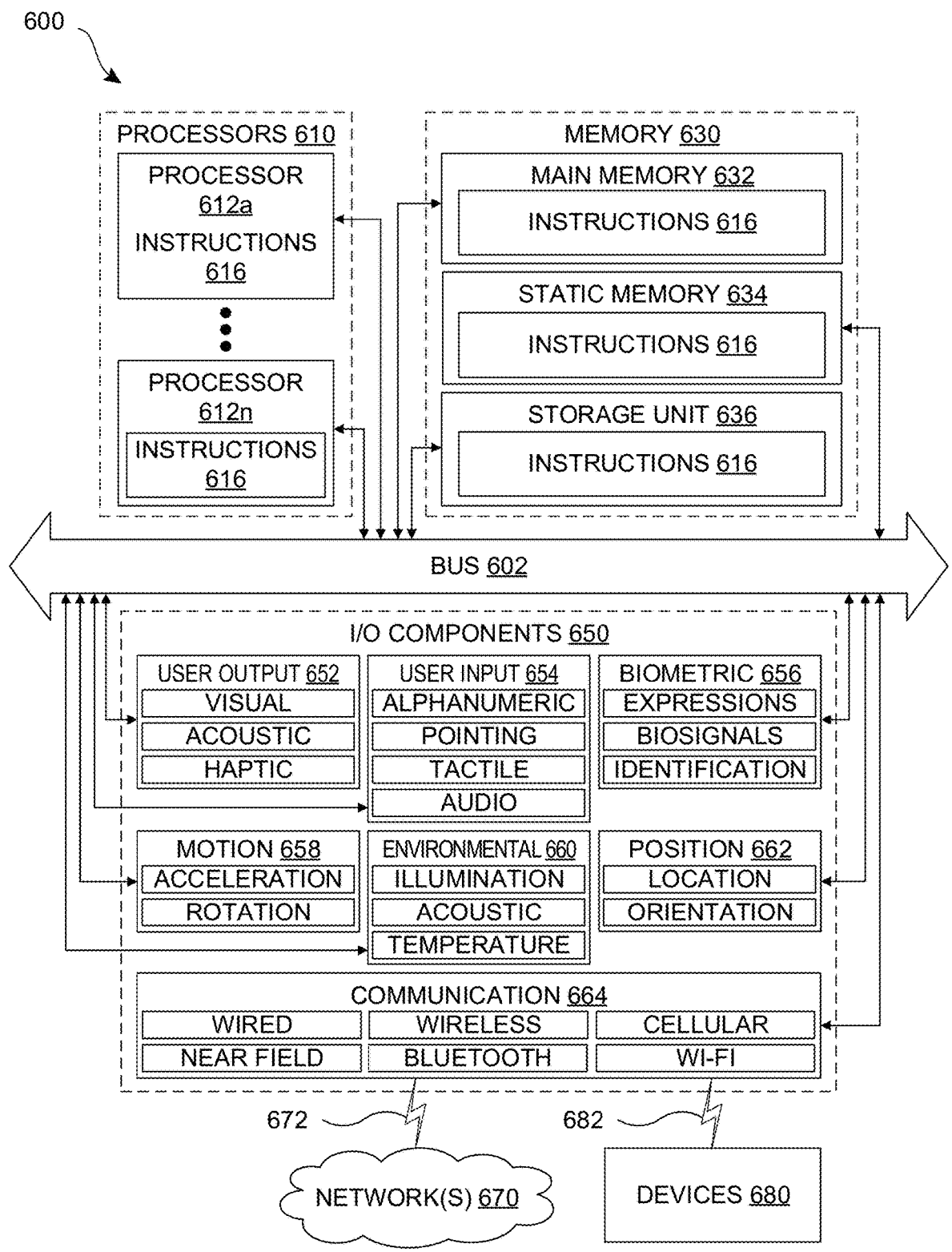
FIG. 15 is a block diagram illustrating components of an example machine configured to read instructions from a machine-readable medium and perform any of the features described herein.

FIG. 15 is a block diagram illustrating components of an example machine 600 configured to read instructions from a machine-readable medium (for example, a machine-readable storage medium) and perform any of the features described herein that any of the various system (including the system 100, the system 700 of FIG. 16, and any of the implementations of FIGS. 19-22) of the present disclosure can execute instructions on. The example machine 600 is in a form of a computer system, within which instructions 616 (for example, in the form of software components) for causing the machine 600 to perform any of the features described herein may be executed. As such, the instructions 616 may be used to implement methods or components described herein. The instructions 616 cause unprogrammed and/or unconfigured machine 600 to operate as a particular machine configured to carry out the described features. The machine 600 may be configured to operate as a standalone device or may be coupled (for example, networked) to other machines. In a networked deployment, the machine 600 may operate in the capacity of a server machine or a client machine in a server-client network environment, or as a node in a peer-to-peer or distributed network environment. Machine 600 may be embodied as, for example, a server computer, a client computer, a personal computer (PC), a tablet computer, a laptop computer, a netbook, a set-top box (STB), a gaming and/or entertainment system, a smart phone, a mobile device, a wearable device (for example, a smart watch), and an Internet of Things (IoT) device. Further, although only a single machine 600 is illustrated, the term "machine" includes a collection of machines (e.g., distributed machines) that individually or jointly execute the instructions 616.

The machine 600 may include processors 610, memory 630, and I/O components 650, which may be communicatively coupled via, for example, a bus 602. The bus 602 may include multiple buses coupling various elements of machine 600 via various bus technologies and protocols. In an example, the processors 610 (including, for example, a central processing unit (CPU), a graphics processing unit (GPU), a digital signal processor (DSP), an ASIC, or a suitable combination thereof) may include one or more processors 612a to 612n that may execute the instructions 616 and process data. In some examples, one or more processors 610 may execute instructions provided or identified by one or more other processors 610. The term "processor" includes a multi-core processor including cores that may execute instructions contemporaneously. Although FIG. 15 shows multiple processors, the machine 600 may include a single processor with a single core, a single processor with multiple cores (for example, a multicore processor), multiple processors each with a single core, multiple processors each with multiple cores, or any combination thereof. In some examples, the machine 600 may include multiple processors distributed among multiple machines.

The memory/storage 630 may include a main memory 632, a static memory 634, or other memory, and a storage unit 636, both accessible to the processors 610 such as via the bus 602. The storage unit 636 and memory 632, 634 store instructions 616 embodying any one or more of the functions described herein. The memory/storage 630 may also store temporary, intermediate, and/or long-term data for processors 610. The instructions 616 may also reside, completely or partially, within the memory 632 and 634, within the storage unit 636, within at least one of the processors 610 (for example, within a command buffer or cache memory), within memory at least one of I/O components 650, or any suitable combination thereof, during execution thereof. Accordingly, the memory 632 and 634, the storage unit 636, memory in processors 610, and memory in I/O components 650 are examples of machine-readable media.

As used herein, "machine-readable medium" refers to a device able to temporarily or permanently store instructions and data that cause machine 600 to operate in a specific fashion. The term "machine-readable medium," as used herein, does not encompass transitory electrical or electromagnetic signals per se (such as on a carrier wave propagating through a medium); the term "machine-readable medium" may therefore be considered tangible and non-transitory. Non-limiting examples of a non-transitory, tangible machine-readable medium may include, but are not limited to, nonvolatile memory (such as flash memory or read-only memory (ROM)), volatile memory (such as a static random-access memory (RAM) or a dynamic RAM), buffer memory, cache memory, optical storage media, magnetic storage media and devices, network-accessible or cloud storage, other types of storage, and/or any suitable combination thereof. The term "machine-readable medium" applies to a single medium, or combination of multiple media, used to store instructions (for example, instructions 616) for execution by a machine 600 such that the instructions, when executed by one or more processors 610 of the machine 600, cause the machine 600 to perform and one or more of the features described herein. Accordingly, a "machine-readable medium" may refer to a single storage device, as well as "cloud-based" storage systems or storage networks that include multiple storage apparatus or devices.

The I/O components 650 may include a wide variety of hardware components adapted to receive input, provide output, produce output, transmit information, exchange information, capture measurements, and so on. The specific I/O components 650 included in a particular machine will depend on the type and/or function of the machine. For example, mobile devices such as mobile phones may include a touch input device, whereas a headless server or IoT device may not include such a touch input device. The particular examples of I/O components illustrated in FIG. 6 are in no way limiting, and other types of components may be included in machine 600. The grouping of I/O components 650 are merely for simplifying this discussion, and the grouping is in no way limiting. In various examples, the I/O components 650 may include user output components 652 and user input components 654. User output components 652 may include, for example, display components for displaying information (for example, a liquid crystal display (LCD) or a projector), acoustic components (for example, speakers), haptic components (for example, a vibratory motor or force-feedback device), and/or other signal generators. User input components 654 may include, for example, alphanumeric input components (for example, a keyboard or a touch screen), pointing components (for example, a mouse device, a touchpad, or another pointing instrument), and/or tactile input components (for example, a physical button or a touch screen that provides location and/or force of touches or touch gestures) configured for receiving various user inputs, such as user commands and/or selections.

In some examples, the I/O components 650 may include biometric components 656 and/or position components 662, among a wide array of other environmental sensor components. The biometric components 656 may include, for example, components to detect body expressions (for example, facial expressions, vocal expressions, hand or body gestures, or eye tracking), measure bio-signals (for example, heart rate or brain waves), and identify a person (for example, via voice-, retina-, and/or facial-based identification). The position components 662 may include, for example, location sensors (for example, a Global Position System (GPS) receiver), altitude sensors (for example, an air pressure sensor from which altitude may be derived), and/or orientation sensors (for example, magnetometers).

The I/O components 650 may include communication components 664, implementing a wide variety of technologies operable to couple the machine 600 to network(s) 670 and/or device(s) 680 via respective communicative couplings 672 and 682. The communication components 664 may include one or more network interface components or other suitable devices to interface with the network(s) 670. The communication components 664 may include, for example, components adapted to provide wired communication, wireless communication, cellular communication, Near Field Communication (NFC), Bluetooth communication, Wi-Fi, and/or communication via other modalities. The device(s) 680 may include other machines or various peripheral devices (for example, coupled via USB).

In some examples, the communication components 664 may detect identifiers or include components adapted to detect identifiers. For example, the communication components 664 may include Radio Frequency Identification (RFID) tag readers, NFC detectors, optical sensors (for example, one- or multi-dimensional bar codes, or other optical codes), and/or acoustic detectors (for example, microphones to identify tagged audio signals). In some examples, location information may be determined based on information from the communication components 662, such as, but not limited to, geo location via Internet Protocol (IP) address, location via Wi-Fi, cellular, NFC, Bluetooth, or other wireless station identification and/or signal triangulation.

Clinical Data Analysis

As noted, dental-care providers often require pre-authorization for certain proposed treatment plans. The requests are generally accompanied by supporting materials, including radiographic image data, to justify the proposed treatment plans. To provide quick decisions/assessments for the requests or claims, while avoiding any assessment bias that may result from reviewing requests by a large number of different reviewers (as would be required to handle the large volume of expedited requests), proposed herein is an approach that analyzes clinical data (e.g., information about the procedure treatment plan, radiographic image data, etc.) to determine, in part, whether the proposed treatment is warranted given the source radiographic image data provided with the request (and, optionally, given historical data, such as a patient's previous treatments and corresponding radiographic images). As will be discussed in greater detail below, an ML model (which may be implemented using a system architecture similar to that discussed in relation to the image processing module 200 depicted in FIG. 1) is trained to identify and mark various dental features (which may be potentially damaged or diseased, but which may be healthy) for which a claim or a pre-authorization request is submitted (or for which a treatment plan is to be automatically generated), and also identify and mark healthy (at least partly) dental structures in the image data. The marking (segmentation) of such features is used to derive dimensioned properties (area, length) metrics (e.g., ratios) that can be processed by the same or another ML engine, or by a rule-based engine, that determines, based on the proposed treatment plan submitted by the provider, and the derived metrics, the reasonableness or appropriateness of the proposed treatment. A more comprehensive clinical data analysis that depends on other information and factors (e.g., one that performs one or more analysis processes similar to those described below with respect to the Fraud and Clinical Data (Utilization) Integrity Detection framework) may also be executed to supplement the expedited area-based utilization analysis. The inclusion of supplemental clinical data analysis processing may depend on a balancing of the expediency desired to reach quick decisions and availability of data needed to carry out the supplemental processing. In some examples, the implementations discussed herein may also be used by individual dental-care providers to determine possible treatment plans to use in relation to detected conditions.

Accordingly, the implementations described herein include a method for clinical (diagnostic or utilization) data analysis that includes obtaining treatment dental data (e.g., from a repository of radiographic image data, directly from an X-ray imaging sensor, or through any other means) for an individual, with the dental data (sometimes referred to as treatment clinical data) including input radiographic image data for at least one dental object (e.g., a tooth, or a number of teeth). The method additionally includes identifying, by a learning machine, at least one first dental feature (e.g., some abnormality, such as a cavity, a decaying portion of a tooth, a restoration, bone loss, etc.) in the input radiographic image data for the at least one dental object, indicative of the existence of a dental clinical condition for the at least one dental object, and at least one other feature (e.g., clinical crown portion of the tooth, also referred to as coronal area) in the dental object comprising at least partly a healthy dental structure. The method further includes computing dimensions properties (such as areas or lengths, e.g., through pixel counting) for the at least one first dental feature and the at least one other feature comprising at least partly the healthy dental structure, and deriving based on the dimensioned properties one or more ratio metrics (e.g., a ratio of area covered by abnormal/diseased dental feature, to the area covered by a feature that includes a healthy portion) indicative of severity of the dental clinical condition for the at least one abnormal dental feature of the at least one dental object. In some embodiments, based on a comparison of the derived metric(s), a dental action (e.g., a decision by the insurance company to deny or accept the claim or request for treatment plan pre-approval) can be determined.

As described herein, because a ratio metric is a unit-less scalar value that does not require data to be measured in a specific length unit, in some embodiments, clinical data analysis to derive metric ratios based on area computation for various detected features does not necessarily require pre-calibration or pre-standardization of the source image data. Nevertheless, when a more comprehensive analysis is to be performed to supplement the use of ratio metrics, or when the derived metrics are not necessarily based on ratios, calibration of input data may need to be used. Furthermore, because embodiments that are based on ML model implementations (e.g., to detect healthy and diseased dental features) may have been trained using image data that has been calibrated in some fashion, to avoid the skewing of derived output due to an input runtime image not being calibrated in a similar way to the calibration applied to training data, the source radiographic input data may first be calibrated. Calibration procedures may include the calibration processes discussed herein in relation to FIGS. 6-12, as well as other standardization processes such as image alignment processes. Accordingly, in some embodiments, the clinical data analysis approaches described herein may further include applying a calibration procedure to the source radiographic image data to perform one or more of, for example, the known sensor measurement process, the oral structure measurement process, the 3D surface data measurement process, the known implant measurement process, and/or the implant angle measurement process.

Figure 16:
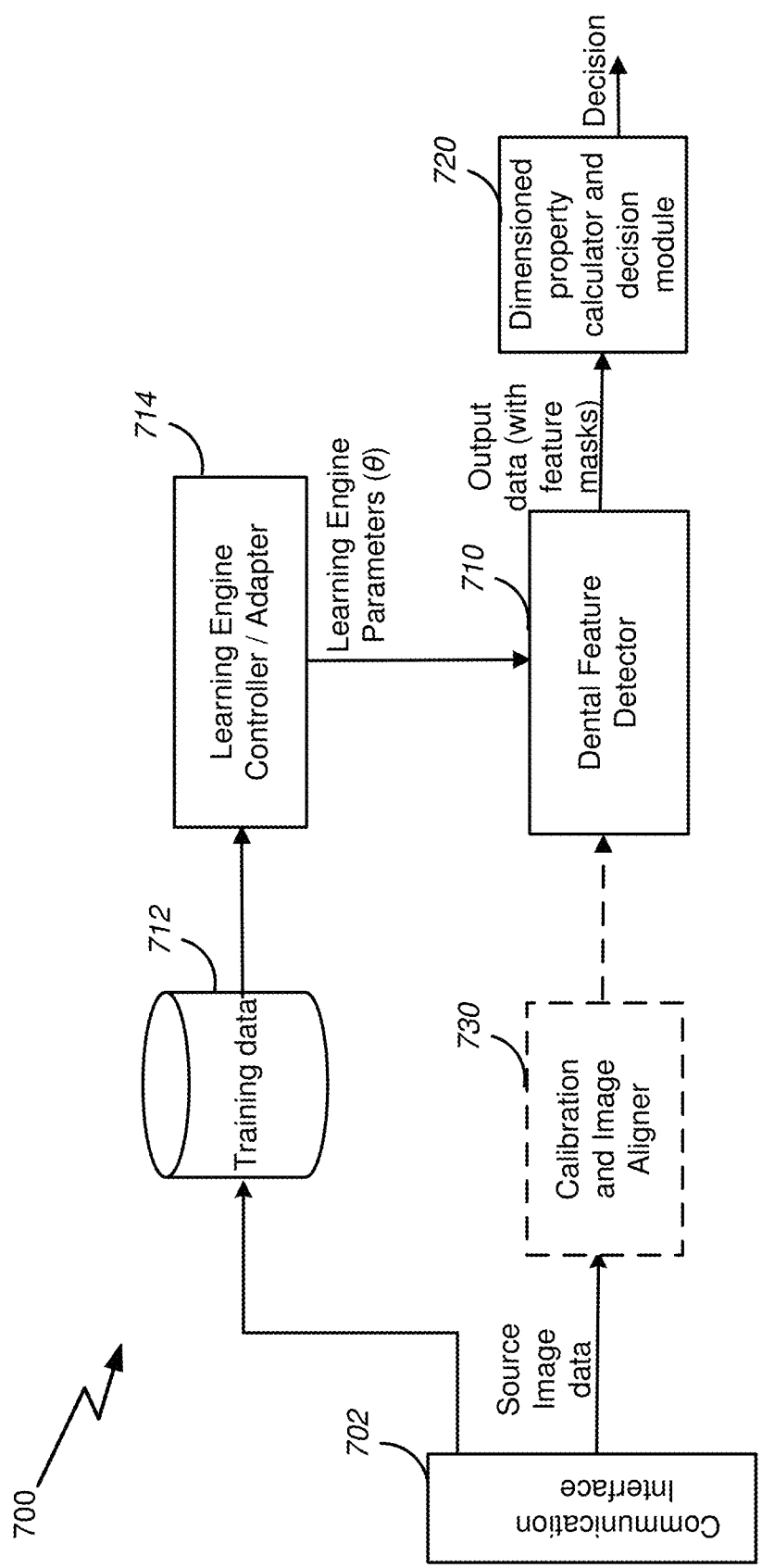
FIG. 16 is a block diagram of an example system to perform clinical data analysis.

Thus, with reference to FIG. 16, a block diagram of an example system 700 to perform clinical data analysis (and which may be configured to perform an expedited analysis that provides decisions for claims or pre-approval treatment requests within seconds or minutes of the submission of such request) is shown. Some elements of the framework depicted in FIG. 16 may be similar to the system architecture illustrated in FIGS. 1A and 1B (e.g., the elements to realize the ML-model implementation and training aspects of the architecture of FIG. 16). The system 700 includes a dental feature detector 710 (which may be implemented using a machine learning engine realized, for example, using neural networks or other types of learning machines, or implemented as an image processing/filtering engine) to identify objects in an image, label or mark such identified objects with, for example, geometric shapes indicative of the outlines/contour of the objects. The generated masks may be closed geometrical shapes (such as rectangles, or polygonal shapes) enclosing an area, or covering a length, that is used to determine metrics to assess the reasonableness of treatments proposals submitted by dental-care providers.

As also illustrated in FIG. 16, in embodiments in which a machine-learning implementation is used to perform dental feature detection (and generate masks or labels for the detected features) a training data repository 712 provides the training data that comprises radiographic images that have been labelled and/or marked with masks representative of detected dental features. The training data is generally constructed with input from human observers, and defines the ground truth for the particular ML model that is being implemented by the ML-based dental feature detector. In some embodiments, the training data stored in the repository 712 is provided to a learning engine controller/adapter 714 (which may be similar in implementation and/or functionality to the training mechanism 140 of the system 100 shown in FIGS. 1A and 1B) configured to determine and/or adapt the parameters (e.g., neural network weights) of the learning engine that would produce output representative of detected objects and/or the generated masks (e.g., geometric shapes or polygonal representations) determined for the source image data. To train the dental feature detector 710, training data comprising representations of objects/structures (diseased and healthy dental objects) imaged for different individuals is provided to the controller/adapter 714. The training data also includes label data representative of the classifications of such objects/structures (e.g., identifying the nature of the detected feature as being normal or abnormal, what part of the tooth anatomy the feature is, the tooth numbering for the teeth shown in the image, etc.) The representation data, label data, and other information included with the training data thus define samples of the ground truth that is used to train the dental feature detector 710 of the system 700 (offline and/or during runtime). This training data is used to define the parameter values (weights, represented as the vector θ) assigned to links of, for example, a neural network implementation of the learning engine implementation for the detector 710. The weight values may be determined, for example, according to a procedure minimizing a loss metric between predictions made by the neural network and labeled instances of the data (e.g., using a stochastic gradient descent procedure to minimize the loss metric). The computed parameter values can then be stored at a memory storage device (not shown) coupled to the dental feature detector 710 and/or to the controller/adapter 714. After a learning-engine based implementation of the detector 710 has become operational (following the training stage) and can process actual runtime data, subsequent run-time training may be intermittently performed (at regular or irregular periods) to dynamically adapt the detector 710 to new, more recent training data samples in order to maintain or even improve the performance of the detector 710.

As illustrated in FIG. 16, a communication interface 702 receives as input source radiographic image data, e.g., x-ray images communicated directly from an image apparatus (such as an X-ray sensor) or communicated from some intermediary central node or image repository. The data received at the communication interface 702 is generally directed to the detector 710, optionally via a calibration and image aligner unit 730, e.g., in situations where the source images need to first be calibrated/normalized to determine the appropriate pixel-to-standard-unit length scale, and to align the source image in a manner consistent with the way the training data and images from other sources have been calibrated and/or aligned. Intermittently, the communication interface 702 may also receive and forward to the training data repository 712 additional training data to perform updated training (at periodic or irregular intervals) on the learning engine controller/adapter 714.

Alternatively or additionally, in some embodiments, the detection of objects/features may be implemented using a filter-based approach, in which the input image to be analyzed is provided to a filter-based detector and mask generator, e.g., to detect shapes and objects in the image through, for example, feature detection filtering (to detect edges, corners, blobs, etc.), morphological filtering, etc., and generate respective outlines or geometric shapes representative of the dental structures, objects, or features detected in the scene.

The output of the dental feature detector 710 may include the generated masks or labels superimposed on the source input image to thus provide an output image that includes both the actual image data and the masks (e.g., geometric shapes or other representations generated for the detected dental features in the radiographic image). Examples of ML models that may be used to generate masks or marking of dental features are discussed throughout the present disclosure. Alternatively, the output image can include only the resultant mask (be it geometric shapes or outlines), arranged in a manner that maintains the relative positioning and orientation of the structures/objects in the original image relative to each other. Complex irregular polygonal shapes (to overlay or replace the actual raw data) can be derived for features appearing in the image based on optimization processes, for example, an optimization process that fits the best closed polygon to a detected object, subject to certain constraints (e.g., minimal line length for each segment of the polygon, minimal area enclosed by the polygon, etc.)

Figure 17:
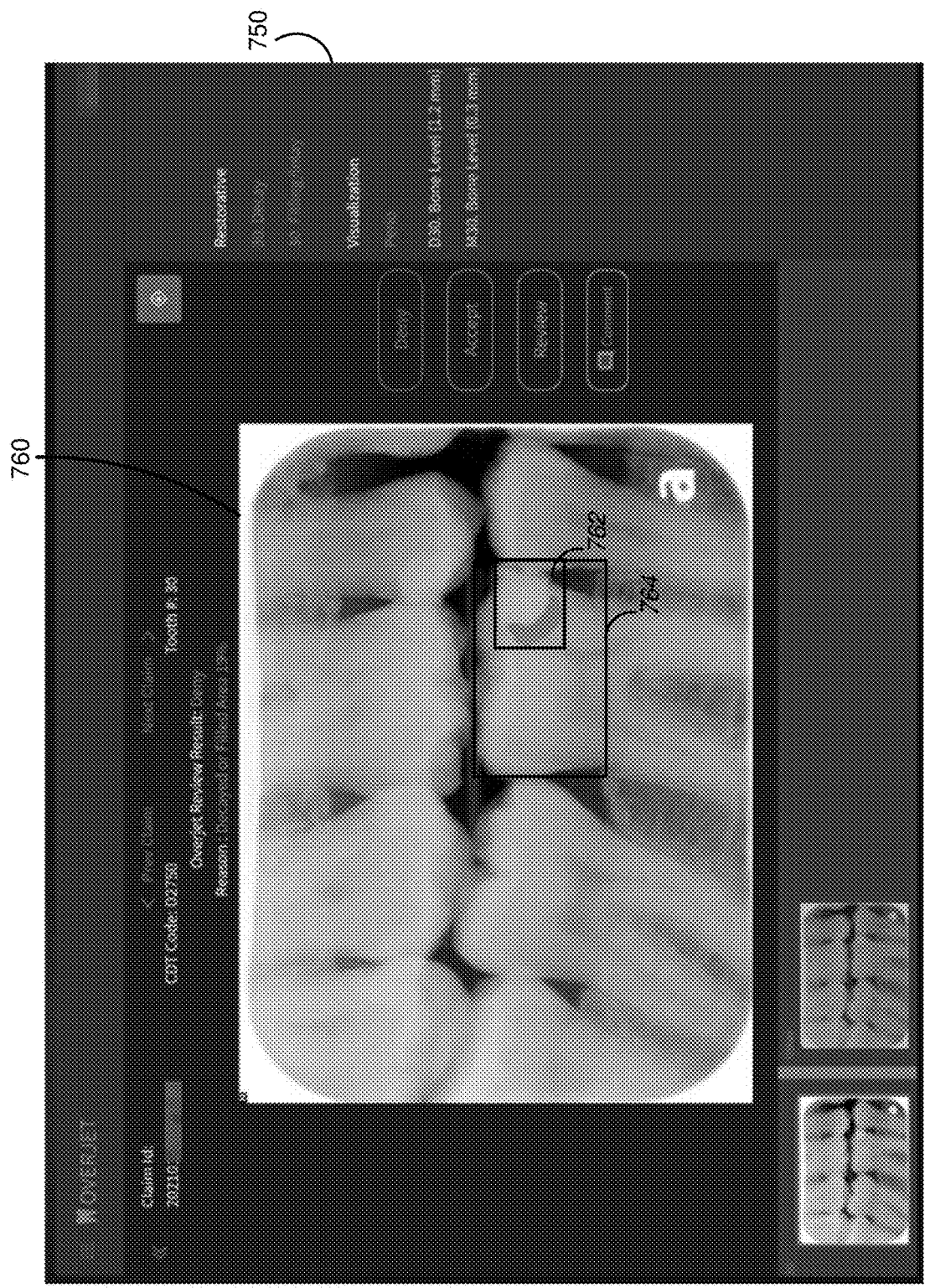
FIG. 17 is an example dashboard displaying a radiographic image on which resultant output markings corresponding to detected dental features have been superimposed.

FIG. 17 includes an example dashboard 750 displaying a radiographic image on which resultant output markings have been superimposed on an output image 760 (produced from a source input image) that includes, in addition to the raw input radiographic image data, rectangular masks representative of an area occupied by detected features. In the example of FIG. 17, two features are detected. The first is an abnormal dental feature 762, which in this case is the filling (restoration) area and adjacent area that includes a decay tooth matter. The second marked feature is a dental feature 764 that comprises, at least in part, a healthy tooth structure, which in the example of FIG. 17 is the clinical crown of the tooth (i.e., the visible portion of the tooth above the gum line). Although the image 760 includes rectangular masks that completely enclose the contours of the detected features, more complex shapes may be used (e.g., complex polygonal shapes that trace, subject to certain constraints, the contours of the feature). Furthermore, the resultant output may also include labels identifying the detected features (e.g., labelling the feature 762 as "abnormal" or "restoration+decay," and labelling the marked feature 764 as "crown"). It is to be noted that additional features could have been detected, if desired (as may be permitted by the user interface realized through the dashboard, and if such detection versatility is supported by the ML model) to, for example, separately identify and mark the restoration area and decay area as separate dental features.

Turning back to FIG. 16, following the detection, marking (or segmenting), and labeling of the detected features in the input radiographic image data, the resultant output is provided to an area calculator and decision module 720 which is configured to compute dimensions properties (e.g., areas or lengths) of the at least one first dental feature (e.g., the feature 762 in the example of FIG. 17) and the at least one other feature comprising at least partly the healthy dental structure (e.g., the clinical crown feature 764 in the example of FIG. 17). The areas of the marked features may be computed through pixel counting, or, when using simple masks (such as the rectangular masks used in the example of FIG. 17) by determining the dimensions (length and width) of each of the rectangles, and computing areas (if needed) based on those determined dimensions. Other techniques to determine or approximate areas of marking (masks) generated by the detector 710 may also be used.

Having computed the dimensioned properties (e.g., areas covered) by the masks (markings) produced by the dental feature detector 710, the module 720 is also configured to derive, based on the dimensioned properties, a metric indicative of severity of the dental clinical condition for the at least one first (e.g., abnormal or damaged) dental feature of the at least one dental object. For example, a ratio metric may be computed as a ratio of area covered by abnormal (diseased) dental feature (in the example of FIG. 17, the diseased area is the area enclosed by the rectangle 762 marking the restoration+tooth decay portion in the tooth analyzed), to the area covered by a feature that includes a healthy portion (e.g., the clinical crown area enclosed by the rectangle 764. Other metrics may also be computed instead of, or in addition to, the area ratio metric, including, for example, distances or lengths of certain features (e.g., distances between CEJ and bone point on both sides of a tooth, and CEJ and apex points; these distance metrics indicate if there is bone loss, etc.) The derived ratio metrics can subsequently be used to make a decision (using a rule-based procedure, or using another ML model implementation that may be independent of the ML model used to implement the dental feature detector 710). The decision (or some other output generated by the module 720) may be representative of a treatment plan to treat the dental issues that may have identified through operation of the detector 710 and the module 720, or may be a decision responsive to a treatment recommendation (or a pre-approval request for a proposed treatment plan) submitted as part of the clinical data by the dental-care provider treating the patient whose radiographic image data is being analyzed. For example, consider an example where, in addition to the radiographic image shown in FIG. 17, the clinical data also includes a proposed treatment plan to place a prosthetic crown over the tooth being analyzed, due to the size of the existing restoration and the expanding tooth decay adjacent to the restoration. Assume that in this example, the patient's dental insurance approves claims for synthetic crowns when the damage to the natural tooth matter is more than 40% of the clinical crown area. Based on this criterion or rule, the dental provider's treatment plan to treat the tooth for a prosthetic crown fitting would be denied because the ratio of the area of the damaged tooth matter (enclosed by the rectangle 762) to the clinical crown area is less than 40% (as illustrated in FIG. 17, the ratio of area 762 to the area 764 is less than 25%). The area ratio criterion is but one example of rules that can be implemented via the system 700 of FIG. 16, and many other criteria, which may result in elaborate decision schemes, may also be realized. It is to be noted that the module 720 may be part of the detector 710, and does not necessarily need to be implemented as a dedicated module that is separate from the detector 710.

Optionally, as also illustrated in FIG. 16, a calibration and image aligner unit 730 may be located upstream of the dental feature detector 710 to calibrate source image data for consistency with the training data used to train the ML model(s) of the system 700, and for greater uniformity of the image data provided from the numerous different sources (e.g., different dental-care providers). Calibration of the source image data (e.g., to derive a measurement scale for the images, expressed as a pixel-to-standard-unit ratio, e.g., pixel-to-mm ratio) may also be needed if severity metrics (to analyze and assess clinical data) that are not based on ratios (and in which the scale of the images would not be immaterial as a result of using ratio metrics) are used. Calibration of the source image data may be performed based on the measurement (calibration) processes discussed in relation to FIGS. 6-12. Additional details of the calibration processing performed by the calibration image aligner 730 are provided below in relation to FIG. 18.

If orientation and positioning information for the incoming input radiographic image data is available or can be derived (e.g., based on one or more of the measurement processes of FIGS. 6-12) to obtain or determine viewing angle and distance of an X-ray imaging apparatus from the imaged dental objects, the image data can be re-aligned to a common frame of reference. Such an alignment can further improve the accuracy and consistency of the images being analyzed, thus improving the robustness of the feature identification and decision making performed by the system 700. Based on the available or derived orientation and positioning information for the sensor apparatus imaging the craniofacial structures, geometrical corrections for a source image can be performed to rotate, or otherwise transform the image's pixels, according to various formulations. For example, the relative perspective of an X-ray imaging apparatus can be used to derive (using an optimization process to compute transformation parameters) a transformation matrix that is applied to the source image data to yield a resultant image corresponding to a particular viewing perspective.

Figure 18:
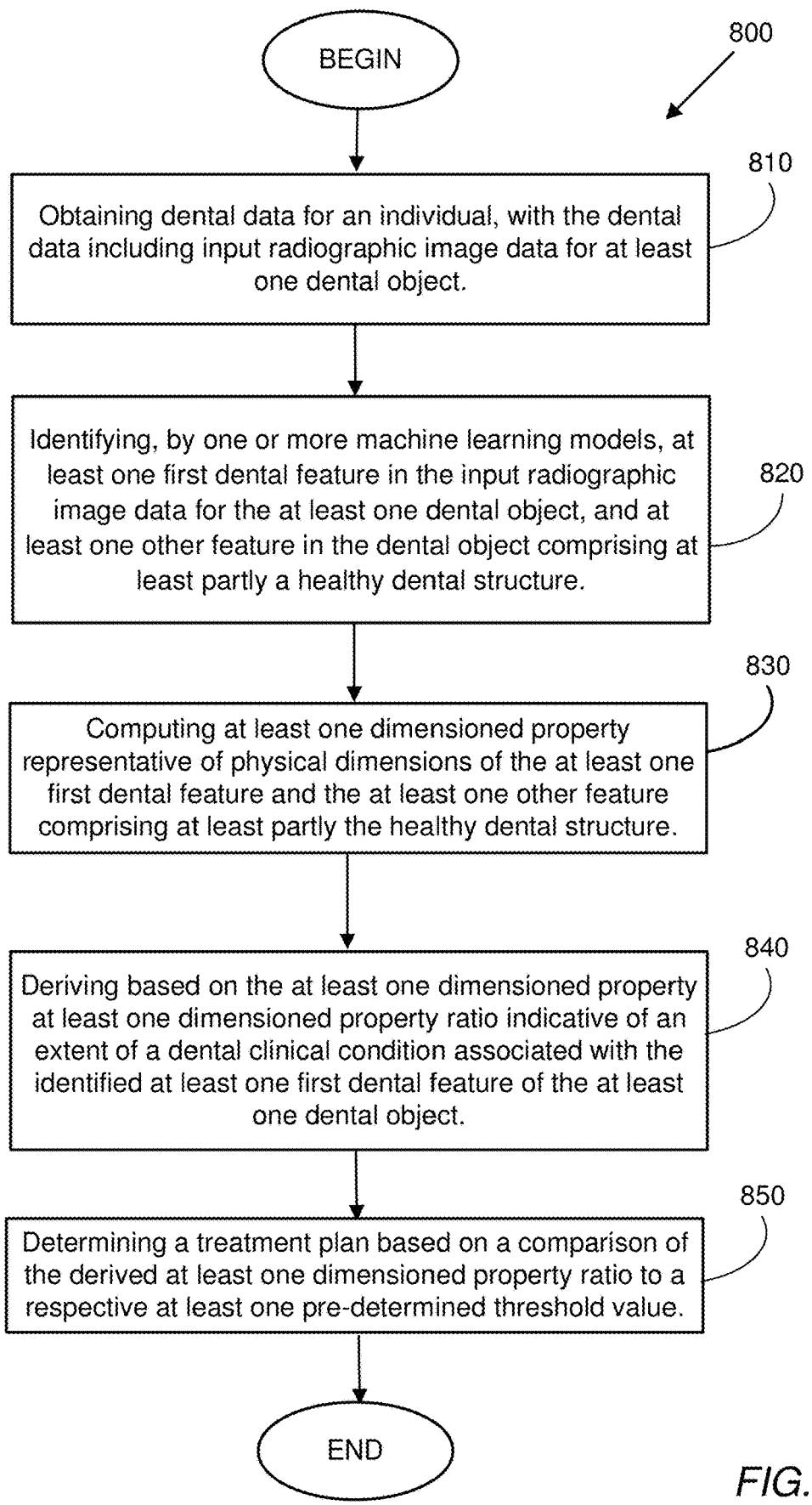
FIG. 18 is a flowchart of an example procedure for clinical data analysis.

With reference next to FIG. 18, a flowchart of an example procedure 800 for clinical data (also referred to as utilization or diagnostic data) analysis, generally performed at a computing system such as the system 700 of FIG. 16, is shown. The procedure 800 includes obtaining 810 dental data for an individual, with the dental data including input radiographic image data for at least one dental object. Dental data may be provided directly from a dental-care provider (via one or more intermediary nodes in a communications network such as the Internet) or from some central repository (possibly associated with an insurance company to whom treatment plans or claims are first submitted).

The procedure 800 further includes identifying 820, by one or more machine learning models (such as the ML-based implementation of the dental feature detector 710 of FIG. 16), at least one first (abnormal or damaged, but potentially healthy) dental feature in the input radiographic image data for the at least one dental object (that feature may be indicative of the existence of a dental clinical condition for the at least one dental object), and at least one other feature in the at least one dental object comprising at least partly a healthy dental structure (e.g., a portion of a tooth that is not diseased, restored, or damaged). For instance, the at least one first dental feature may include one or more of a decaying tooth portion for a tooth, a filling region for the tooth, a restoration, and/or bone loss, and the at least one other feature may include one or more of, for example, a clinical crown structure for the tooth, and/or root length.

In some examples, identifying, by the learning machine, the at least one first dental feature and the at least one other feature may include generating masks, by the learning machine, representative of the at least one abnormal dental feature and the at least one other feature comprising at least partly the healthy tooth structure.

With continued reference to FIG. 18, the procedure 800 additionally includes computing 830 at least one dimensioned property representative of physical dimensions of the at least one first dental feature and the at least one other feature comprising at least partly the healthy dental structure. The procedure 800 additionally includes deriving 840, based on the at least one dimensioned property at least one dimensioned property ratio indicative of an extent of a dental clinical condition associated with the identified at least one dental feature of the at least one dental object. In some examples, computing the at least one dimensioned property may include computing one or more of areas of the identified at least one first dental feature and the at least one other feature, and/or lengths of the identified at least one first dental feature and the at least one other feature. In such examples, deriving the at least one dimensioned property ratio may include one or more of deriving an area ratio of an area for the at least one first dental feature and area for the at least one other feature, and/or deriving a length ratio of a length of the at least one first dental feature and a length of the at least one other feature.

As further illustrated in FIG. 18, the procedure 800 also includes determining 850 a treatment plan based on a comparison of the derived at least one dimensioned property ratio to a respective at least one pre-determined threshold value. Determining the treatment plan may include one or more of, for example, automatically determining by machine learning model a proposed treatment plan to treat an abnormal dental feature (this may be done at a dental-care provider's clinic, or at some centralized remote server), and/or determining based on the derived dimensioned property ratio whether to approve a dental-care-provider treatment plan submitted by a dental-care provider.

As noted, it may be desirable, in some embodiments, to calibrate/standardize the received source radiographic image data. The calibration processing can include determining the scale (e.g., in some standard-unit length, such as millimeter) that pixels in the received source image represent. There are several calibration processes that are proposed herein that can be performed without requiring use of calibration objects to be included in captured image data. Those proposed processes rely instead on archival or other available information about the objects appearing in the captured image, and/or information about the sensor devices that are used for capturing the image data. Thus, in such embodiments, obtaining the clinical data may include receiving source radiographic image data represented according to pixel-based dimensions, and calibrating the source radiographic image data to produce the input radiographic image data represented in terms of estimated standard-unit dimensions, with the source radiographic image data being free of any non-dental calibration objects. The estimated standard-unit dimensions may include millimeter (mm) units.

Calibrating the source radiographic image data may include selecting a segmenter and/or an object detector, predicting source masks and source points (and/or keypoints) of the at least one dental object appearing in the source radiographic image data using the segmenter and the object detector, providing the source radiographic image data and the image metadata, comprising the source masks and source points, to a calibration process selector, selecting by the calibration process selector at least one measurement process from a set of measurement processes according to the source radiographic image data and the image metadata, deriving a sensor pixel-to-standard-unit ratio using the selected at least one measurement process, and generating the input radiographic image data and resultant calibrated metadata, which includes the calibrated masks and points on the dental object, using calibrated measurements of the at least one dental object based on the sensor pixel-to-standard-unit ratio and the image metadata. Any combination of the following proposed measurement (calibration) approaches may be used (depending on the desired accuracy and available data).

A first example of a measurement (calibration) process that does not rely on a dedicated non-dental (i.e., an artificial object that is not part of the naturally occurring dental structure of a person) is the known sensor measurement process. Under this proposed process, deriving the sensor pixel-to-standard-unit ratio using the selected at least one measurement process may include determining a sensor type for the source radiographic image data, determining sensor characteristics based on the determined sensor type, determining pixel dimensions for the source radiographic image data, and deriving the sensor pixel-to-standard-unit ratio based on the determined sensor characteristics and the determined pixel dimensions for the source radiographic image data.

A second example of a measurement (calibration) process is the oral structure measurement process. In this proposed approach, deriving the sensor pixel-to-standard-unit ratio using the selected at least one measurement process may include identifying, from the source radiographic image data, teeth without restorations, determining distances in pixels between mesial and distal Cemento Enamel Junction (CEJ) points for the identified teeth, deriving a plurality of pixel-to-standard-unit ratios using the determined distances in pixels and based on pre-determined standard average distances between the mesial and distal CEJ points for each of the identified teeth, and computing an average pixel-to-standard-unit ratio from the derived plurality of pixel-to-standard-unit ratios.

A third example of a measurement process is the 3D surface data measurement process. In this proposed approach, deriving the sensor pixel-to-standard-unit ratio using the selected at least one measurement process may include determining one or more outer borders for respective one or more dental objects appearing in the source radiographic image data, and comparing the one or more outer borders to 2D projections in a projection dictionary, the 2D projections being at incremental distance and angles generated from 3D dental image data, to identify a match between the one or more outer borders and the 2D projections in the projection dictionary. The proposed third example measurement process further includes estimating a viewing angle at which the source radiographic image data was obtained based on the identified match between the one or more outer borders and the 2D projections in the projection dictionary, and deriving the sensor pixel-to-standard-unit ratio based on the estimated angle at which the source radiographic image data was obtained.

A fourth example of a measurement process is the known implant measurement process. In this proposed approach, deriving the sensor pixel-to-standard-unit ratio using the selected at least one measurement process may include detecting an implant structure appearing in the source radiographic image data, and determining implant attributes based on the source radiographic image data for the detected implant structure. The proposed fourth example measurement process further includes comparing the determined implant attributes for the detected implant structure to stored implant attributes included in implant data records, maintained in an implant structure database, for known manufactured implants to identify a match between the determined implant attributes and the stored implant attributes included in the stored implant data records. The fourth approach also includes deriving the sensor pixel-to-standard-unit ratio based on stored geometrical information associated with a selected one of the implant data records that most closely matches (e.g., based on some similarity or mathematical distance criterion) the implant attributes determined from the source radiographic image data.

A fifth example of a measurement process is the implant angle measurement process. In this proposed approach, deriving the sensor pixel-to-standard-unit ratio using the selected at least one measurement process may include detecting an implant structure appearing in the source radiographic image data, determining implant attributes based on the source radiographic image data for the detected implant structure, and comparing the determined implant attributes for the detected implant structure to stored implant attributes included in implant data records, maintained in an implant structure database, for known manufactured implants to identify a match between the determined implant attributes and the stored implant attributes included in the stored implant data records. The fifth proposed approach also includes determining an outer border for the detected implant structure appearing in the source radiographic image data, comparing the outer border to 2D projections maintained in a projection dictionary, the 2D projections being at incremental distance and angles generated from 3D dental image data, to identify a match between the outer border and the 2D projections in the projection dictionary, estimating a viewing angle at which the source radiographic image data was obtained based on the identified match between the outer border and the 2D projections in the projection dictionary, and deriving the sensor pixel-to-standard-unit ratio based on the estimated angle at which the source radiographic image data was obtained, and based on stored geometrical information associated with a selected one of the implant data records that most closely matches the implant attributes determined from the source radiographic image data. In some examples of the fifth proposed approach, deriving the sensor the sensor pixel-to-standard-unit ratio may include estimating viewing angles for other dental objects detected in the source radiographic image data based on a position of the implant structure relative to the other dental structure and based on the viewing angle at which the source radiographic image data was obtained, and deriving the sensor pixel-to-standard-unit ratio based on the estimated viewing angles for the other dental structures detected in the source radiographic image data, and based on the stored geometrical information associated with the selected one of the implant data records that most closely matches the implant attributes determined from the source radiographic image data.

In some embodiments, the procedure 800 may further include determining a treatment plan to treat the identified at least one abnormal dental feature based on the derived severity metric. Determining the treatment plan may include determining based on the derived severity metric whether to approve a dental-care-provider treatment plan submitted by a dental-care provider.

Fraud and Clinical Data Integrity Detection Framework

As noted, in some embodiments, utilization integrity detection approaches are implemented using, for example, multisystem machine learning to identify anomalous or suspicious dental records (e.g., to identify suspicious data records representative of treatment utilization plans submitted by dental-service providers). Integrity detection is applied to data associated with utilization of services such as healthcare services in general, and dental services in particular. The healthcare services can include other services such as specialty services, therapies, and so on. As will be discussed in greater detail below, the integrity detection seeks to evaluate, among other things, whether reported treatment clinical data accurately reflects that treatment for an individual was indicated, and that an appropriate treatment was provided to the individual. The analysis of the treatment clinical data further seeks to identify utilization anomalies. The utilization anomalies include manipulated data, duplicated data, and other threats to utilization integrity. The manipulated and the duplicated data include manipulated dental images and duplicated dental (oral) images, respectively. The identification of manipulated or duplicated clinical data is generally not obvious or easy to detect. While an image that can be provided for clinical data may be uploaded more than once in error, an image for one individual might be presented as an image for a second individual. Further, data such as image data can be manipulated. The image manipulations can include adjusting image exposure, contrast, highlights, or shadows; flipping an image so that an image of a right side of the individual can be presented as a left side image; scaling of the image so that the image is "zoomed in" or "zoomed out", and so on. While a human observer may be able to notice such data manipulations, analysis techniques based on algorithms or heuristics alone can have great difficulty in doing so. Instead, machine learning techniques are applied to the analysis.

In disclosed techniques, machine learning is accomplished using one or more machine learning systems (such as those described above in relation to FIGS. 1-18), including based on different types of neural networks. The neural networks can include generator neural networks and discriminator neural networks within one or more generative adversarial networks (GANs). The generator attempts to create data, called synthetic data, which is able to fool the discriminator into thinking that the data is real. The discriminator tries to detect all synthetic data and label the synthetic data as fake. These adversarial roles of the generator and discriminator enable improved generation of synthetic data. The synthetic data may supplement training data labelled by human observers and may be used to enhance training of the machine learning neural networks. The neural networks training can be based on adjusting weights and biases associated with layers, such as hidden layers, within the neural network. The results of the neural network training based on the augmenting with the synthetic data can be used to further train the neural networks, or can be used to train an additional neural network such as a production neural network. The training can be based on determinations that include true/false, real/fake, and other types of outputs (e.g., decision output to indicate approval or denial of pre-approval requests submitted by dental-care providers). Trained neural network can be applied to a variety of analysis tasks including analysis of dental radiographic image data.

Neural networks, such as a convolutional neural network, a recurrent neural network, a feedforward network, a transformer network, and so on, can be used to perform machine learning, deep learning, etc. A neural network for machine or deep learning can be trained by using a machine learning system to process training data. The training data can include one or more sets of training data. The training data comprises "known good" data, where the known good data includes previously analyzed input data and expected results from analyzing the input data (i.e., the "ground truth" data). The known good data is processed by the machine learning system in order to make adjustments such as adjusting weights and biases associated with the neural network. Additional training adjustments to the neural network can be accomplished by applying additional known good data and by making further adjustments to the weights. In embodiments, the training data includes treatment clinical data associated with a plurality of individuals. Such training data includes radiographic data, where the radiographic data includes dental (oral) images such as x-ray image data. The training data can also include historic radiography associated with specific individuals, text-based content included within current images and historic images (the text-based content may be extracted using OCR, and the extracted data provided a text-related ML model), and so on.

Once trained, multisystem machine learning framework described herein is applied to the treatment clinical data for an individual. As will be described in greater detail below, the multisystem machine learning is used to analyze the data to look for a variety of data anomalies. The data anomalies can include treatment outliers, where a treatment outlier can include a treatment which is different from the standard treatment for a disease, injury, and so on. The data anomalies can also include treatment that is determined to be overly aggressive or unwarranted for a given medical condition. The data anomalies can further include indications that an image, such as a radiographic image or x-ray, has been manipulated or duplicated. The data anomalies can include anomalies associated with provider treatments and accuracy.

As noted, the use of radiographic data (e.g., dental x-rays) for both training, and subsequently in runtime to detect anomalous data records, can be facilitated through the image data calibrations and measurement estimation for dental features appearing in image data, according to one or more of the various measurement estimation approaches described above in relation to FIGS. 1-15, and may also include image alignment processing.

The comprehensive multisystem machine learning framework described herein is used for data integrity detection, including for clinical data integrity. The utilization refers to a range of treatments provided to an individual. While the present disclosure focuses on dental-related treatments, it will be appreciated that some of the implementations described herein can be adapted to also analyze treatment data for various other treatments and therapies, including physical therapy for recovery from injury, surgery, or health events such as heart attack or stroke, and so on. Other therapies can include occupational and speech therapies, and "alternative" therapies such as homeopathic medicine, herbal remedies, meditation, and the like. The implementations described herein can also be adapted to process or analyze other types of insurance claims and coverage (e.g., auto insurance claims, real and personal property damage claims, disaster claims, etc.) With respect to the use of the presently described frameworks to analyze dental treatment data, the utilization integrity detection analyzes treatment clinical data for an individual. The analysis seeks to determine whether the treatment offered to an individual—or claimed to have been provided to the individual—was consistent with standard practice for such treatments, and also seeks to determine if the images themselves are anomalous (e.g., they are near duplicates of a previously stored images, or they may have been manipulated in some way). While many physicians, healthcare practitioners and workers, therapists, pharmacists, and others scrupulously report the treatments provided to the individual, others do not. Data associated with a treatment, such as a number of treatments, the aggressiveness with which a condition is treated, images such as radiographic images, etc., can be "juked" or intentionally manipulated to deceive an auditor who would review the treatment clinical data. Phantom treatments provided for phantom diseases can be presented with the intention to defraud. The analysis of the treatment clinical data by the implementations described herein can thus be used to generate scores and metrics that identify phantom claims of disease and treatment, determine treatment or disease "outliers", find overly aggressive treatments, etc.

Machine learning techniques are applied to the utilization integrity detection. The machine learning can be performed on a processor network configured as a neural network. Examples of machine learning system configurations are also discussed above in relation to the calibration processes (e.g., with respect to FIGS. 1A and 1B) and in relation to clinical data analysis (e.g., with respect to FIG. 16). When an ML model are implemented using neural networks, those neural networks use data processing nodes interconnected by links (arcs) used for data transfer and communication between and among the nodes. To accomplish machine learning, the neural network must first be "trained". As discussed herein, training of a neural network can be accomplished by providing ground truth data (also referred to as "known good" data) to the neural network, where the ground truth data includes input data and verified inferences associated with the data, and supplemental synthetic training data. It is to be noted that the training of machine learning model can also be performed using self-supervised models that need little training data and create results by leveraging vast unlabeled data. Parameters associated with the neural network, such as weights and biases, are adjusted so that the neural network that is being trained makes the verified inferences about the data. Successful training of a neural network typically requires large amounts of training data to improve the success rate of correct inferences. For the example of utilization integrity detection, the training data can be based on treatment data associated with a large number of individuals. The training data may contain manipulated images as well as proper or unaltered ones, false and true reports of treatments, and so on. The training data includes treatment data, radiographic images such as oral x-rays, etc. Once trained, the machine learning is applied to actual data. The "learning" functionality of the ML implementations may continue (intermittently) as the additional data is processed. The neural network is adjusted or "learns" so that the accuracy of the analysis increases, and inference convergence by the neural network is hastened.

Treatment clinical data can be obtained from a system which includes data associated with the individual, treatment data, and so on. The treatment data generally comprises radiographic data. The radiographic data can be obtained using ionizing and nonionizing radiographic techniques. The obtaining further includes obtaining data from one or more additional utilization systems concerning the individual. The additional utilization systems can include insurance provider systems, healthcare provider systems, databases such as medical or dental databases, etc. As will become apparent below, one or more review metrics for an individual are generated, where the review metrics are based on radiographic data analysis (e.g., performed by an ML implementation). The analysis of data can include determination of whether the underlying data is itself compromised (i.e., the data is fraudulent). Examples of compromised image data include radiographic data that has been manipulated, represents duplicate data, and the like, and may thus be associated with a fraudulent claim. Review metrics correspond to analysis result of the necessity (justifiability) of certain clinical treatment procedures. In some instances, a utilization system score is computed, based on data from at least one of the one or more additional utilization systems (the utilization system score may be determined independently of the review metrics). Examples of the system scores include metrics, where the metrics can include an outlier metric, an aggressiveness metric, etc. A composite utilization system score can be derived based, for example, on a weighted average of the outlier metric and the aggressiveness metric. A provider score (also referred to as a clinical data score) is calculated, based on the review metric and the utilization system score. The clinical data score can be used to determine if the clinical data associated with an individual indicates outlier treatment, overly aggressive treatment, etc. An ongoing analysis of the treatment clinical data is performed, based on additional treatment clinical data for the individual. The additional treatment data can include data from a plurality of individuals, longitudinal treatment data for the individual, etc. Additional radiographic data used in the data processing and analysis can be obtained for a plurality of other individuals while undergoing commensurate treatment to the individual. The commensurate treatment can include surgeries, implants, fillings, etc. The additional radiographic data can be taken from the individual while the individual is undergoing different treatment from a treatment indicated by the treatment clinical data. The additional treatment clinical data associated with the individual can be taken from a prior or subsequent dental experience. The ongoing analysis is performed in real-time or near real-time.

Figure 19:
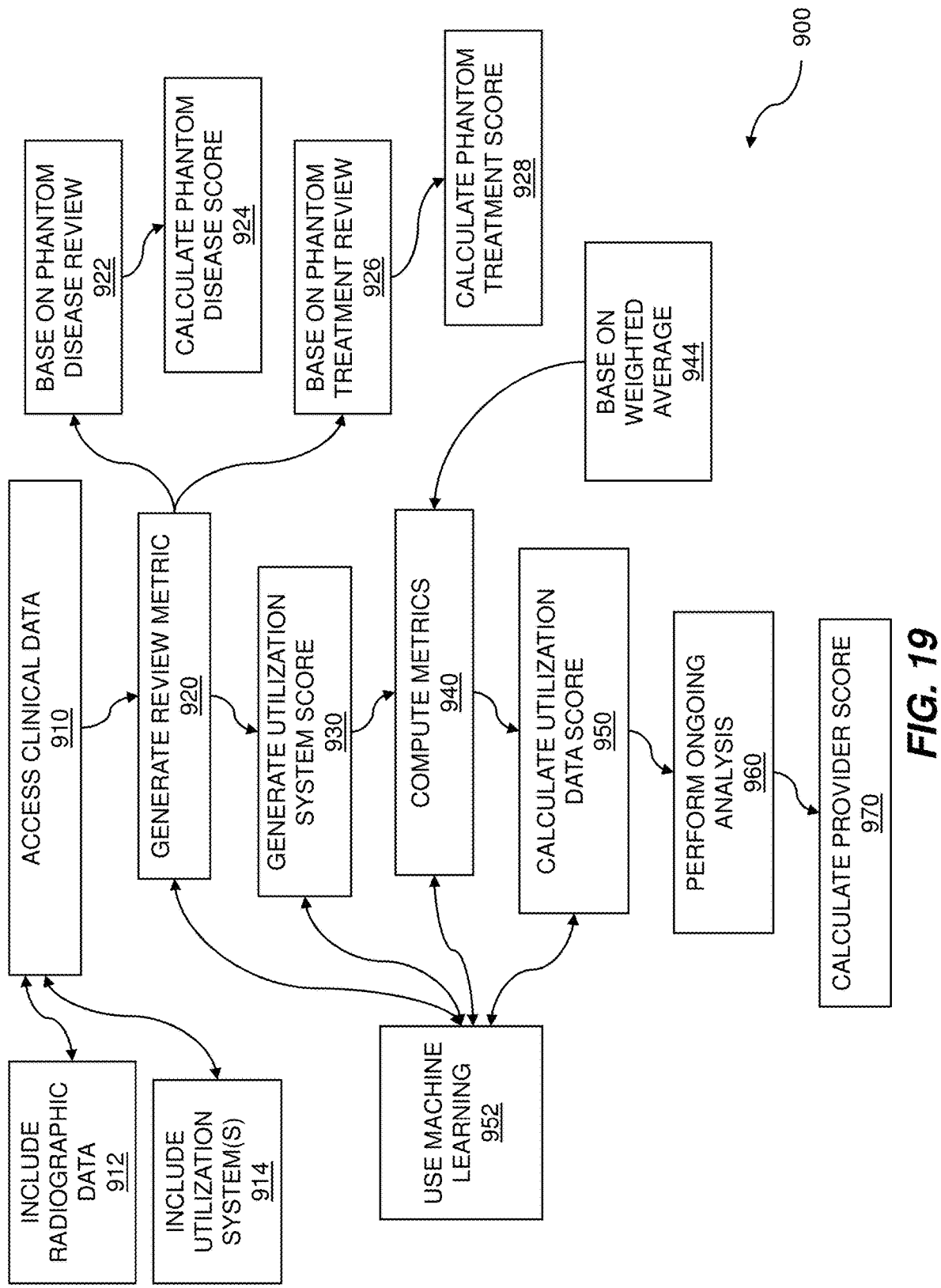
FIG. 19 is a flow diagram for multisystem machine learning for clinical data integrity analysis.

Thus, with reference to FIG. 19, a flow diagram 900 to illustrate example operations of a multisystem machine learning framework to perform clinical data integrity and fraud analysis is shown. The flow diagram 900 is based on a computer-implemented method for integrity and fraud analysis, where the clinical-related analysis can be performed on one or more treatments provided to an individual. As illustrated, the flow 900 includes accessing clinical data 910 for an individual. The clinical data can include various types of data associated with one or more treatments provided to the individual. When applied to dental related data analysis, the clinical data includes dental treatment plans, various records and information recorded during dentist appointments (including the dental-care providers' notes) for an individual, relevant supporting materials such as one or more radiographic images, etc. Additional data that may be relevant to the analysis of the dental-related data, or that may be processed to determine utilization integrity metrics for non-dental treatments, may include data pertaining to inpatient or outpatient treatments such as surgeries or nonsurgical procedures, therapies such as physical, occupational, or speech therapy, data collected or obtained for the individual for general internal medicine or specialist medicine treatments, and so on. It is to be noted that an individual's utilization data may be generated at a provider's location, and transferred directly to a centralized network node(s) on which the present proposed framework is implemented. An individual's utilization data may alternatively be transferred to a third-party's (such as an insurance provider) computing system for storage, and later forwarded therefrom (along with collected data for other individuals) to the centralized system (e.g., a cloud server) on which the framework performing the flow 900 is implemented. The centralized system may be operated by a third party performing the data analyses discussed herein for multiple clients (e.g., multiple different insurance providers each servicing multiple patients and/or multiple dental-care providers).

As further shown in the flow 900, the treatment clinical data comprises radiographic data 912. The radiographic data can be based on data collected using ionizing or nonionizing radiation. The radiographic data can include x-ray data, computed tomography (CT) data, magnetic resonance imaging (MRI) data, ultrasound (nonionizing) data, etc. In embodiments, the radiographic data comprises oral images of the individual. The oral images can be based on various oral images such as bitewing images, periapical images, occlusal images, and the like. In the flow 900, the accessing may also obtain data from one or more additional utilization systems 914 concerning the individual. The additional utilization systems can include systems associated with insurance providers, healthcare providers, and so on. The additional systems can include scheduling systems to show individual patient appointment schedules, previous and current medical providers, etc.

The flow 900 additionally includes generating 920 a review metric for the individual 920, where the review metric may be based on radiographic data analysis. The radiographic data analysis can include analyzing the radiographic data to identify features within the data, artifacts within the data, and so on. Such features may be indicative of fraudulent behavior. As noted herein, the generating may include a process to calibrate source radiographic images (as more particularly described in relation to FIGS. 1-16) and/or to perform expedited clinical data analysis based, for example, on area-based metrics for features detected in the radiographic images (as more particularly described in relation to FIGS. 16-18). In some embodiments, the generating a radiographic-based metric can be based on identifying anomalies within the data. The review metric can be based on a value, a range of values, a percentage, a threshold, and so on. The metric can be text based, where the text could include "pass" or "fail", "good" or "bad", "OK" or "Further examination needed", etc.

In the flow 900, several processes may be performed to generating the radiographic image data review metric (e.g., in order to detect potential fraudulent claims). One such process includes the phantom disease review (analysis) 922. The phantom disease review can include accessing an insurance database to access provider data, accessing the provider data to access patient data, and accessing the patient data. Accessing the patient data can include accessing patient images, appointment schedules, treatment history, current provider information, previous provider information, and the like. The phantom disease review can be used to determine whether the treatment clinical data indicates that an individual received treatment for a disease that is not presented by the individual. In the flow 900, the radiographic data can thus be processed to calculate (derive), at box 924, a phantom disease review score. The phantom disease review score can be based on a value, a range of values, a percentage, a threshold, etc. The phantom disease review score may, in some situation, also be derived based on detection of duplicate images included within claims or other data submission. It is to be noted, though, that data duplication (particularly image duplication) is typically a separate type of data analysis generally performed independently of phantom disease or phantom treatment reviews.

In some examples, generating (at 920) the review metric may also be derived through phantom treatment review process 926. For the phantom treatment review, the radiographic data is used to calculate (at 928) a phantom treatment review score. As will be described in greater detail below, the phantom treatment review score can be based on a numeric value or evaluation, text, etc. The phantom treatment review score can indicate inconsistent treatment clinical data. The inconsistent treatment utilization can include treatments other than standard treatments, too many treatments, too few treatments, and the like.

In some embodiments, if the output of the process to generate the review metric indicates that potential fraudulent images have been detected (as a result of identifying near duplicate images or possible image manipulation), the flow 900 may terminate at that point without proceeding to the downstream clinical data analysis processes. This is because the identification of potentially compromised image data makes further analysis of the claim unnecessary (because the claim is already found to likely contain fraudulent content).

The flow 900 further includes generating 930 a utilization system score based on data from at least one of the one or more additional utilization systems. The utilization system score can be based on one or more metrics, as discussed below. The utilization system score can be used to evaluate the clinical data, such as the treatment clinical data, and to determine the veracity of the data. In embodiments, the data can include errors such as mislabeled data, treatments entered with the incorrect treatment code, and so on. The utilization system score can be based on one or more values, a threshold limit, a percentage, a probability, an inference, and the like. The utilization system score can be used to identify altered images (such as radiographic images), intentionally misleading data, duplicate data, etc. The utilization system score (computed at 930) can include an outlier metric for the treatment clinical data. The outlier metric can be based on whether treatment clinical data associated with an individual tracks with treatment clinical data of a plurality of other individuals who have been provided a similar treatment, or not (e.g., is an outlier). In some embodiments, the utilization system score can also include an aggressiveness metric for the treatment clinical data. An aggressiveness metric can be based on providing an "aggressive" treatment to an individual when a more conservative or less complicated treatment would have sufficed. The aggressiveness metric can indicate a more extensive treatment, a greater number of treatments, and the like. Further embodiments may also include computing a false representation metric for the radiographic data of the individual based on the dental (oral) images with manipulations that display false representations. A false representation can include an image which has been manipulated to show a treatment that was not performed, an image which has been lightened or darkened, a flipped image, and the like. The false image can include duplicate images.

The flow 900 further includes computing (at 940) metrics. The metrics computed at 940 can be based on a weighted average (derived at 944, as more particularly discussed below) of the outlier metric and the aggressiveness metric described in relation to the operations at 930 of the flow 900). The weighted average can also be based (take into account or combine) other metrics such as a false image metric, a duplicate image metric, and the like.

The flow 900 includes computing (at 950) a clinical data score based on the review metric (derived according to the phantom disease review and the phantom treatment review) and the utilization system score (which can combine metrics derived from the aggressiveness and outlier reviews). The clinical data score, as with other scores, can include one or more values, thresholds, percentages, probabilities, and the like. The clinical data score can be used to compare utilization by an individual to utilization by a plurality of other individuals. The data score can be used to determine whether an individual is receiving more or less treatment for a given condition or disease compared to the other individuals. The clinical data score can be used to determine whether the claims for treatment are fraudulent.

In the flow 900, generating a review metric (as performed, for example, at 920 of the flow 900 of FIG. 19), generating the utilization system score (as performed, for example, at 930), and calculating the clinical data score (as performed, for example, at 930 and 940 of the flow 900) may be performed through machine learning implementations (illustrated at 952). The machine learning implementations at 952 may be realized in a manner similar to the implementations (configuration and architecture) used for the image processing unit 200 of FIGS. 1A and 1B, and/or the dental feature detector 710 (and possibly the area calculator and decision module 720) of the system 100 of FIG. 16. The machine learning implementations at 952 of FIG. 19 can be based on deep learning. The machine learning can be implemented using a network such as a neural network, where the neural network can be trained and optimized to learn to make inferences about the review metric, the utilization score, and the clinical data.

As further depicted in FIG. 19, the flow 900 includes performing (at 960) an ongoing analysis of the treatment clinical data, based on additional obtained treatment clinical data for the individual. The ongoing analysis can be used to identify trends in the treatment clinical data, anomalies in the data, treatment "hotspots" or concentrations (where the concentrations can be associated with an outbreak of a disease), services provided by a provider, and so on. In some embodiments, the additional treatment clinical data for the individual comprises longitudinal treatment clinical data for the individual. The longitudinal treatment clinical data can be based on past treatments and current treatments. The longitudinal treatment data can include images associated with the individual. In embodiments, the dental images comprise current and historic radiography of the individual. In some embodiments, the ongoing analysis can be based on additional treatment clinical data for the individual that is performed in real-time or near real-time. The real-time or near real-time analysis can be used to quickly identify anomalies, outliers, manipulated images, and so on. In some embodiments, the ongoing analysis can be performed autonomously. The autonomous analysis can be accomplished using machine learning (which may also be implemented using machine learning processes similar to those performed at 952) where the machine learning implementation provides progressively improved output for the analysis over time.

The flow 900 further includes calculating a provider score 970 for a treatment provider. The provider score associated with a provider can be compared to the provider scores of a plurality of other providers. The provider score can be used to determine whether the provider is recommending treatments at a rate similar to treatment rates of other providers for a given condition, disease, and so on. The provider score may be derived based on at least some of the metrics and scores computed at upstream modules of the module computing the provider score. However, in some embodiments, the provider score may be determined at an earlier point than that shown in the flow 900, and may be based on fewer or additional metrics and scores derived in accordance with the utilization integrity and fraud detection analysis performed through the flow 900. In the example embodiments described herein, the treatment provider supplies dental treatment to the individual (i.e., the provider is a dental-care provider). However, as noted, the framework illustrated in the flow 900 can be adapted to analyze data for other types of treatments, therapies, surgeries, and so on, and for the respective providers of such other treatments, therapies, surgeries, etc.

In some embodiments of the framework depicted in FIG. 19, some of the processes (including ML-based analyses to detect various features, or to compute various metrics) need to be performed in sequence since the output of some processes is required as input for computation of another process. For example, in some embodiments, detection of outright fraud (e.g., through detection of near-duplicate images and image manipulation instances, as more particularly discussed below) may be performed ahead of other clinical data (e.g., utilization) analysis (to determine clinical necessity or reasonableness of treatment plans). If fraud is detected during this upstream stage of the analysis, there is no need to perform the downstream clinical data analysis (i.e., the medical merits of a claim are irrelevant if the claim is determined to be fraudulent). In another example, computation of the clinical data score is based on a computed review metric and a computed utilization system score. In a similar vein, the provider score is generally dependent on earlier computed metrics (as more particularly discussed with respect to FIG. 21, below) such as the outlier metric, aggressiveness metric, phantom disease score and phantom treatment score. The provider score process is thus located downstream the processes that compute the metrics and scores on which the provider score process depends. Nevertheless, various steps in the flow 900 (or of any of the other frameworks and flows described herein may be changed in order, repeated, or omitted, without departing from the disclosed concepts. Various embodiments of the flow 900 can be included in a computer program product embodied in a non-transitory computer readable medium that includes code executable by one or more processors.

Once predictions resulting from the various models (applied to input radiographic images), various dimensional properties (areas, distances, and ratios) are computed. For example, distances may be derived between various keypoints. In some embodiments, for each tooth, distances between cej and bone point are computed on both sides, and cej and apex points. These precise computations can be used to indicate if there is bone loss, or there is some other dental abnormality or damage.

As discussed herein, in some embodiments, areas for various dental features are derived. Some examples of dental features for which their areas may be computed include:
   Total area of the region (a line between CEJ's created and above that is the region);
   Areas of decay;
   Areas of fillings; and/or
   Areas missing tooth matter (i.e., broken tooth).

The above example areas can then be used to calculate, for instance, a DMF ratio which is the sum of decay, missing, and filling, divided by the total coronal area. This gives a number in the range of [0, 1], where 0 indicates there is no decay, missing tooth portion, or filling, whereas 1 indicates the entire coronal area is either missing, includes a decaying tooth region, or has a filling. In the event that the models cannot identify (predict) both CEJ's of a tooth, an UNKNOWN decision is returned for the tooth.

Using the above measurements, a decision may be made for a claim or a request for pre-approval that includes one of the following decisions for a claim: Approve, Deny, Review, Downcode, or Request for more information. The decision-making process may be based on an intricate decision tree or algorithm.

Figure 20:
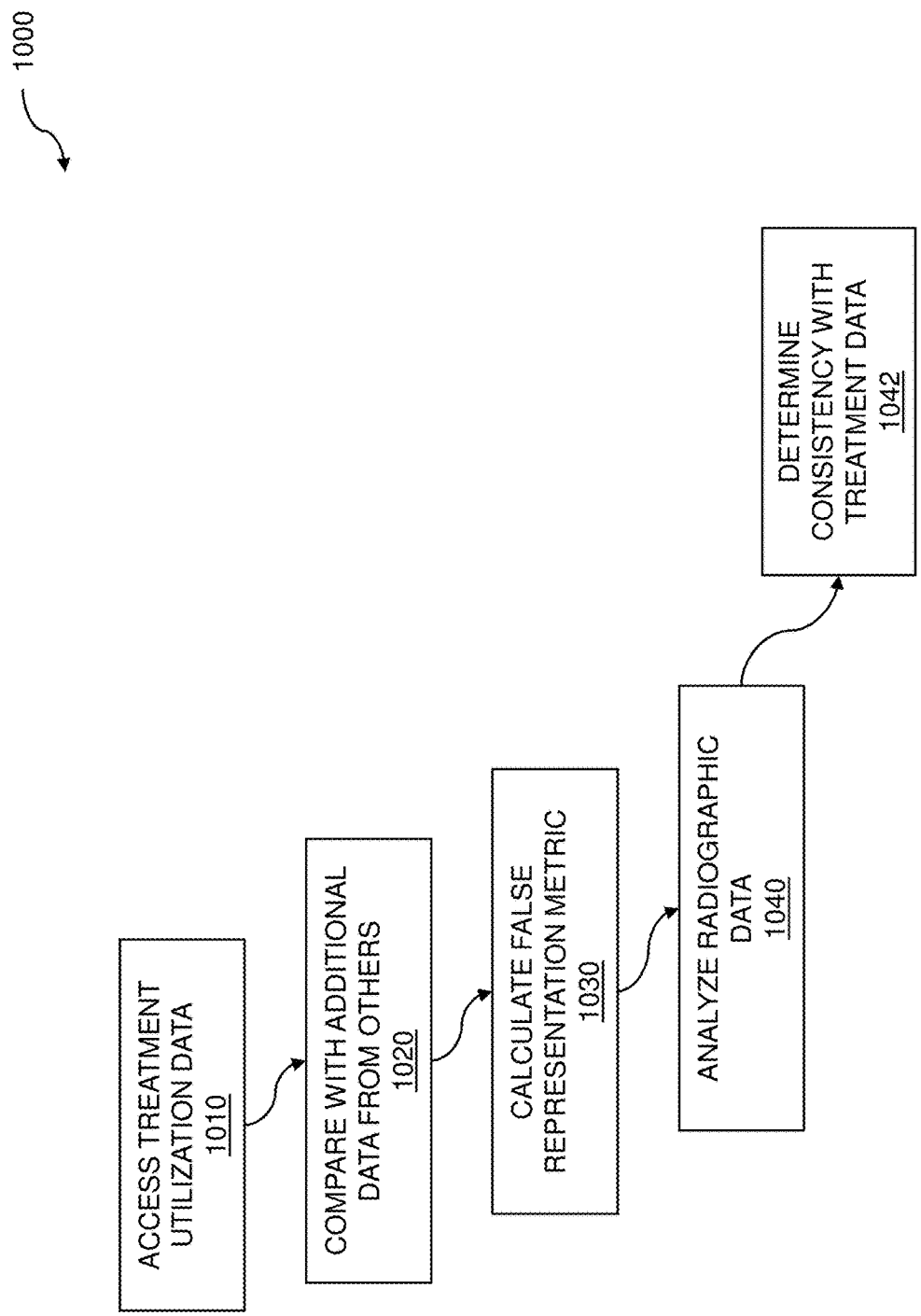
FIG. 20 is a flow diagram for analyzing radiographic data.

With reference next to FIG. 20, a flow diagram for an example procedure 1000 for analyzing radiographic data is shown. Radiographic data, such as x-ray data, can be associated with an individual. The radiographic data can be analyzed to determine whether treatment is needed, which treatment is indicated, and so on (this can also include the processes discussed above in relation to FIGS. 16 and 18). The analysis of the radiographic data can also be used to determine whether false representations are being made, whether inappropriate treatments are being recommended by a provider, and so on. The analyzing of radiographic data can be performed by machine learning implementations, and can be used in conjunction with, or as part of, the analysis performed in the example flow 900 of FIG. 19. Analysis of radiographic data enables multisystem machine learning for utilization integrity detection.

More particularly, the flow 1000 includes accessing treatment clinical data 1010 for an individual. The treatment clinical data can be accessed from one or more databases, where the databases can be associated with one or more utilization systems. The databases can include local databases, remote databases, cloud-based databases, mesh-based databases, etc. The treatment data can also be communicated directly from the dental-care provider (via a network such as the Internet) to a centralized system without being first stored in any intermediate or third-party database. The treatment clinical data can include various data types such as image data, text, audio data, video data, and the like. The radiographic data can include x-rays (namely, dental x-rays). Further treatment clinical data, including data from one or more additional utilization systems concerning the individual, can be accessed. The additional utilization systems can include current and previous providers, current and previous employers, and so on.

The flow 1000 further includes comparing (at 2020) the radiographic data 220 with additional radiographic data from a plurality of other individuals. The radiographic data can include data generated using ionizing and nonionizing radiation sources. The radiographic data can include x-ray images, computed tomography (CT) images, ultrasonic images, and so on. In embodiments, the additional treatment clinical data can be taken from a prior dental experience or a subsequent dental experience. The additional radiographic data can be obtained from other individuals. In embodiments, the additional radiographic data can be taken from the plurality of other individuals undergoing commensurate treatments to that performed on the individual. The commensurate treatment can include restorations (i.e., fillings), fitting of implants, surgical procedures, etc. In further embodiments, the additional radiographic data can be taken from the individual while the individual is undergoing different treatment from a treatment indicated by the treatment clinical data. In a usage example, the individual can be undergoing a filling while the treatment clinical data indicates that a root canal procedure was performed. In embodiments, the radiographic data from the plurality of other individuals includes oral images from the plurality of other individuals. The oral (dental) images can include bitewing images, periapical images, occlusal images, etc. For example, the dental (oral) images from the plurality of other individuals can include oral images with manipulations. Discussed throughout, the oral images with manipulations can include images that have been lightened or darkened, scaled images, flipped images, and the like. The dental images with manipulations can display false representations. The false representations can include treatments that were not performed, conditions (medical or dental conditions) not presented by the individual, etc.

The flow 1000 further includes calculating 1030 a false representation metric for the radiographic data of the individual based on the oral images with manipulations that display false representations. The false representation metric can be based on a value, a range of values, a threshold, a probability, an "x out of 10" or similar evaluation, and so on. The false representation metric can be derived based on a derived outlier metric (as described in relation to the flow 900 of FIG. 19), an aggressiveness metric, a phantom disease review score, and the like. The false representation metric can be used to evaluate a likelihood that an image such as an oral image is a false image, a manipulated image, a duplicate image, etc.

The flow 1000 further includes analyzing 1040 the radiographic data of the individual to determine consistency with other individuals' radiographic data. Determining consistency with the individual's other radiographic data can include determining whether implants, fillings, bridges, or other treatments that have been provided to the individual in the past are still evident in the oral images or are absent due to treatments such as extractions. In embodiments, the analyzing can include phantom disease review. Phantom disease review can be used to determine whether a disease or condition is presented in an image but is not actually presented by the individual. In further embodiments, the analyzing can include phantom treatment review. The phantom treatment review can be used to determine whether a treatment that is shown in an image was actually provided to the individual. In a usage example, an image can be manipulated to show a filling, where a filling was not actually provided to the individual. In other embodiments, the phantom treatment review score may indicate inconsistent treatment clinical data. Inconsistent clinical data can include showing that a treatment such as an implant was previously provided, and that the same treatment was provided again.

The flow 1000 further includes determining (at 1042) consistency with treatment data. Determining the consistency of the treatment data can include determining consistency with other individuals' radiographic data. The consistency of the treatment data can include determining that a treatment such as a cleaning is provided once, twice, or more times per year based on a patient's clinical data and physician, dentist, or other recommendations. Determining consistency can be based on standard treatment practice, overly aggressive treatment, and the like.

Various steps in the flow 1000 may be changed in order, repeated, omitted, or the like without departing from the disclosed concepts.

Figure 21:
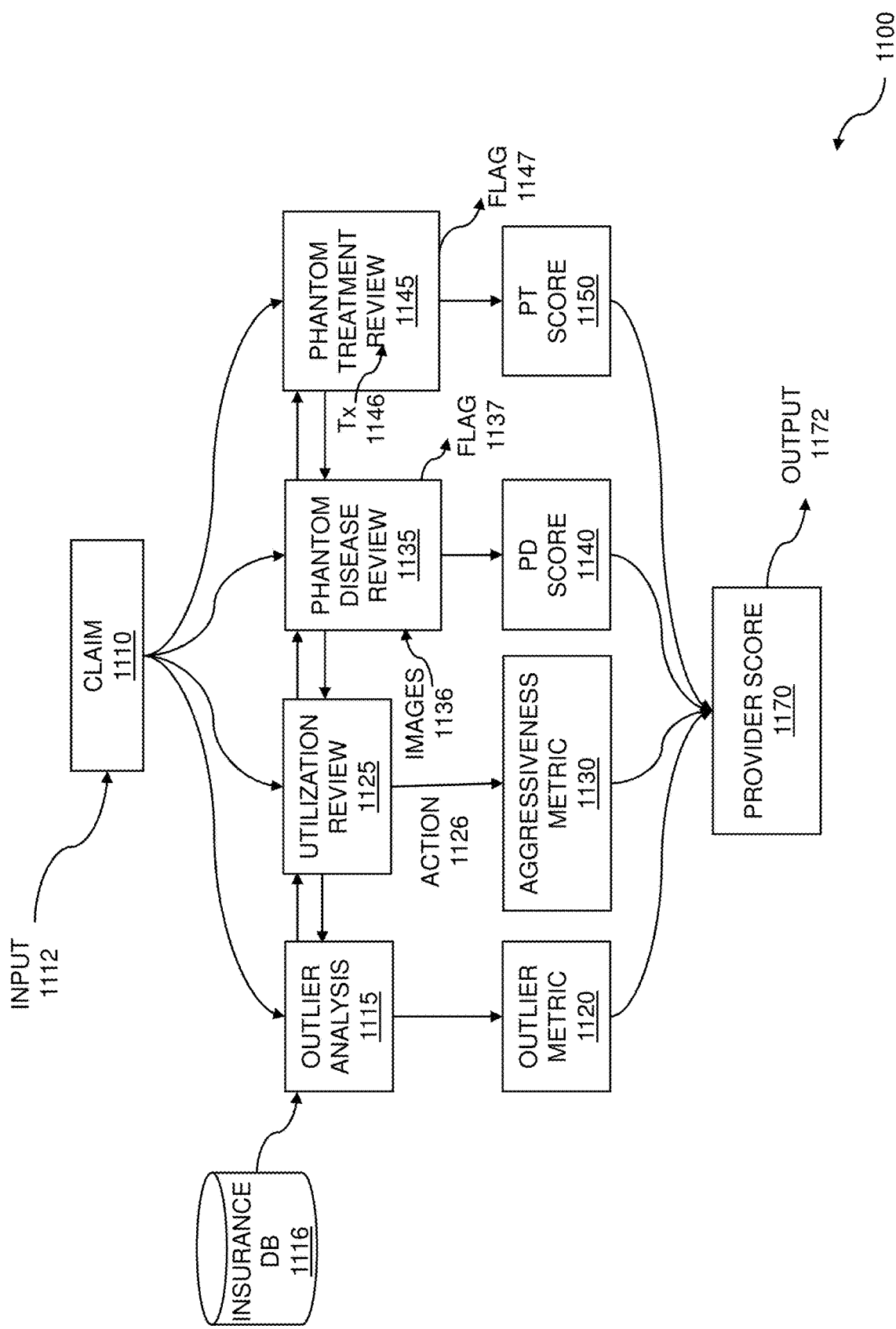
FIG. 21 is a flow diagram for a provider score determination process.

With reference next to FIG. 21, a block diagram depicting a framework 1100 of processes for computing a provider score is shown. A provider score can be determined for a provider who provides services, treatments, and so on to an individual. The provider score can be used to determine an accuracy for utilization integrity of the provider. The provider score can be used to identify provider treatment clinical data reporting statistics or trends. The provider score can also be used to compare a given provider with a plurality of other providers to determine whether the treatments or services provided by the provider are consistent with accepted practice. Determination of the provider score can be used by a multisystem machine learning framework for utilization integrity detection. As also discussed in relation to FIG. 19, treatment clinical data for an individual is accessed, where the treatment clinical data comprises radiographic data and data from one or more additional utilization systems concerning the individual. A review metric is generated for the individual, where the review metric is based on radiographic data analysis. A utilization system score is generated based on data from at least one of the one or more additional utilization systems.

More particularly, as shown in FIG. 21, a claim record is received (at 1110) by a system (realized, at least in part, using one or more ML engines) implementing the procedure 1100. A claim record can include an insurance claim for a service or treatment provided by a provider, and may also correspond to a request for pre-approval of a proposed treatment plan. The claim can be initiated based on input 1112, where the input can include a type of service, a name of an individual who received the service, a date of the service, a cost of the service, and so on. Various analyses, processes, and reviews can be performed on the claim in the course of determining a provider score.

One example process includes an outlier analysis 1115 (which may be similar to the outlier analysis briefly discussed above in relation to the operation 930 for generating a utilization system score). The outlier analysis can analyze whether the claim is within an appropriate range of values, below a threshold, etc. An appropriate range can be based on standard practices associated with the treatment. The outlier analysis can be based on data obtained from an insurance database 1116. The insurance database can include treatment data for a plurality of individuals who have received a given treatment. Further data within the insurance database can include provider data, standard or typical treatment costs, a provider "watch list" for unscrupulous providers, etc. In embodiments, the outlier analysis can produce an outlier metric 1120 for the treatment clinical data. The outlier metric can include a range of values, a threshold, a percentage, a ranking, and the like. In some embodiments, the outlier metric (score) may be computed as the Weighted Moving Average (WMA) of weights applied to individual dental ratios categorized by upcoding, unbundling (e.g., instead of charging for one procedure, charging for multiple procedures), and overutilization. Computation of the outlier score can include an analysis of the number of procedures performed, by the particular provider, for a particular patient, and how much was charged for the particular patient.

The framework 1100 for determining the provider score may further include a utilization review 1125. The utilization review can be used to determine a frequency of treatment received by an individual, a frequency of a given treatment provided by the provider to a plurality of individuals, and so on. The utilization review process can calculate or generate a utilization system score. In embodiments, the utilization system review can identify an action 1126, where the action can include an action taken by an insurance provider (e.g., accept a claim, deny a claim, or partially deny a claim).

The utilization review can also determine an aggressiveness metric (at 1130). The aggressiveness metric, representative of how aggressively a given provider provides a particular treatment, is computed based, in part, on the output of the utilization review 1125 (e.g., based on the determined action 1126). In some examples, the aggressiveness metric is determined by how many claim lines do not meet insurance guidelines. The input for this review is the claim with supporting materials attachment. The system implementing the flow 1100 is configured, as part of the utilization review process 1125, to process received image data (through an appropriate ML model) and any text-based content such a provider's narratives (e.g., using natural language processing) to determine whether the claim 1110 meets insurance guidelines. For example, for a D4342 procedure (see Appendix A, below), one tooth needs to have bone level greater than a specific threshold or presence of subgingival calculus (Appendix A, provided below, includes example procedure codes and descriptions that may be used in the performance of a clinical data analysis as discussed in relation to the process 1125 of FIG. 21, or the procedure 800 of FIG. 18). The ML model to process radiographic image data to compute a utilization score (which may include the processing described in relation to the system 700 and the procedure 800) can identify relevant dental features in the radiographic image data, and determine the bone level of the affected tooth to thus determine whether the threshold and criteria are met. This results in an acceptance or denial of claim. The percentage of denials is then used to determine the aggressiveness metric. An example formulation to compute an aggressiveness metric is the following:

> Aggressiveness score=WMA(*based on time) moving average based on extent of denial ratio*procedure_weights*(1−claims_threshold)

In the above formulation, the denial ratio is computed as the ratio of the number of denials (for a particular provider in the present instance, or over some period of time) to the number of claim line reviews.

As additionally depicted in FIG. 21, the provider score determination can include a phantom disease review process 1135. The phantom disease review can determine whether a claimed disease is in fact indicated by data such as radiographic data. The phantom disease review can be performed on images 1136, where the images can include oral (dental) radiographic images for the particular individual associated with the claim record 1110. The oral images can also include current and historic radiography of the individual, oral images from the plurality of other individuals (retrieved from a database of images), and so on. The phantom disease review can generate a flag 113)7. The flag 1137 can be used to indicate that a phantom disease has been found or is suspected based on the review. For provider score determination, the radiographic data is used to calculate a phantom disease review score 1140 (this may be performed in a manner similar to the process described in relation to the operations 922 of FIG. 19). The phantom disease review score can be based on whether a particular disease or diseases are indicated by the radiographic data, or not. In embodiments, the phantom disease review score can include duplicated treatment clinical data. The duplicated treatment clinical data may have been entered accidentally or purposefully.

The phantom disease review score thus represents an indication of a provider's billing for procedures where a disease (dental condition) was not present. The input for this review also includes provider and patient history databases which have past claims and current images (and other current information, such as chart data, and claim data). One analysis performed in the course of the phantom disease review is to determine whether the image(s) associated with the claims being processed have been modified (manipulated or tampered) by the provider.

The objective of the image manipulation detection review is to find out the images that are tampered (e.g., using an image editing tool). To determine whether an X-ray image was tampered, the image data (and possibly its metadata, for intraoral image) is analyzed. Examples of manipulation instances are the following:
1. Inpainting: In this manipulation, a region of an X-ray is reconstructed or unwanted parts of an X-ray image are overwritten. For example, increasing the depth of tooth decay using photoshop etc.
2. Copy-move: Copying a patch from an X-ray image and pasting to another region. This can potentially happen in many ways. For example, a tooth/part of a tooth can be copied and pasted to another tooth or bone level can be changed in a similar manner.
3. Splicing: In this case, an image patch is copied from another image. For example, a tooth can be copied from another image to hide something in an X-ray, or to show that there is a problem on a tooth which needs to be treated etc.

Detection of potential instances of image manipulation may be performed, for example, by inputting a copy of the current source radiographic image data into an ML model configured to identify potential regions in the image that may have been manipulated. In some embodiments, the ML-based implementation may be configured to detect manipulation using dental treatment history for the particular patient associated with the submitted claim. Thus, an ML engine may be trained to detect image manipulation (e.g., as part of a phantom treatment review analysis) using data from the current image and an archival image for the patient. The ML engine may be configured to flag potential regions of difference between the current and archived radiographic image that are consistent with certain types of image manipulation. Consider the following three (3) examples:

A tooth is tampered in a way that it has an additional treatment. For example, there is root canal treatment visible in a first, earlier, image (T1) which cannot be seen in the current (future) image (T2) that includes image data for the tooth being analyzed. In some embodiments, the analysis may be performed by applying a dental feature detector (which may be similar to the detector 710 of FIG. 16) to generate text-based labels (and/or additional representations) identifying the affected tooth and the treatment performed on it. The generated labels may then be compared to previously produced labels (e.g., represented as binary variable for each tooth and/or each treatment) for archived images. Alternatively, the labels for archived images may be generated contemporaneously.
1. A tooth has the treatment which can be seen in both T1 and T2. However, T2 is not consistent with T1 (and should be impossible to happen). For example, both images have root canal, but in T1, the root canal is deeper (longer) than T2 which either indicates some of the filling is removed from the tooth, or there is some forgery. This type of image manipulation may be detected through ML-based image comparison of T1 and T2. The image manipulation analysis may also be performed by taking into account identified landmarks within the image that indicate relative positioning and orientations of the various dental features. The detection of landmarks (e.g., by an ML model to detect various dental features or landmarks) can increase the confidence in the detection of potential manipulation since the detection is not strictly based on deriving feature size or length (e.g., in mm), but instead also provides relative positioning information (e.g., does the root canal beyond a certain detected landmark).
2. The X-ray belongs to another patient. Regardless of whether dental treatment history matches, the teeth may be different (different shaped teeth, different angles between teeth (i.e., more than ε°), etc.) Detection of this type of manipulation may be performed based on a structural fingerprinting for the oral structure of the patient (e.g., tooth1 is associated with a characteristic (fingerprint) record, or characteristic vector that may include information such as: {angle: ⟨°, height: h mm, width: w mm, CEJ, other descriptive parameters}).

Figure 26A:
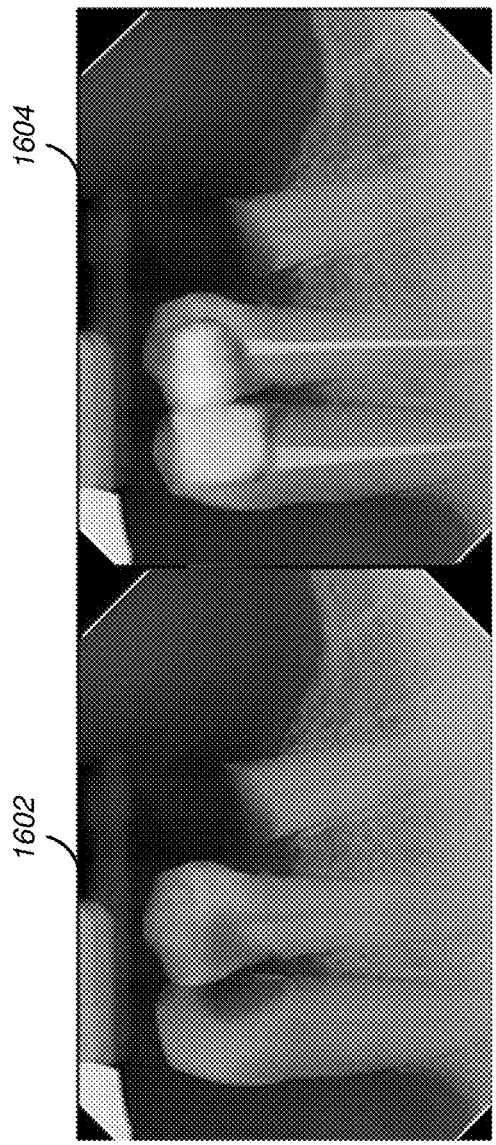
FIGS. 26A-B include examples of potential tampered dental radiographic images.

In some embodiments, image tampering detection can be implemented based on the heuristic that two x-ray images that are submitted before and after treatment (possibly taken a few weeks apart) are extremely unlikely to be the same orientation, angulation, etc., with the exception of the treatment (i.e., it is unlikely that two images of the same dental object will only be different in the purported treatment performed on the dental object; rather, a positioning and perspective mismatch between the two images is expected). For example, and with reference to FIG. 26A, example pre- and post-treatment x-ray images matches 1602 and 1604 are shown, in which no geometrical mismatch (transformation) is apparent. As seen the biting block and the teeth, bone structure, even the random artifacts are exactly the same. The possibility of this happening is extremely unlikely, and thus the root canal treatment and the fillings on top of the two left teeth are likely to have been the result of image tampering (i.e., via photoshop or other photo editing tools).

Figure 26B:
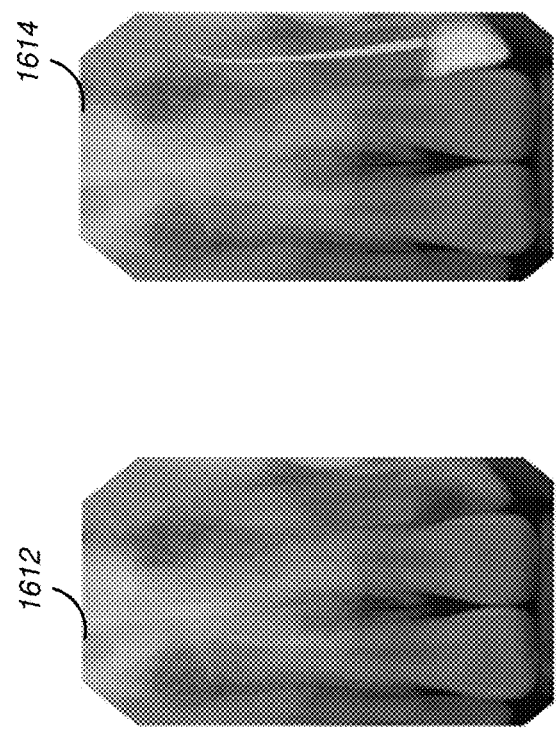

Consider another example, as provided in FIG. 26B, showing pre- and post-treatment x-ray images 1612 and 1614. In investigating the post-treatment image investigation of the post-images using digital forensics tools reveals that the post-treatment image is possibly manipulated. In some embodiments, tampering detection is based on blind classification of an image to determine if an image is manipulated using a DNN architecture. Output of such a classifier can identify which pixels are potentially manipulated.

In some embodiments, a digital image forensics method can be used for image tampering detection. These methods can use conventional image processing methods such as detecting the inconsistencies through JPEG compression artefact or through noise level analysis across an image. It can also use a deep neural network such as a CNN based architecture to detect anomalies within an image.

In some embodiments, the methodology of image tampering detection may be a classification method which may indicate whether an image is tampered or not. Such methods may have a confidence score between 0 and 1 which is an indication of how likely a given image is manipulated. A score of 0 indicates that image tampering has almost certainly not occurred, whereas a score of 1 indicates that there is a 100% confidence level that the image has been tampered with.

In some embodiments, image tampering detections may be implemented through a detection procedure which indicates the regions on an image where tampering has occurred. The detection output can include a bounding box, or may include a segmentation mask that shows exactly which pixels in the image likely have been manipulated.

In some examples, image tampering detection procedures may also identify, as part of the detection process output, the tools that were used for editing the image, such as Photoshop, Paint, Gimp etc. Moreover, the image tampering detection procedures can also indicate image processing methods that an input image may have undergone, including such output indicating Copy-Move Forgery, Impainting, and so on. These tools may use image content or EXIF header (Exchangeable image file format) of the image.

The results of the image tampering detection may be used in Phantom Disease or Phantom Treatment score. This calculation may include the confidence score of the above image tampering detectors. In some cases, this may require an approval step from a professional such as a dentist or computer vision expert who can confirm that there is potential image tampering.

In some embodiments, the results of image tampering detectors may be used to estimate provider score. This calculation may use the frequency of images which are predicted as tampered, the confidence score of each prediction, whether it is confirmed by an expert, and so on.

Having determined potential instances of manipulated images, an example formulation for the phantom disease score is: PD score=WMA of #phantom disease claims, where the number of phantom disease claims may be the sum of detected instances of claims (submitted for a particular one or more providers) with supporting images that are likely manipulated images. The phantom disease score, which may be computed for particular providers, can capture the frequency at which phantom diseases are detected.

In some implemen a ions, the phantom disease review process and/or the phantom. treatment process may also include duplicate detection or near duplicate detection analysis. The findings of these analyses may be used to calculate a provider score. The duplicate and near duplicate detection may be performed independently of the provider score analysis, e.g., as an initial step to assess potential fraudulent claims. The duplicate or near-duplicate analysis yields a duplicate score, indicative of a likelihood that a currently submitted image is a duplicate of a previously submitted image (for the present patient, or for a different patient). The goal of the duplicate detection review may be to determine if a claim has been submitted before or may be to detect if a phantom disease was added for a patient. Alternatively, it may be to detect if a phantom treatment was performed for a patient. Detecting this may not be straightforward as images can be compressed, geometrically transformed (such as resizing, cropping, or flipping), printed and scanned, etc. In such cases, although the claims are perceptually very similar, how they are stored in the disk may be completely different which requires a deep investigation. An example process for a near duplicate search process is the following:

1. Feature extraction: Using a convolutional neural network (CNN)-based implementations or another deep neural network architecture to create one or more feature sets for each image. It can also use computer vision (CV) techniques such as scale-invariant feature transform (SIFT), speeded up robust features (SURF), Oriented FAST and rotated BRIEF (ORB) to create a set of feature descriptors from each image. Linear Discriminant Analysis (LDA) may be used as a post processing step for these descriptors. This functionality aims to decrease the dimensionality of the feature descriptors while increasing the separability of them from each other. In other words, similar descriptors will have higher similarity scores whereas different features will have lower scores.

2. Extracting signatures from images (using the extracted features): Many feature descriptors will be created for each image. For each of these feature descriptors, a signature is created. Additionally or alternatively, the feature descriptors may be aggregated in order to generate an aggregate signature.

3. Creating signature database (i.e., indexing): A process that will create signatures from all X-ray images and then index those signatures with the corresponding unique image. Each image may have multiple signatures.

4. Searching query images in the database: This step searches for images that are very similar to source image for which the near duplicate processing is being performed. Two example ways to do this include:
   a) Linear search (pairwise similarity): Under this approach, the signatures of each of an image are compared to the signatures stored in a database. This approach is computationally costly because it requires each signature to be compared with all the signatures in the database.
   b) Approximate nearest neighbor search (multi-wise similarity): Suppose that the database contains n images. Under this approach, rather than comparing the query image with all n images contained in the database, the most similar r of them can efficiently be returned.

5. Comparing query images with the images with high similarity score: The searching step returns r most similar images for approximate nearest neighbor search. Some of those images may not be the same image but very similar ones to the queried image (i.e., they are false positives). The comparing step goes through those near duplicate images and filters out those that do not match to identify a true actual copy. In this step, each feature point of the query image can be exhaustively compared with each feature point in the r most similar images. This is a computationally expensive operation. Therefore, a method such as k-nearest neighbor search (knn) or RANdom SAmple Consensus (RANSAC) can be used to compare the query image with similar images.

Turning back to FIG. 21, the provider score determination may also be based on a phantom treatment score that is derived from a phantom treatment review process 1145. The phantom treatment review can be based on the phantom disease review, on treatment (TX) data 1146 associated with a patient x, and so on. The phantom treatment review can be used to determine whether a treatment was provided, whether the treatment was the accepted or standard treatment, and so on. The phantom treatment review generates a flag 1147 that is used to indicate that a phantom treatment is suspected or has been found based on the phantom treatment review. The provider score determination can include a phantom treatment (PT) score 1150 determined based on the phantom treatment review 1145. The phantom treatment review score can be based on a threshold, a value, a range of values, an "x out of y" score, and so on. In embodiments, the phantom treatment review score can indicate inconsistent treatment clinical data. The inconsistent treatment clinical data can indicate too many or too few treatments, an incorrect treatment, an overly aggressive treatment, and so on. The treatment review score can be based on the type of treatment provided. To determine phantom treatments, patient treatment history may be utilized to determine whether the treatment is shown in future claims. Determination of the phantom treatment score may be based on the formulation of: PT score=WMA of #phantom treatment claims.

The provider score determination can be further based on calculating a provider score 1170 (where the provider is the individual/entity submitting the image), where the provider score can be calculated for a particular treatment provider. The treatment provider can include a physical or occupational therapist, a physician, a specialist, and so on. In embodiments, the treatment provider can supply dental treatment to the individual. The provider score can be calculated based on consideration of the outlier score 1120, the aggressiveness score 1130, the phantom disease review score 1140, and the phantom treatment review score 1150. For example, the provider score may be computed as weighted sum or average of the outlier metric 1120, the aggressiveness metric 1130, the phantom disease score 1140, and the phantom review score 1150, with the weights for each of the score being adjustable weights that can vary based on one or more factors (e.g., the specific provider, the specific insurance company, etc.) The adjustable weight may themselves be derived using, for example, a ML model. Other scores based on other reviews, analyses, calculations, and so on, can also be included in the computation of the provider score, and the provider score may be derived according to various formulations. The provider score can be used to generate an output 1172. The output can include a value, an answer such as "yes" or "no", an approval or rejection to disbursement payment, an approval or rejection of a request for pre-approval, and so on. The output from the provider score determination can be added to or included with the treatment clinical data.

In another example, a provider score (also referred to as a provider risk/concern score, which may be represented as the score 1170, or some other output) may be derived as a number between 0 and 100, where 0 is low risk and 100 is high risk that their claims should be further investigated. In such embodiments, additional analysis modules to analyze data pertaining to claims submitted by a provider include a module (not shown in FIG. 21) of whether a tooth/quadrant/ treatment is not present. When one or more images are submitted for a claim, but they either do not contain the necessary information such as the claimed tooth, or a quadrant (i.e., one of Upper Left Upper Right, Lower Left or Lower Right), or a post-treatment image that does not contain the treatment, those claims are flagged. Another analysis module determines inconsistencies in tooth history. For example, suppose that a patient undergoes multiple treatments and information about some of these treatments is available. The inconsistent history analysis module investigates if future claims contain the old treatments. For example, a patient's upper left wisdom tooth is removed at time 1, but the extracted tooth is nevertheless visible at a later time 2. In this case, either or both of the treatments are flagged.

Figure 22:
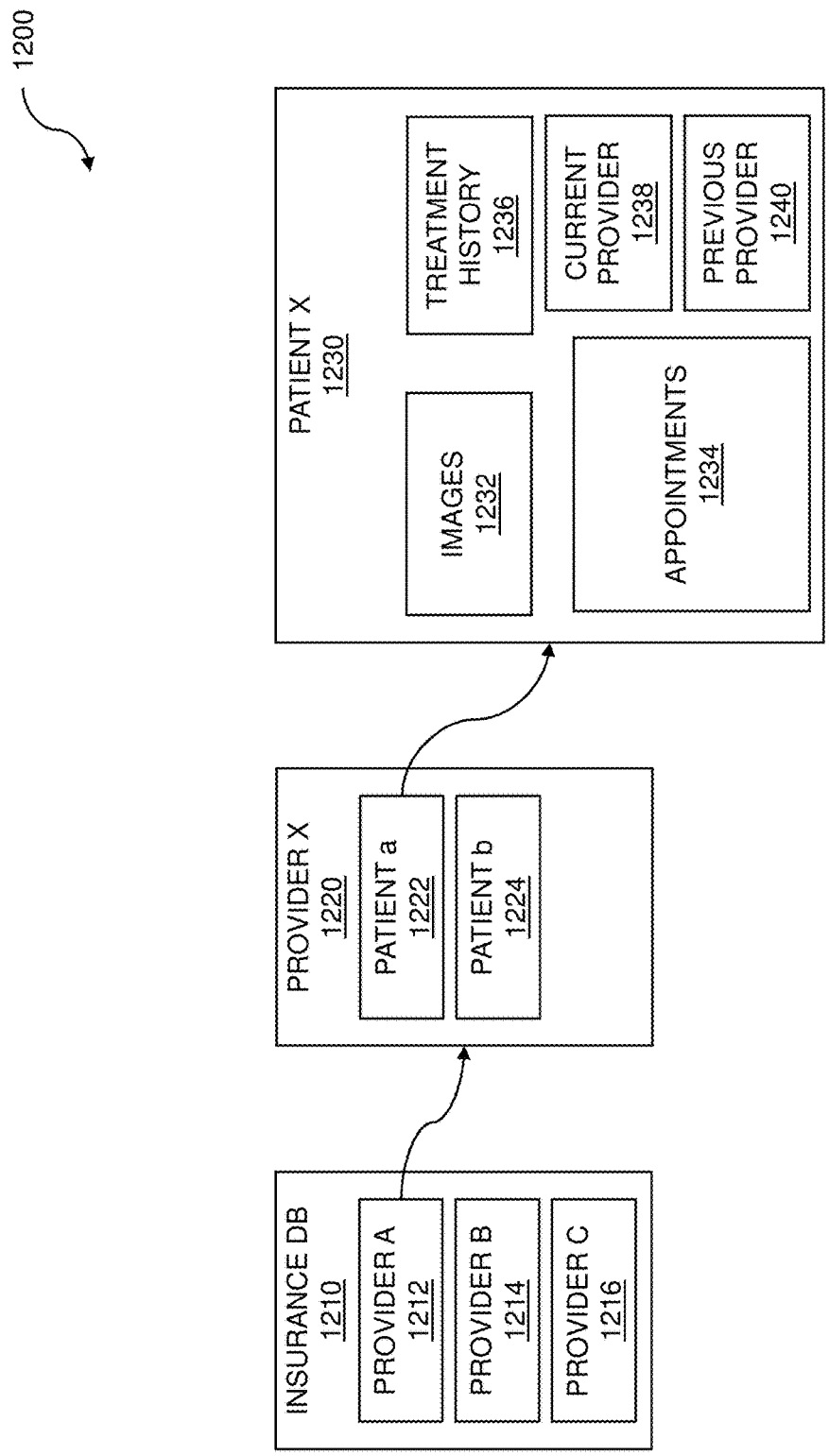
FIG. 22 illustrates data structures accessed in the course of performing a phantom disease review.

FIG. 22 provides further details regarding the phantom disease review process. In order to reduce the risk of making duplicate payments, erroneous payments, and so on, a phantom disease review can be performed. A phantom disease can include a disease that is not actually associated with an individual. A phantom disease claim can be made in a complaint for a patient for a disease or other malady that the patient is not actually experiencing. A phantom disease can result from a provider entering invalid or inaccurate treatment clinical data (in some examples, an error can be the result of data integrity errors introduced by the payer where a wrong attachment(s) is associated with a claim, e.g., where another patient's radiographs are sent). Phantom disease review allows a multisystem machine learning implementation to perform a utilization review and integrity detection analysis. Treatment data for an individual is accessed, where the treatment data comprises radiographic data (and optionally other data from one or more other system collecting data in relation to the individual). A review metric for the individual is generated, where the review metric is based on radiographic data analysis. A utilization system score is generated, based on data from at least one of the one or more additional utilization systems. A clinical data score is calculated, based on the review metric and the utilization system score. An ongoing analysis of the treatment clinical data is performed, based on additional treatment clinical data for the individual.

Phantom disease review can be based on data maintained in insurance databases, provider information, patient information, etc., as more particularly illustrated in FIG. 22. In some embodiments, phantom disease review can include accessing an insurance database 1210. The insurance database can include treatment clinical data provided by one or more providers. The providers can include provider A 1212, provider B 1214, provider C 1216, and so on. While three providers are shown, other numbers of providers can be included in the insurance database. A provider database such as a database for provider x 1220, can be associated with each provider within the insurance database. A provider can provide services such as dental services, or other types of services, such as physical therapy or occupational therapy services, treatments such as medical treatments, and so on. The treatment provider can supply dental treatment to the individual. The dental treatment that is provided can include routine dental treatments such as cleanings and fillings, surgeries such as extractions or fitting of implants, etc. The provider x database 1220 can include treatment clinical data associated with one or more patients. The patients can include patient a 1222, patient b 1224, and so on. While two patients are shown, other numbers of patients can be included.

The phantom disease review can also access a patient database. The patient database (such as database 1230) can include treatment (clinical) data associated with one or more patients such as patient x. Various types of data associated with a patient can be included in the patient database. In embodiments, the data within the patient database includes images 1232. The images associated with the patient can include photographic images, radiographic data such as x-ray images, chart data and so on. The data can also include medical/dental chart data (based on which inconsistencies between the charts and image modalities can be detected). In embodiments, the radiographic data comprises oral (dental) images of the individual. The oral images can include images collected during treatment of the individual. In embodiments, the oral images can include current and historical radiography of the individual. The phantom disease review can be based on analyzing the images collected during treatment of the individual. Embodiments include comparing the radiographic data from the individual with additional radiographic data from a plurality of other individuals. The additional radiographic data can include relevant radiographic data such as radiographic data that includes oral images from the plurality of other individuals. The comparison can include comparing the radiographic data from the individual against that data collected from other individuals known to exhibit a given disease. In some examples, the additional radiographic data can be taken from the plurality of other individuals while undergoing commensurate treatment to the individual. The treatment can include fillings, extractions, implants, etc.

The phantom disease review can be based on the additional radiographic data. The additional radiographic data can be taken from the individual while the individual is undergoing different treatment from a treatment indicated by the treatment clinical data. That is, the additional radiographic data can indicate that a treatment claimed to have been performed by a provider was not actually provided by the provider by either sending someone else's data or manipulating the data returning to the patient x record in the database 1230, the database can include appointment information 1234. The appointment information can include a specific appointment, further appointments, and past appointments. The patient x database can include treatment history data 1236. The treatment history data can include the history of some or all treatments provided to the individual over a time period, where the time period can include month, a year, the patient's lifetime, etc. The patient x database 1230 can include current provider information 1238. The current provider information can include a provider name, contact information such as phone number, email address, webpage, physical address, and the like. The patient x database records can include previous provider information 1240. The previous provider information can include one or more providers who provided treatments to the individual and information associated with each provider.

FIG. 23A shows an example 1300 of a manipulated x-ray image. Treatment clinical data associated with an individual can be analyzed to determine whether the treatment clinical data has been manipulated. The treatment clinical data can include descriptions of the treatment, images such as photographic or radiographic images, insurance information, and so on. Data such as radiographic data, image data, etc., can be manipulated. The manipulation of the data may be innocent or unintentional, while at other times the manipulation can include malicious or fraudulent manipulation. Treatment clinical data for an individual is accessed, where the treatment clinical data comprises radiographic data and data from one or more additional utilization systems concerning the individual. A review metric is generated for the individual, where the review metric is based on radiographic data analysis. In the example of FIG. 23A, an original image 1310, such as a radiographic image or x-ray, can include an unaltered or unmanipulated image. The original image can show a treatment performed. Data associated with the treatment performed can be included with treatment clinical data. The image can show a dental implant 1312. In addition to the dental implant, the image can show further detail 1314, where the further detail can be associated with the tooth to which the dental implant was applied. A second image 1320 is also shown in FIG. 23A, where the second image can represent an altered or manipulated version of the first image 1310. The manipulated image can show an implant 1322, where the implant 1322 can represent the implant 1312 seen in image 1310. Note however that other aspects of the image 1320 have been manipulated. An example of the image manipulation is shown in 1324. The manipulation of the image can include boosting contrast of the image, manipulating image sharpness, lightening shadows within the image, and the like. The image can be manipulated to imply that treatment was performed beyond or in addition to the treatment that was actually completed.

Figure 23B:
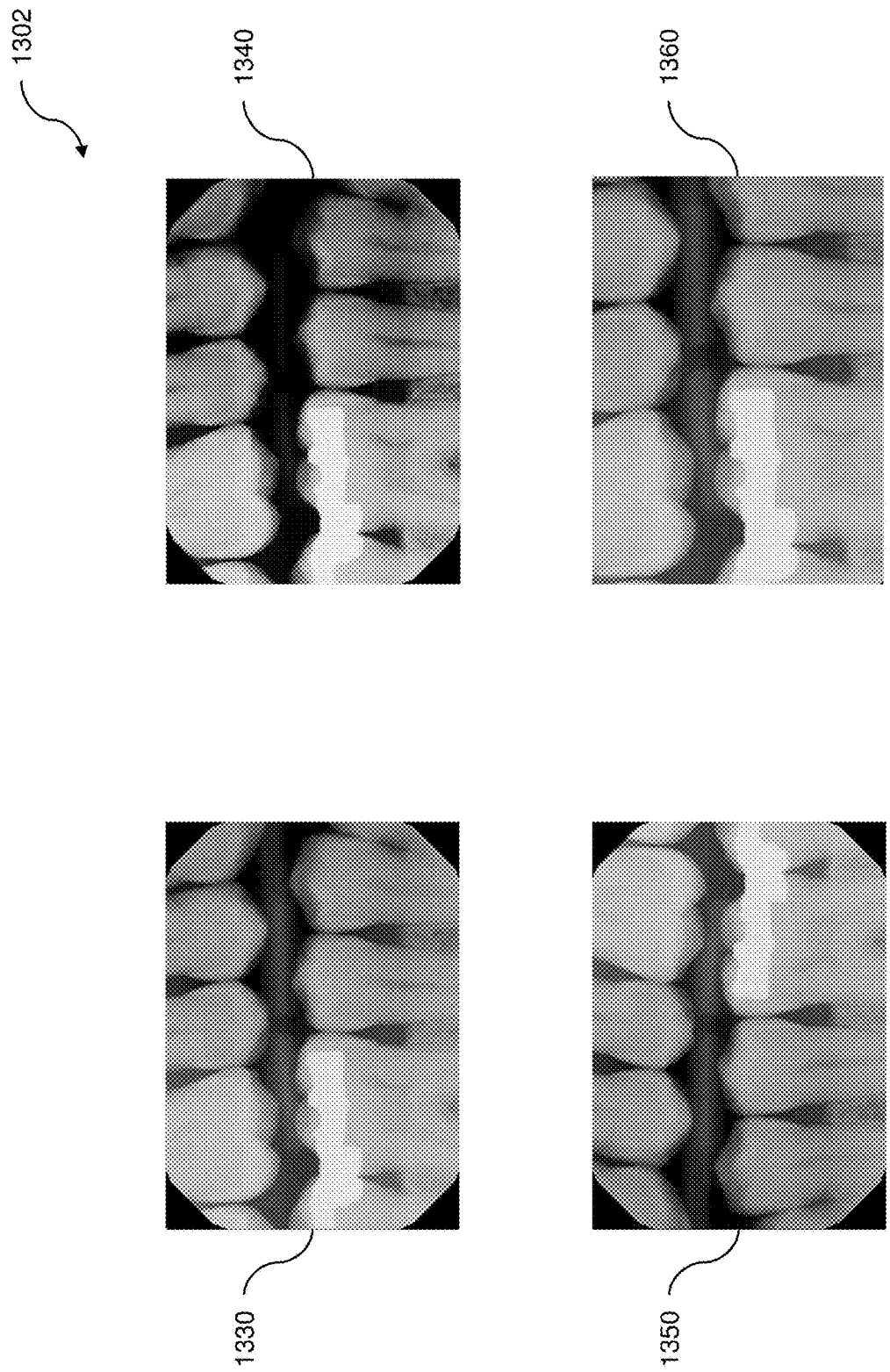
FIG. 23B shows duplicate x-ray image submissions.

FIG. 23B includes examples 1302 of duplicate x-ray image submission. Treatment clinical data can include radiographic data including images such as x-ray images. The radiographic or image data can include images of the individual before treatment was performed, after treatment was performed, and so on. Duplicate images can be included in the treatment clinical data by being provided in error, provided for a different individual, submitted maliciously or fraudulently, and on. Image 1330 shows an original image associated with an individual. The images can include an unaltered image such as an x-ray image. Image 1340 shows a darkened version of image 1330. The image 1340 can be darkened by changing an exposure value associated with the original image. Other adjustments that can be made can include adjusting contrast, adjusting highlights, lightening shadows, adjusting sharpness, and other image adjustments. While black and white images are shown, color images can also be included in the treatment clinical data. For color images, further adjustments can include adjusting saturation, temperature, tint, etc. The image 1350 shows the image 1330 rotated about a vertical axis, "flipped" left for right, or mirrored. In a usage example, a dental x-ray flipped about a vertical axis could imply that the treatment utilization could be associated with an opposite side of the mouth of the individual. Such a flipped image could be used to imply that dental treatment was applied to both sides of the individual's mouth rather than just one side. Image 1360 shows a resized version of image 1330. The resizing of the image can include enlarging the original image, shrinking the original image, and so on. In the example image 1360, the image has been enlarged. Otherwise, the image 1360 shows substantially similar treatment as that shown in image 1330. Comparison of the altered images to the original, whether by darkening, flipping, resizing, and so on, can be accomplished using one or more image processing techniques. In some embodiments, the comparison of the altered images can be detected using artificial intelligence techniques.

Figure 24:
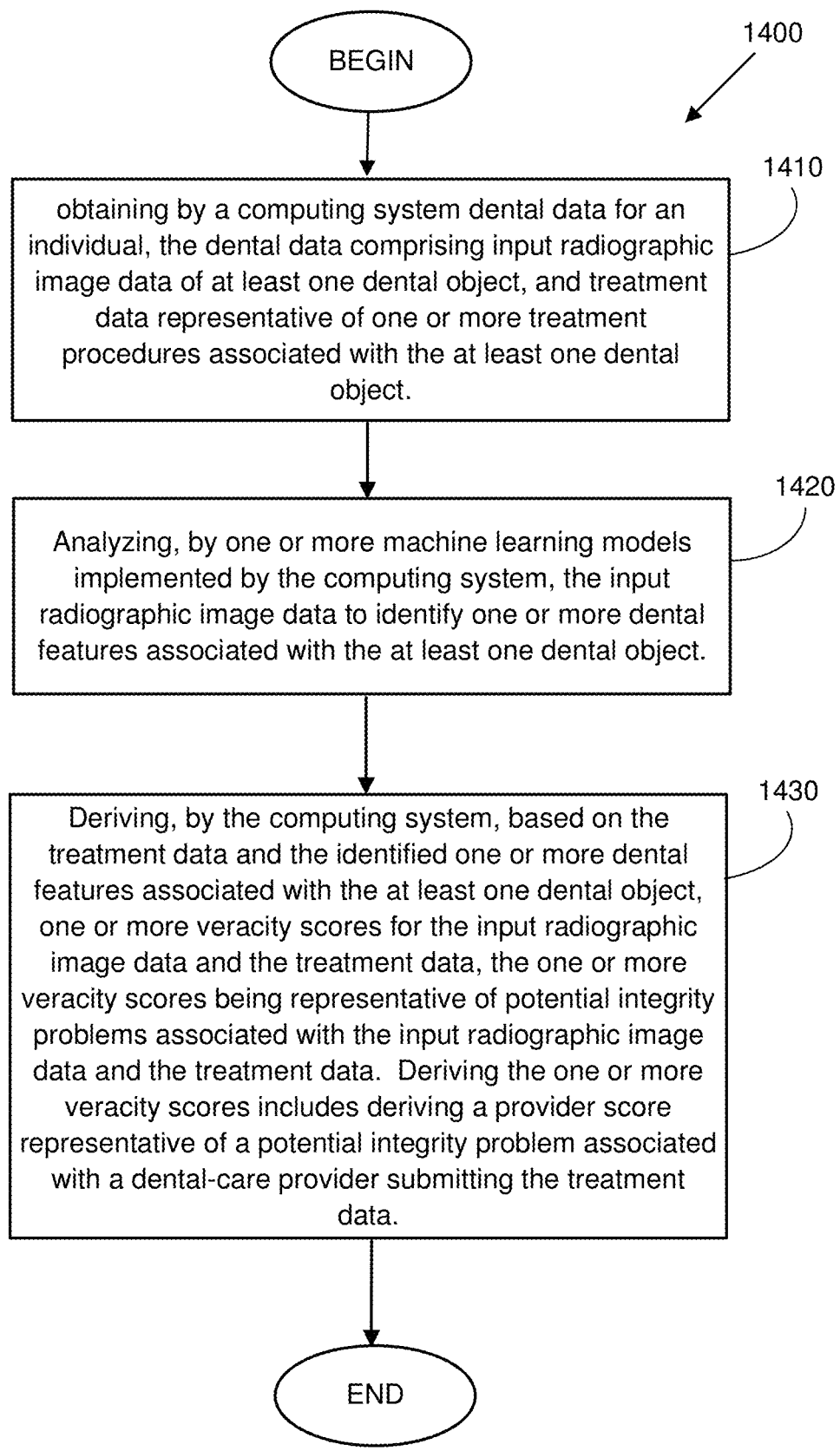
FIG. 24 is a flowchart of an example procedure for clinical data integrity detection.

With reference next to FIG. 24, a flowchart of an example procedure 1400 for utilization integrity detection is shown. The procedure 1400 may be performed on a system implementation that is based on some of the frameworks described herein, for example, the frameworks depicted in flows 900 and 1100 of FIGS. 19 and 21, that are configured to perform dental data analysis to compute various integrity/veracity metrics with respect to submitted claims (or requests for treatment pre-approval), including to compute a provider score that identifies or flags any issues specific to the dental-care provider submitting the claims (including issues identified over time that show problematic trends in the provider's submitted clinical data for the provider's patients). The procedure 1400 includes obtaining 1410 by a computing system dental data (also referred to as clinical data) for an individual, with the dental data comprising input radiographic image data of at least one dental object (e.g., a tooth), and treatment data representative of one or more treatment procedures associated with the at least one dental object. The dental data may be provided directly from a dental-care provider (via one or more intermediary nodes in a communications network such as the Internet) or from some central repository (possibly associated with an insurance company to whom treatment plans or claims are first submitted).

The procedure 1400 further includes analyzing 1420, by one or more machine learning models implemented by the computing system, the input radiographic image data to identify one or more dental features associated with the at least one dental object. Some of the data analysis performed at 1420 may be performed by one or more machine learning engines (which may be implemented similarly to the ML engines discussed in relation to FIG. 1-15 to perform calibration operations, or the ML engine implementations depicted in FIG. 16, which uses an ML model to identify features in a radiographic image, and determine based on areas enclosed by those features whether to approve or deny claims or requests for pre-approval). The features identified by the ML engine include various dental features indicative of dental clinical conditions (e.g., decaying portions), dental structures (different parts of the dental anatomy), dental corrective structures (e.g., implants, restorations, root canals, and so on), and labels/descriptors to classify or describe certain features and their attributes (e.g., locations and orientations of dental structure). The latter descriptors can be used to compare an incoming input image to archived images stored at a dental database (e.g., managed by the administrator running the integrity analysis frameworks described herein). Each type of the various features identified (or extracted) can be determined according to separate independent ML model implementations trained to identify that specific type of feature. Alternatively, one or more ML model can be trained and optimized to identify, and generate appropriate output (masks, marking, labels) for multiple feature types.

In some embodiments, the ML models are implemented to identify difference between one image and another. Under this ML differential approach, the ML engine is configured to receive input corresponding to two images (e.g., the input radiographic image, and some previously stored image against which the input radiographic image is being compared). It is to be noted that when a differential ML model is used, some pre-processing may be required on at least one of the images. Such pre-processing may include image calibration (e.g., in accordance with the implementations discussed in relation to FIGS. 1-15), image alignment, segmenting, or processing the images to generate compact data representative of the content and/or classification of the data.

As noted, the analysis of the input image data may include detection of suspicious anomalies that may indicate image manipulation, or recycling of a previously submitted image (to support a previous claim) in support of the current claim. Thus, in such embodiments, analyzing the input radiographic image data may include detecting anomalous features in the input radiographic image data, including determining one or more of, for example, whether a portion of the input radiographic image data substantially matches a portion of a previously stored radiographic image, and/or whether a portion of the input radiographic image data was modified. A determination that an input radiographic image contains these types of anomalies (and may therefore be part of a fraudulent claim) may result in termination of the remainder of the data analysis processing (since a finding of possible fraud would be dispositive of the outcome of the claim).

Having performed the learning-machine-based analysis, the procedure 1400 further includes deriving 1430, by the computing system, based on the treatment data and the identified one or more dental features associated with the at least one dental object, one or more integrity scores (also referred to as veracity scores) for the input radiographic image data and the treatment data, with the one or more integrity scores being representative of potential integrity problems associated with the input radiographic image data and the treatment data. Deriving the one or more integrity scores includes deriving a provider score representative of potential integrity problems associated with a dental-care provider submitting the treatment data.

As also discussed with respect to FIG. 21, the computation of a provider score may be based on computing various metrics that are each representative of different potential issues associated with the dental (utilization) data submitted (according to the identified features extracted through operation of the one or more learning machines employed in the analysis). The provider score can then be computed as a composite score that combines, under some formulation, the separately computed metrics and output of the dental data analysis. For example, and as noted above, the provider score can be computed as a weighted sum (or weighted sum of averages) of the various metrics computed. In one example of a metric computation (for use in computing a composite provider score), deriving the provider score may include computing an outlier score representative of a level of deviation between a treatment plan, specified in the treatment data for the at least one dental object to remedy a dental condition identified in the treatment data for the individual, and treatment plans to treat similar dental conditions associated with archived treatment data and archived radiographic image data for a plurality of other individuals. In another example, deriving the provider score may include determining, by the computing system, one or more possible treatment plans to remedy a dental condition identified in the treatment data for the individual, and computing an aggressiveness score representative of a complexity level difference between a specified treatment plan submitted by the dental-care provider to remedy the dental condition and the determined one or more possible treatment plans.

Deriving the provider score may also include, in some embodiments, computing a phantom disease score representative of a level of consistency between a treatment plan specified in the treatment data for the at least one dental object to remedy a dental condition identified in the treatment data for the individual, and identified features of the input radiographic image data detected by the computing system. The phantom disease score is computed to assess the existence of potential tampering of the supporting radiographic image data submitted with the treatment data. In this situation the treatment plan may be consistent with dental conditions or issues apparent in the radiographic image, but it is suspected that the provider may have submitted compromised image data that was altered in some way from the actual radiographic image data obtained for individual patient in order to support an unwarranted treatment plan. Examples of image data alteration include using at least a portion of a previously taken x-ray image (for the individual patient, or for some other patient), or manipulating at least a portion of the submitted image in some way. Thus, in some embodiments, computing the phantom disease score may include performing image manipulation detection on the input radiographic image data to determine whether a portion of the input radiographic image data was modified, or determining, based on future image data, that the treatment was never performed. In some examples, computing the phantom disease score may include performing a near-duplicate image detection on the input radiographic image data to determine whether a portion of the input radiographic image data, relating to an identified dental condition for the at least one dental object, substantially (or fully) matches a portion of a previously stored radiographic image.

Another metric used to assess a provider score is the phantom treatment score. Deriving the provider score may include computing, based on the treatment data associated with the input radiographic image data for the individual, and based on archived treatment data for one or more individuals treated by the dental-care provider, a phantom treatment score representative of extent to which the dental-care provider submits treatment plans inconsistent with associated dental conditions identified form the treatment data for the individual and from the archived treatment data.

As noted, in some situations, the utilization integrity analysis may also derive an area-based analysis of dental features detected in a radiographic image (in a manner similar to that discussed in relation to FIGS. 16-18) to determine if a proposed treatment plan is warranted in view of the radiographic image data provided. Thus, in such situations, deriving (in the procedure 1400) the one or more integrity scores may include identifying, by at least one of the one or more machine learning models, at least one first dental feature in the input radiographic image data for the at least one dental object (possibly indicative of the existence of a dental clinical condition for the at least one dental object), and at least one other feature in the dental object comprising at least partly a healthy dental structure, computing at least one dimensioned property representative of physical dimensions of the at least one first dental feature and the at least one other feature comprising at least partly the healthy dental structure (e.g., computing areas covered, or lengths of identified dental features, or distance between two or more identified features such as locations of CEJ lines), and deriving based on the at least one dimensioned property at least one dimensioned property ratio indicative of an extent of a dental clinical condition associated with the identified at least one dental feature of the at least one dental object. In such embodiments, the analysis may further include determining a treatment plan based on a comparison of the derived at least one dimensioned property ratio to a respective at least one pre-determined threshold value.

The procedure 1400 may also include a radiographic image data calibration procedure in order to make the source data compatible with the data that was used train the various ML models implemented for the clinical data integrity analysis, and to more accurately compare the input image to archived images (at least where the metrics being derived require such a comparison). The calibration processing can include determining the scale (e.g., in some standard-unit length, such as millimeter) that pixels in the received source image represent. As noted above, the proposed calibration processes are generally performed without requiring use of calibration objects to be included in captured image data. Those proposed processes instead rely on archival or other available information about the objects appearing in the captured image, or about the sensor devices that are used for capturing the image data. Thus, in such embodiments, obtaining the dental data may include receiving source radiographic image data represented according to pixel-based dimensions, and calibrating the source radiographic image data to produce the input radiographic image data represented in terms of estimated standard-unit dimensions, with the source radiographic image data being free of any non-dental calibration object. The various calibration processes used in relation to the procedure 1400 may be similar to the calibration processes discussed with respect to the procedure 800 of FIG. 18, and in relation to the various procedures discussed in relation to FIGS. 6-12.

Figure 25:
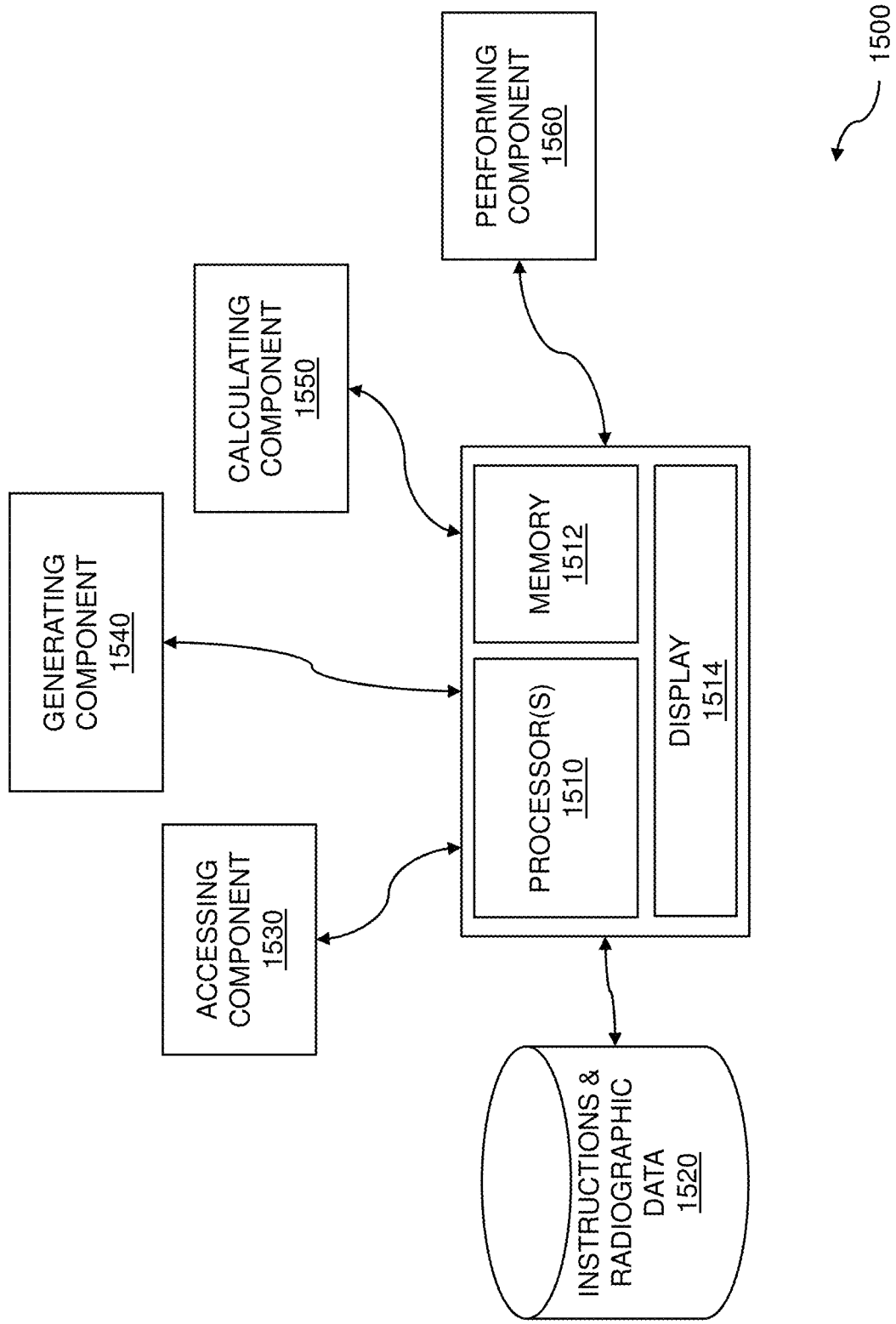
FIG. 25 is a system diagram for utilization analysis.

FIG. 25 is a diagram of an example system 1500 to perform utilization analysis (the system 1500 may be used, at least in part, to perform the procedures and processes depicted in FIG. 19-24, or any of the procedures and processes shown in relation to FIGS. 2-13 and 18). As discussed herein, utilization analysis uses multisystem machine learning for utilization integrity detection. Alternative implementations of systems to perform the procedures and processes described in relation to FIGS. 19-24 include the systems of FIGS. 1A-B, and 14-16. The systems described in relation to those figures may be modified, as needed, as to be configured to perform the processes and procedures described in relation to FIGS. 19-24.

The system 1500 can include one or more processors 1510 attached to a memory 1512 which stores instructions. The system 1500 can include a display 1514 coupled to the one or more processors 1510 for displaying data, intermediate steps, instructions, x-ray images, treatment clinical data, and so on. In embodiments, one or more processors 1510 are attached to the memory 1512 where the one or more processors, when executing the instructions which are stored, are configured to: access treatment clinical data for an individual, with the treatment clinical data including radiographic data and data from one or more additional utilization systems concerning the individual; generate a review metric for the individual, with the review metric being based on radiographic data analysis; generate a utilization system score, based on data from at least one of the one or more additional utilization systems; calculate a clinical data score, based on the review metric and the utilization system score; and perform an ongoing analysis of the treatment clinical data, based on additional treatment clinical data for the individual. In some embodiments, the system is configured to perform the processes 800 and 1400 shown in FIGS. 18 and 21, respectively. The utilization integrity detection can be used to detect fraudulent data. Fraudulent data can include altered data, duplicate data, and so on. The utilization integrity detection can be accomplished using the processors 1510, computers, servers, remote servers, cloud-based servers, and the like.

The system 1500 can include a collection of instructions and radiographic data 1520. The instructions and data 1520 may be stored using techniques such as electronic storage coupled to the one or more processors, a database, one or more code libraries, precompiled code segments, source code, apps, or other suitable formats. The instructions can include instructions for generating a review metric based on radiographic data analysis. The radiographic data can include x-ray data. The instructions can also include instructions for generating a utilization system score (e.g., veracity/integrity scores) based on data from at least one of the one or more additional utilization systems. The additional utilization systems can include systems for performing outlier analysis, reviewing phantom disease or phantom treatment, and the like. The instructions can include instructions for calculating a utilization score based on the review metric and the utilization system score. The reviewing can be based on a value, a threshold, a percentage, a range of values, etc. The instructions can include instructions for performing ongoing analysis of the treatment clinical data based on additional treatment clinical data for the individual. The data can include x-ray data, image data, treatment data, patient medical history data, physician and healthcare team notes, dentist notes, and so on. The data can include data from an insurance database such as provider data.

The system 1500 can include an accessing component 1530. The accessing component 1530 can include functions and instructions for accessing treatment clinical data for an individual. The clinical data that is accessed can be available in a local database, a remote, cloud-based database, a mesh-based database; can be uploaded by a user, can be sent directly from a provider's office (including directly from an imaging apparatus that can establish a communication link to a communications network), and so on. The clinical data can be encrypted to meet security and handling requirements such as Health Insurance Portability and Accountability Act (HIPAA) requirements. The treatment information data can include data contained within one or more insurance databases, one or more provider databases, patient data, and the like. The treatment clinical data can include radiographic data and data from one or more additional utilization systems concerning the individual. The additional clinical data for the individual can include medical history data, insurance data, past treatment data, recommended treatment data, and so on.

The system 1500 can include a generating component 1540. In embodiments, the generating component 1540 can include functions and instructions for generating a review metric for the individual, with the review metric being based on radiographic data analysis. The review metric can be used to verify veracity of radiographic data, a likelihood that the radiographic data is unaltered or accurate, and so on. In embodiments, the review metric can be based on a value, a percentage, a range of values, a probability, and the like. In embodiments, the generating component 1540 of the system 1500 can further include functions and instructions for generating one or more utilization system scores/metrics, based on data from at least one of the one or more additional utilization systems. The one or more such scores can each include a value, a percentage, a range of values, etc. The utilization score can include an "out of 10" or "out of 100" score such as 93 out of 100. The clinical data score can be used for a variety of applications including fraud detection, data duplication such as insurance claims data, and the like. One example metric that can be generated is an outlier metric for the treatment clinical data. The outlier metric can be used to determine whether a treatment for which payment is sought is statistically different from or substantially similar to treatments for other individuals. As noted, in some embodiments, the system 1500 can compute an aggressiveness metric for the treatment clinical data. An aggressiveness metric can be based on whether an "aggressive" approach was taken for a treatment where a simpler and less expensive treatment would have been indicated or would have sufficed. In further embodiments, the utilization system can produce a metric that is based on a weighted average of an outlier metric and an aggressiveness metric. Since an individual can have preexisting health conditions or other health issues that potentially present complications to the treatment, an outlier metric value and an aggressiveness metric do not necessarily indicate that the utilization was unwarranted. In embodiments, the weighted average of the outlier metric and the aggressiveness metric can be based on consideration of an individual's other health factors.

The system 1500 can include a calculating component 1550. The calculating component 1550 can include functions and instructions for calculating a clinical data score, based on the review metric and the utilization system score. The utilization system scores can be based on a value, a range of values, a percentage, a threshold, and so on. The utilization system score can be based on assessments such as "high utilization", "low utilization", and "average utilization". The calculating component can be used to calculate further scores. In embodiments, the radiographic data (discussed previously) allows computing a phantom disease review score. A phantom disease can include a disease reported by an individual or a provider, where the disease is not actually present in the individual. In embodiments, the phantom disease review score can indicate duplicated treatment clinical data. A provider can present treatment clinical data which was also reported at an earlier date, for a different patient, etc. In other embodiments, the radiographic data can be used for computation of a phantom treatment review score. The phantom treatment review score can be based on the duplicated treatment, on unwarranted treatment, on incomplete treatment, on overtreatment, etc. In embodiments, the phantom treatment review score can indicate inconsistent treatment clinical data. Inconsistent treatment data can include treatment data for a different disease, inconsistent processes or application between treatments, and the like.

In embodiments, the treatment provider supplies dental treatments to the individual. The treatment provider can provide other treatments such as an annual physical, specialized treatments such as dental treatments, ophthalmic, orthopedic, cardiac, oncologic treatment, and the like. Further embodiments can include calculating a provider score for a treatment provider. The provider score can be based on utilization system data (including radiographic image data and treatment data, which may be text-based narratives and descriptions of the treatments that were performed, or are proposed to be performed) associated with the treatment provider, and possibly collected over a period of time. The provider score can be used to evaluate the treatment provider such as issuing evaluations based on a letter grade. Further embodiments include calculating a false representation metric for the radiographic data of the individual based on the oral images with manipulations that display false representations. False representations can be based on manipulated data such as manipulated radiographic data. Manipulated radiographic data can include radiographic images that are duplicated, enhanced, darkened or lightened, enlarged or reduced, reversed (e.g., flipped left to right), etc.

The system 1500 can further include a performing component 1560. The performing component 1560 can include functions and instructions for performing an ongoing analysis of the treatment clinical data, based on additional treatment clinical data for the individual. The additional data can comprise data collected from a variety of sources. In embodiments, the additional treatment clinical data for the individual can include longitudinal treatment clinical data for the individual. The ongoing analysis of the treatment clinical data can be used to determine trends in treatment such as increases or decreases in treatment, treatment "hotspots" where the number of treatments is elevated above a nominal or typical value, and so on. The performing ongoing analysis can be used to determine increasing or decreasing numbers of fraudulent utilization claims. In embodiments, the ongoing analysis is performed autonomously. The performing autonomous analysis can be based on using applications, apps, or codes. The ongoing analysis can be based on artificial intelligence techniques. The ongoing analysis can be performed online or offline with the generating, calculating, and performing techniques.

The system 1500 can include a computer program product embodied in a non-transitory computer readable medium for utilization analysis, the computer program product comprising code which causes one or more processors to perform operations of the procedures and processes described herein in relation to FIGS. 1-24.

Each of the above methods and processes described herein may be executed on one or more processors on one or more computer systems. Each of the above methods may be implemented on a semiconductor chip and programmed using special purpose logic, programmable logic, and so on. Embodiments may include various forms of distributed computing, client/server computing, and cloud-based computing. Further, it will be understood that the depicted steps or boxes contained in this disclosure's flow charts and flow diagrams are solely illustrative and explanatory. The steps may be modified, omitted, repeated, or reordered without departing from the scope of this disclosure. Further, each step may contain one or more sub-steps.

Computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

As noted, the machine learning engines used by various systems and frameworks described herein (as discussed in relation to FIGS. 1-24) may be implemented as neural networks. Such neural networks may be realized using different types of neural network architectures, configuration, and/or implementation approaches. Examples neural networks that may be used include convolutional neural network (CNN), feed-forward neural networks, recurrent neural networks (RNN), transformer network, etc. Feed-forward networks include one or more layers of nodes ("neurons" or "learning elements") with connections to one or more portions of the input data. In a feedforward network, the connectivity of the inputs and layers of nodes is such that input data and intermediate data propagate in a forward direction towards the network's output. There are typically no feedback loops or cycles in the configuration/structure of the feed-forward network. Convolutional layers allow a network to efficiently learn features by applying the same learned transformation(s) to subsections of the data. A transformer network is a machine learning configuration (used, for example, in natural language processing and computer vision applications) that includes an attention mechanism to weight network connections according to their significance. Other examples of learning engine approaches/architectures that may be used include generating an auto-encoder and using a dense layer of the network to correlate with probability for a future event through a support vector machine, constructing a regression or classification neural network model that indicates a specific output from data (based on training reflective of correlation between similar records and the output that is to be identified), etc.

Implementations described herein, including implementations using neural networks, can be realized on any computing platform, including computing platforms that include one or more microprocessors, microcontrollers, and/or digital signal processors that provide processing functionality, as well as other computation and control functionality. The computing platform can include one or more CPU's, one or more graphics processing units (GPU's, such as NVIDIA GPU's), and may also include special purpose logic circuitry, e.g., an FPGA (field programmable gate array), an ASIC (application-specific integrated circuit), a DSP processor, an accelerated processing unit (APU), an application processor, customized dedicated circuit, etc., to implement, at least in part, the processes and functionality for the neural networks, processes, and methods described herein. The computing platforms typically also include memory for storing data and software instructions for executing programmed functionality within the device. Generally speaking, a computer accessible storage medium may include any non-transitory storage media accessible by a computer during use to provide instructions and/or data to the computer. For example, a computer accessible storage medium may include storage media such as magnetic or optical disks and semiconductor (solid-state) memories, DRAM, SRAM, etc. The various learning processes implemented through use of the neural networks may be configured or programmed using TensorFlow (a software library used for machine learning applications such as neural networks). Other programming platforms that can be employed include keras (an open-source neural network library) building blocks, NumPy (an open-source programming library useful for realizing modules to process arrays) building blocks, etc.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the scope of the present teachings.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limit the scope of the invention, which is defined by the scope of the appended claims. Any of the features of the disclosed embodiments described herein can be combined with each other, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

APPENDIX A—EXAMPLE INSURANCE CODES AND DESCRIPTION FOR VARIOUS DENTAL PROCEDURES

The following examples of code-specific relationships, if identified in ratios above routine clinical use, may raise concern for fraudulent, wasteful, or abusive overutilization. They should be measured against the defined policies and administrative systems in place, and the ratio threshold determined by the benchmark historical and outlier data held within the company.

Diagnostic Services (D0100-0999)
D0150/0180—Comprehensive Oral Evaluation/Comprehensive periodontal evaluation
  Concern: Submitted in lieu of regular periodic exam (D0120), limited oral exam—problem focused (0140) or re-evaluation—limited (0170), or assessment of a patient (0191)
  Reason: Upcoding services
D0210—Complete series of radiographic images
  Concern: Filing for D0210 when fewer site-specific images are obtained, such as intraoral—periapical (0220/0230) and bitewing—single or multiple (0270/0272/0273)
  Reason: Upcoding services
D0274/0272—Bitewing (4 or 2) radiographic images
  Concern: Filing with two additional periapical images (D0220/0230) to capture anterior teeth with no medical necessity
  Reason: Performing services without medical necessity
D0220/0230—Periapical (1 or more) radiographic images
  Concern: Filing for reimbursement with crown insertion (D2740/2750) are usually considered working films as part of the primary procedure of cementing the crown
  Reason: Performing services without medical necessity
Preventive Services (D1000-1999)
D1351—Sealant (per tooth)
  Concern: Filing each sealant as single surface posterior resin (D2391)
  Reason: Filing for services not rendered
Restorative Services (D2000-2999)
D2332—Resin-based composite—three surfaces, anterior
  Concern: Filing for treatment of Class III restoration (MLF, DLF), for teeth #6-11 and 22-27
  Reason: Upcoding services
D2335—Resin-based composite—four or more surfaces involving the incisal angle, anterior
  Concern: May be filed for wear and abrasion without further documentation for teeth #6-11 and 22-27
  Reason: Performing services without medical necessity
D2393—Resin-based composite—three surfaces, posterior
  Concern: Filing multiple teeth in the posterior, particularly premolars, are suspicious of wear, abrasions and abfractions (most dental plans do not benefit for restorations place for wear, abrasions or abfractions)
  Reason: Performing services without medical necessity
D2720/2721—Crown—resin with high noble metal/Crown—resin with predominantly base metal
  Concern: Submitting as D2750 (porcelain fused to high noble metal) to increase reimbursement
  Reason: Upcoding services
D2950—Core Build-up, including any pins where required
  Concern: Filed with crown codes (D2750, 2740) should not be routine if replacing minor existing restorations prior to crown preparation; likely required in less than 50% of crown restorations (not approaching 1:1)
  Reason: Upcoding services
Periodontal Services (D4000-4999)
D4249—Clinical crown lengthening—hard tissue
  Concern: Submitted in lieu of gingivectomy or gingivoplasty to allow access for restorative procedure (D4212) when performed on the same day as crown delivery
  Reason: Upcoding services
D4341/4342—Periodontal scaling and root planning—four or more teeth/one to three teeth
  Concern: Submitted in lieu of prophylaxis—adult (D1110)
  Reason: Upcoding services
D4355—Full mouth debridement—to enable a comprehensive oral evaluation and diagnosis
  Concern: May be submitted in lieu of a prophylaxis where there is gross calculus as part of periodic maintenance rather than to enable evaluation and diagnosis
  Reason: Upcoding services; Performing services without medical necessity
D4381—Localized delivery of antimicrobial agents via a controlled release vehicle
  Concern: If placed routinely without proper diagnostic and clinical justification.
  Reason: Performing services without medical necessity

What is claimed is:

1. A computer-implemented method for clinical data analysis comprising:
  obtaining dental data for an individual, wherein the dental data comprises input radiographic image data for at least one dental object;
  identifying, by one or more machine learning models, at least one first dental feature in the input radiographic image data for the at least one dental object, and at least one other feature in the dental object comprising at least partly a healthy dental structure;

computing at least one dimensioned property representative of physical dimensions of the at least one first dental feature and the at least one other feature comprising at least partly the healthy dental structure;

deriving based on the at least one dimensioned property at least one dimensioned property ratio indicative of an extent of a dental clinical condition associated with the identified at least one first dental feature of the at least one dental object; and determining a treatment plan based on a comparison of the derived at least one dimensioned property ratio to a respective at least one pre-determined threshold value.

2. The method of claim 1, wherein computing the at least one dimensioned property comprises computing one or more of: areas of the identified at least one first dental feature and the at least one other feature, or lengths of the identified at least one first dental feature and the at least one other feature;

and wherein deriving the at least one dimensioned property ratio comprises one or more of: deriving an area ratio of an area for the at least one first dental feature and area for the at least one other feature, or deriving a length ratio of a length of the at least one first dental feature and a length of the at least one other feature.

3. The method of claim 1, wherein the at least one first dental feature comprises one or more of: a decaying tooth portion for a tooth, a filling region for the tooth, a restoration, or bone loss, and wherein the at least one other feature comprises one or more of: a clinical crown structure for the tooth, or root length.

4. The method of claim 1, wherein identifying, by the learning machine, the at least one first dental feature and the at least one other feature comprises:

generating masks, by the learning machine, representative of the at least one first dental feature and the at least one other feature comprising at least partly the healthy dental structure.

5. The method of claim 1, wherein determining the treatment plan comprises one or more of:

automatically determining by machine learning model a proposed treatment plan to treat an abnormal dental feature; or determining based on the derived dimensioned property ratio whether to approve a dental-care-provider treatment plan submitted by a dental-care provider.

6. The method of claim 1, wherein obtaining the dental data comprises:

receiving source radiographic image data represented according to pixel-based dimensions; and calibrating the source radiographic image data to produce the input radiographic image data represented in terms of estimated standard-unit dimensions.

7. The method of claim 6, wherein the estimated standard-unit dimensions comprises millimeter (mm) units.

8. The method of claim 6, wherein calibrating the source radiographic image data comprises:

selecting a segmenter or an object detector;

predicting source masks and source points of the at least one dental object appearing in the source radiographic image data using the segmenter and the object detector;

providing the source radiographic image data and image metadata, comprising the source masks and source points, to a calibration process selector;

selecting by the calibration process selector at least one measurement process from a set of measurement processes according to the source radiographic image data and the image metadata;

deriving a sensor pixel-to-standard-unit ratio using the selected at least one measurement process; and generating the input radiographic image data and resultant calibrated metadata, comprising calibrated masks and points on the dental object, using calibrated measurements of the at least one dental object based on the sensor pixel-to-standard-unit ratio and the image metadata.

9. The method of claim 8, wherein deriving the sensor pixel-to-standard-unit ratio using the selected at least one measurement process comprises:

determining a sensor type for the source radiographic image data;

determining sensor characteristics based on the determined sensor type;

determining pixel dimensions for the source radiographic image data; and deriving the sensor pixel-to-standard-unit ratio based on the determined sensor characteristics and the determined pixel dimensions for the source radiographic image data.

10. The method of claim 8, wherein deriving the sensor pixel-to-standard-unit ratio using the selected at least one measurement process comprises:

identifying from the source radiographic image data teeth without restorations;

determining distances in pixels between mesial and distal Cemento Enamel Junction (CEJ) points for the identified teeth;

deriving a plurality of pixel-to-standard-unit ratios using the determined distances in pixels and based on pre-determined standard average distances between the mesial and distal CEJ points for each of the identified teeth; and computing an average pixel-to-standard-unit ratio from the derived plurality of pixel-to-standard-unit ratios.

11. The method of claim 8, wherein deriving a sensor pixel-to-standard-unit ratio using the selected at least one measurement process comprises:

determining one or more outer borders for respective one or more dental objects appearing in the source radiographic image data;

comparing the one or more outer borders to 2D projections in a projection dictionary, the 2D projections being at incremental distance and angles generated from 3D dental image data, to identify a match between the one or more outer borders and the 2D projections in the projection dictionary;

estimating a viewing angle at which the source radiographic image data was obtained based on the identified match between the one or more outer borders and the 2D projections in the projection dictionary; and deriving the sensor pixel-to-standard-unit ratio based on the estimated angle at which the source radiographic image data was obtained.

12. The method of claim 8, wherein deriving a sensor pixel-to-standard-unit ratio using the selected at least one measurement process comprises:

detecting an implant structure appearing in the source radiographic image data;

determining implant attributes based on the source radiographic image data for the detected implant structure;

comparing the determined implant attributes for the detected implant structure to stored implant attributes included in implant data records, maintained in an implant structure database, for known manufactured implants to identify a match between the determined implant attributes and the stored implant attributes included in the stored implant data records; and deriving the sensor pixel-to-standard-unit ratio based on stored geometrical information associated with a selected one of the implant data records that most closely matches the implant attributes determined from the source radiographic image data.

13. The method of claim 8, wherein deriving a sensor pixel-to-standard-unit ratio using the selected at least one measurement process comprises:

detecting an implant structure appearing in the source radiographic image data;

determining implant attributes, based on the source radiographic image data for the detected implant structure;

comparing the determined implant attributes for the detected implant structure to stored implant attributes included in implant data records, maintained in an implant structure database, for known manufactured implants to identify a match between the determined implant attributes and the stored implant attributes included in the stored implant data records;

determining an outer border for the detected implant structure appearing in the source radiographic image data;

comparing the outer border to 2D projections maintained in a projection dictionary, the 2D projections being at incremental distance and angles generated from 3D dental image data, to identify a match between the outer border and the 2D projections in the projection dictionary;

estimating a viewing angle at which the source radiographic image data was obtained based on the identified match between the outer border and the 2D projections in the projection dictionary; and deriving the sensor pixel-to-standard-unit ratio based on the estimated angle at which the source radiographic image data was obtained, and based on stored geometrical information associated with a selected one of the implant data records that most closely matches the implant attributes determined from the source radiographic image data.

14. The method of claim 13, wherein deriving the sensor the sensor pixel-to-standard-unit ratio comprises:

estimating viewing angles for other dental objects detected in the source radiographic image data based on a position of the implant structure relative to the other dental structure and based on the viewing angle at which the source radiographic image data was obtained; and deriving the sensor pixel-to-standard-unit ratio based on the estimated viewing angles for the other dental structures detected in the source radiographic image data, and based on the stored geometrical information associated with the selected one of the implant data records that most closely matches the implant attributes determined from the source radiographic image data.

15. A system for clinical data analysis comprising:

a communication interface to obtain dental data for an individual, wherein the dental data comprises input radiographic image data for at least one dental object;

one or more memory devices; and one or more processor-based devices, coupled to the communication interface and to the one or more memory devices, to:

identify, by one or more machine learning models, at least one first dental feature in the input radiographic image data for the at least one dental object, and at least one other feature in the dental object comprising at least partly a healthy dental structure;

compute at least one dimensioned property representative of physical dimensions of the at least one first dental feature and the at least one other feature comprising at least partly the healthy dental structure;

derive based on the at least one dimensioned property at least one dimensioned property ratio indicative of an extent of a dental clinical condition associated with the identified at least one first dental feature of the at least one dental object; and determine a treatment plan based on a comparison of the derived at least one dimensioned property ratio to a respective at least one pre-determined threshold value.

16. The system of claim 15, wherein the one or more processor-based devices configured to compute the at least one dimensioned property are configured to compute one or more of: areas of the identified at least one first dental feature and the at least one other feature, or lengths of the identified at least one first dental feature and the at least one other feature;

and wherein the one or more processor-based devices configured to derive the at least one dimensioned property ratio are configured to perform one or more of: derive an area ratio of an area for the at least one first dental feature and area for the at least one other feature, or derive a length ratio of a length of the at least one first dental feature and a length of the at least one other feature.

17. The system of claim 15, wherein the at least one first dental feature comprises one or more of: a decaying tooth portion for a tooth, or a filling region for the tooth, and wherein the one of the at least one other feature comprises a clinical crown structure for the tooth.

18. The system of claim 15, wherein the one or more processor-based devices configured to identify, by the learning machine, the at least one first dental feature and the at least one other feature are configured to:

generate masks, by the learning machine, representative of the at least one first dental feature and the at least one other feature comprising at least partly the healthy dental structure.

19. The system of claim 15, wherein the communication interface configured to obtain the dental data is configured to receive source radiographic image data represented according to pixel-based dimensions;

and wherein the one or more processor-based devices are further configured to calibrate the source radiographic image data to produce the input radiographic image data represented in terms of estimated standard-unit dimensions, wherein the source radiographic image data is free of any non-dental calibration objects.

20. A non-transitory computer readable media storing a set of instructions, executable on at least one programmable device, to:

obtain dental data for an individual, wherein the dental data comprises input radiographic image data for at least one dental object;

identify, by one or more machine learning models, at least one first dental feature in the input radiographic image data for the at least one dental object, and at least one other feature in the dental object comprising at least partly a healthy dental structure;

compute at least one dimensioned property representative of physical dimensions of the at least one first dental feature and the at least one other feature comprising at least partly the healthy dental structure;
derive based on the at least one dimensioned property at least one dimensioned property ratio indicative of an extent of a dental clinical condition associated with the identified at least one first dental feature of the at least one dental object; and
determine a treatment plan based on a comparison of the derived at least one dimensioned property ratio to a respective at least one pre-determined threshold value.

* * * * *